United States Patent
Reineke et al.

(10) Patent No.: US 11,986,533 B2
(45) Date of Patent: May 21, 2024

(54) MACROMONOMERS AND BOTTLE BRUSH POLYMERS FOR DELIVERY OF BIOLOGICAL AGENTS

(71) Applicant: Regents of the University of Minnesota, Minneapolis, MN (US)

(72) Inventors: Theresa Reineke, Vadnais Heights, MN (US); Frank S. Bates, Saint Louis Park, MN (US); Monica Ohnsorg, Chanhassen, MN (US)

(73) Assignee: Regents of the University of Minnesota, Minneapolis, MN (US)

( * ) Notice: Subject to any disclaimer, the term of this patent is extended or adjusted under 35 U.S.C. 154(b) by 293 days.

(21) Appl. No.: 17/648,642

(22) Filed: Jan. 21, 2022

(65) Prior Publication Data

US 2022/0339288 A1    Oct. 27, 2022

Related U.S. Application Data

(60) Provisional application No. 63/199,785, filed on Jan. 25, 2021.

(51) Int. Cl.
*A61K 47/59* (2017.01)
*C08G 81/02* (2006.01)

(52) U.S. Cl.
CPC .......... *A61K 47/59* (2017.08); *C08G 81/024* (2013.01)

(58) Field of Classification Search
CPC ..... C08G 81/028; A61K 9/146; A61K 9/4866
See application file for complete search history.

(56) References Cited

PUBLICATIONS

Vohidov et al, ABC triblock bottlebrush copolymer-based injectable hydrogels: design, synthesis, and application to expanding the therapeutic index of cancer immunochemotherapy, Chem. Sci., May 2020 11, 5974.*
"Tamoxifen for Early Breast Cancer: an Overview of the Randomised Trials," The Lancet, vol. 351, May 16, 1998, pp. 1451-1467.
Baghel et al., "Polymeric Amorphous Solid Dispersions: A Review of Amorphization, Crystallization, Stabilization, Solid-State Characterization, and Aqueous Solubilization of Biopharmaceutical Classification System Class II Drugs," Journal of Pharmaceutical Sciences, Jan. 2016, 18 pp.
Bross et al., "FDA Drug Approval Summaries: Fulvestrant," The Oncologist, vol. 7, No. 6, Dec. 2002, pp. 477-480.
Coburn et al., "Potent and Specific Inhibition of Human Immunodeficiency Virus Type 1 Replication by RNA Interference," Journal of Virology, vol. 76, No. 18, Sep. 2002, pp. 9225-9231.
Connor et al., "Circumventing Tamoxifen Resistance in Breast Cancers Using Antiestrogens That Induce Unique Conformational Changes in the Estrogen Receptor1," Cancer Research, Apr. 1, 2001, pp. 2917-2922.

Curatolo et al., "Utility of Hydroxypropylmethylcellulose Acetate Succinate (HPMCAS) for Initiation and Maintenance of Drug Supersaturation in the GI Milieu," Pharmaceutical Research, vol. 26, No. 6, Jun. 2009, pp. 1419-1431.
Dalsin et al., "Solution-State Polymer Assemblies Influence BCS Class II Drug Dissolution and Supersaturation Maintenance," Biomacromolecules, Feb. 10, 2014, vol. 15, No. 2, pp. 500-511.
Friesen et al., "Hydroxypropyl Methylcellulose Acetate Succinate-Based Spray-Dried Dispersions: An Overview," Molecular Pharmaceutics, vol. 5, No. 6, Dec. 1, 2008, pp. 1003-1019.
Gombos, "Selective Oestrogen Receptor Degraders in Breast Cancer: a Review and Perspectives," Current Opinion in Oncology, vol. 3, No. 5, Sep. 2019, pp. 424-429.
Hernando et al., "Oral Selective Estrogen Receptor Degraders (SERDs) as a Novel Breast Cancer Therapy: Present and Future from a Clinical Perspective," International Journal of Molecular Sciences, vol. 22, No. 15, Aug. 2021, 21 pp.
Hultsch et al., "Association of Tamoxifen Resistance and Lipid Reprogramming in Breast Cancer," BMC Cancer, Aug. 24, 2018, 14 pp.
Jaiyesimi et al., "Use of Tamoxifen for Breast Cancer: Twenty-Eight Years Later," Journal of Clinical Oncology, vol. 13, No. 2, Feb. 1995, pp. 513-529.
Jakes, "Regularized Positive Exponential Sum (REPES) Program—A Way of Inverting Laplace Transform Data Obtained by Dynamic Light Scattering," Collection of Czechoslovak Chemical Communications, vol. 60, No. 11, Sep. 17, 1995, pp. 1781-1797.
Johnson et al., "Impact of Polymer Excipient Molar Mass and End Groups on Hydrophobic Drug Solubility Enhancement," Macromolecules, Jan. 25, 2017, 11 pp.
Kasim et al., "Molecular Properties of WHO Essential Drugs and Provisional Biopharmaceutical Classification," Molecular Pharmaceutics, vol. 1, No. 1, Jan. 12, 2004, pp. 85-96.
Kohler et al., "Annual Report to the Nation on the Status of Cancer, 1975-2011, Featuring Incidence of Breast Cancer Subtypes by Race/Ethnicity, Poverty, and State," Journal of the National Cancer Institute, vol. 107, No. 6, Mar. 2015, 25 pp.
Lai et al., "Identification of GDC-0810 (ARN-810), an Orally Bioavailable Selective Estrogen Receptor Degrader (SERD) that Demonstrates Robust Activity in Tamoxifen-Resistant Breast Cancer Xenografts," Journal of Medicinal Chemistry, vol. 58, No. 12, Apr. 2015, pp. 4888-4904.

(Continued)

*Primary Examiner* — Jeffrey C Mullis
(74) *Attorney, Agent, or Firm* — Shumaker & Sieffert, P.A.

(57) ABSTRACT

A composition includes a macromolecular polyacrylamide copolymer excipient with an α-end including a ROMP-active norbornene end-group and a ω-end including a terminal monomer with an end group chosen from: a hydrogen atom (H); or a functionalized acrylate with functionality chosen from alkyl, hydroxyl (OH), methyl-polyethylene glycol ((PEG)-CH₃), hydroxy-PEG (PEG-OH), carboxylic acid (COOH), and combinations thereof. A biological compound chosen from active pharmaceutical ingredients, proteins, polynucleotides, and mixtures and combinations thereof is non-covalently bound with the macromolecular excipient.

20 Claims, 34 Drawing Sheets

(56) References Cited

PUBLICATIONS

Lai et al., "Induced Protein Degradation: an Emerging Drug Discovery Paradigm," Nature Reviews Drug Discovery, vol. 16, No. 2, Feb. 2017, 32 pp.

Li et al., "Enhanced Performance of Blended Polymer Excipients in Delivering a Hydrophobic Drug through the Synergistic Action of Micelles and HPMCAS," Langmuir, vol. 33, No. 11, Mar. 2017, pp. 2837-2848.

Li et al., "Maintaining Hydrophobic Drug Supersaturation in a Micelle Corona Reservoir," Macromolecules, Jan. 3, 2018, 12 pp.

Li et al., "Microstructure Formation for Improved Dissolution Performance of Lopinavir Amorphous Solid Dispersions," Molecular Pharmaceutics, vol. 16, No. 4, Apr. 2019, pp. 1751-1765.

Li et al., "Polymer Nanogels as Reservoirs to Inhibit Hydrophobic Drug Crystallization," ACS Nano, vol. 13, No. 2, Feb. 2019, 12 pp.

Li et al., "Surface Properties of Bottlebrush Polymer Thin Films," Macromolecules, vol. 45, No. 17, Sep. 2012, pp. 7118-7127.

Lin et al., "Control of Grafting Density and Distribution in Graft Polymers by Living Ring-Opening Metathesis Copolymerization," Journal of the American Medical Society, vol. 139, No. 10, pp. 3896-3903.

Lu et al., "Selective Estrogen Receptor Degraders (SERDs): A Promising Strategy for Estrogen Receptor Positive Endocrine-Resistant Breast Cancer," Journal of Medicinal Chemistry, vol. 63, No. 24, Nov. 2, 2020, pp. 15094-15114.

Lumachi et al., "Current Medical Treatment of Estrogen Receptor-Positive Breast Cancer," World Journal of Biological Chemistry, vol. 6, No. 3, Aug. 26, 2015, pp. 231-239.

McDonnell et al., "Oral Selective Estrogen Receptor Downregulators (SERDs) a Breakthrough Endocrine Therapy for Breast Cancer," Journal of Medicinal Chemistry, vol. 58, No. 12, Jun. 25, 2015, 10 pp.

Ohnsorg et al., "Bottlebrush Polymer Excipients Enhance Drug Solubility: Influence of End-Group Hydrophilicity and Thermoresponsiveness," ACS Macro Letters, vol. 10, Mar. 2021, pp. 375-381.

Ohnsorg et al., "Tuning PNIPAm Self-Assembly and Thermoresponse: Roles of Hydrophobic End-Groups and Hydrophilic Comonomer," Polymer Chemistry, May 2019, 11 PP.

Osborne et al., "Fulvestrant: an Oestrogen Receptor Antagonist with a Novel Mechanism of Action," British Journal of Cancer, 90 Suppl 1(Suppl 1), Mar. 2004, pp. S2-S6.

Patel et al., "Selective Estrogen Receptor Modulators (SERMs) and Selective Estrogen Receptor Degraders (SERDs) in Cancer Treatment," Pharmacology & Therapeutics, vol. 186, Jun. 2018, 24 pp.

Quirke, "Tamoxifen from Failed Contraceptive Pill to Best-Selling Breast Cancer Medicine: A Case-Study in Pharmaceutical Innovation," Frontiers in Pharmacology, vol. 8, No. 620, Sep. 2017, 16 pp.

Ricarte et al., "Direct Observation of Nanostructures during Aqueous Dissolution of Polymer/Drug Particles," Macromolecules, vol. 50, No. 8, Apr. 2017, pp. 3143-3152.

Ricarte et al., "Recent Advances in Understanding the Micro- and Nanoscale Phenomena of Amorphous Solid Dispersions," Molecular Pharmaceutics, vol. 16, No. 10, pp. 4089-4103.

Robertson et al., "Fulvestrant 500 mg Versus Anastrozole 1 mg for Hormone Receptor-Positive Advanced Breast Cancer (FALCON): an International, Randomised, Double-Blind, Phase 3 Trial," The Lancet, vol. 388, Dec. 2016, pp. 2997-3005.

Stockmayer et al., "Effects of Polydispersity, Branching and Chain Stiffness on Quasielastic Light Scattering," Pure and Applied Chemistry, vol. 54, No. 2, 1982 (Applicant points out, in accordance with MPEP 609.04(a), that the year of publication, 1982, is sufficiently earlier than the effective U.S. filing date, so that the particular month of publication is not in issue.) pp. 407-414.

Taylor et al., "Physical Chemistry of Supersaturated Solutions and Implications for Oral Absorption," Advanced Drug Delivery Reviews, vol. 101, Jun. 1, 2016, pp. 122-142.

Ting et al., "Advances in Polymer Design for Enhancing Oral Drug Solubility and Delivery," Bioconjugate Chemistry, vol. 29, No. 4, Jan. 10, 2018, pp. 939-952.

Ting et al., "High-Throughput Excipient Discovery Enables Oral Delivery of Poorly Soluble Pharmaceuticals," ACS Central Science, vol. 2, No. 10, Oct. 12, 2016, pp. 748-755.

Van Zee et al., "Role of Polymer Excipients in the Kinetic Stabilization of Drug-Rich Nanoparticles," ACS Applied Bio Materials, vol. 3, No. 10, Oct. 7, 2020, pp. 7243-7254.

Wu et al., "Structural Basis for an Unexpected Mode of SERM-Mediated ER Antagonism," Molecular Cell, vol. 18, May 13, 2005, pp. 413-424.

Wu et al., "Thermodynamically Stable Globule State of a Single Poly (N-isopropylacrylamide) Chain in Water," Macromolecules, vol. 28, No. 15, Jul. 1, 1995, pp. 5388-5390.

\* cited by examiner

MACROMONOMERS AND BOTTLE BRUSH POLYMERS FOR DELIVERY OF BIOLOGICAL AGENTS

This application claims the benefit of U.S. Provisional Application No. 63/199,785, filed Jan. 25, 2021, the entire content of which is herein incorporated by reference.

BACKGROUND

Macromolecular excipients have been used to sequester small molecules and larger drug payloads such as active pharmaceutical ingredients (APIs), proteins, and polynucleotides. In oral, intravenous, or intramuscular administration, the polymer works with the biologically active agent as a stabilizer. Some common classes of linear polymers used as excipients include, for example, cellulose-derivatives, pyrrolidones, polyethylene oxide), and poly(acrylic acid). Tactics to further increase excipient efficacy generally rely on improving the rate of dissolution, self-assembly, and colloidal stability of drug-rich nanoparticles, which form during the dissolution process.

A macromolecule with a bottlebrush architecture can include polymeric side chains grafted to, from, or through a polymer backbone to form comb, globular, or worm-like morphologies. Ring-opening metathesis polymerization (ROMP) of norbornene functionalized macromonomers (MMs) provides an efficient route to design globular macromolecular structures having densely-packed side chains with diverse compositions. Bottlebrush polymers provide a well-defined and tunable synthetic platform, offering control over the density, monomer composition, and conformation of the side chains, and can be used in therapeutic drug delivery. Therapeutics and imaging labels can be covalently attached to bottlebrush architectures using established coupling chemistries to achieve controlled release in the body or in a cell in the presence of the appropriate stimulus.

SUMMARY

Biological molecules can be covalently conjugated to polymeric macromolecules to form delivery vehicles that are used to target a specific cell type or portion of the body. In contrast, the present disclosure is generally directed to macromolecules and bottlebrush polymers that can interact non-covalently with biological agents to provide highly tunable, multivalent vehicles to enhance solubility, release, and/or delivery of the biological agents. The use of non-covalent sequestration techniques can provide a delivery vehicle that interacts with a wider variety of biological agents, and can potentially target a wider variety of cells, organs or tissues.

The macromolecules and bottlebrush polymers of the present disclosure have a backbone and side chains with a monomeric units selected to enable an excipient to stabilize a selected biological agent for at least one of oral, intravenous, or intramuscular administration, both on the shelf and in vivo. The macromolecules and bottlebrush polymers of the present disclosure have a backbone and side chains with a polymeric and functional end group composition selected to physically sequester and solubilize hydrophobic pharmaceuticals. In some examples, the macromolecules and bottlebrush polymers of the present disclosure form globular or micelle-like nanoparticles that are well-defined monodisperse unimers in solution, and do not require self-assembly into complex structures to effectively sequester biologically active compounds.

In one example, functional groups on the backbone and arms of the macromolecules and bottlebrush polymers can be selected to control the hydrophilicity of the polymers and enhance their solubility when used as an excipient for a selected biologically active agent. In some examples, the macromolecules and bottlebrush polymers of the present disclosure have side chains that were particularly effective at stabilizing a biological agent at high loadings of up to about 25 weight percent (wt %).

In some embodiments, the macromolecules and bottlebrush polymers of the present disclosure provide a polymerically configurable architecture to non-covalently physically encapsulate hydrophobic small biologically active molecules. In one example, although oral drug delivery is the most common form of medication administration, over 60% of APIs in the pharmaceutical pipeline are impacted by gastrointestinal track insolubility. Such APIs are categorized by the Biopharmaceutical Classification System (BCS) as Class H and can be solubilized with polymer excipients using a polymer-amorphous spray-dried dispersion (PASD) in which the amorphous API is suspended in a polymer matrix facilitating rapid dissolution and sustained solubility in aqueous media. The macromolecules and bottlebrush polymers of the present disclosure can be chemically configured to physically sequester and solubilize such medications, which can provide the medications with adequate permeability across the epithelial lining. Providing epithelial permeability of new and different classes of medications can potentially provide a wide range of entirely new and useful drug therapies.

In one aspect, the present disclosure is directed to a composition including: a macromolecular polyacrylamide copolymer excipient with an α-end including a ROMP-active norbornene end-group and a ω-end including a terminal monomer with an end group chosen from: a hydrogen atom (H); or a functionalized acrylate with functionality chosen from alkyl, hydroxyl (OH), methyl-polyethylene glycol ((PEG)-$CH_3$), hydroxy-PEG (PEG-OH), carboxylic acid (COOH), and combinations thereof; and a biological compound non-covalently hound with the macromolecular excipient, wherein the biological compound is chosen from active pharmaceutical ingredients, proteins, polynucleotides, and mixtures and combinations thereof.

In another aspect, the present disclosure is directed to a composition including: an excipient with a bottle-brush morphology, wherein the excipient includes a backbone polymer derived from norbornene and a plurality of filamentous arms attached to the backbone polymer, wherein the arms include a polyacrylamide copolymer, the polyacrylamide copolymer including a terminal monomer with an end group chosen from: a hydrogen atom (H); or a functionalized acrylate with functionality chosen from alkyl, hydroxyl (OH), methyl-polyethylene glycol ((PEG)-$CH_3$), hydroxy-PEG (PEG-OH), carboxyl (COOH), and combinations thereof and a biological compound non-covalently bound with the excipient, wherein the biological compound is chosen from active pharmaceutical ingredients, proteins, polynucleotides, and mixtures and combinations thereof.

In another aspect, the present disclosure is directed to a method for making a delivery system for a biological compound, the method including: grafting norbornene functionalized polyacrylamide copolymers together to form a supramolecular macromolecule with the terminal functional group on each arm radiating from the grafted polynorbornene derived backbone comprising an alkyl trithiocarbonate compound; and reacting the alkyl trithiocarbonate on the macromolecule to form an excipient for the biological compound having a modified functional group, wherein the modified functional group is chosen from: a completely removed trithiocarbonate group resulting in a hydrogen atom (H), and a functionalized acrylate with functionality chosen from alkyl, hydroxyl (OH), methyl-polyethylene glycol ((PEG)-CH$_3$), hydroxy-PEG (PEG-OH), carboxyl (COOH), and combinations thereof.

In another aspect, the present disclosure is directed to a method for delivering a biological agent into a cell, the method including: providing an excipient with a bottlebrush morphology, wherein the excipient includes a backbone polymer derived from norbornene and a plurality of filamentous arms attached to the backbone polymer, wherein the arms include a polyacrylamide copolymer with terminal functionality chosen from a hydrogen atom (H) and a functional acrylate, wherein the functional acrylate includes functionality chosen from alkyl, hydroxyl (OH), methyl-polyethylene glycol (PEG-CH$_3$), hydroxy-PEG (PEG-OH), carboxyl (COOH), and combinations thereof; non-covalently associating a biological agent with the excipient, wherein the biological agent is chosen from active pharmaceutical ingredients, proteins, polynucleotides, and mixtures and combinations thereof; introducing the excipient and associated biological agent into a pharmaceutically effective liquid carrier to form a drug composition; and administering the drug composition to a patient such that the biological agent is delivered into a cell of the patient.

In another aspect, the present disclosure is directed to a method for delivering a biological agent into a cell, the method including: providing an excipient with a bottlebrush morphology, wherein the excipient includes a backbone polymer derived from norbornene and a plurality of filamentous arms attached to the backbone polymer, wherein the arms include a polyacrylamide copolymer with terminal functionality chosen from a hydrogen atom (H) and a functional acrylate, wherein the functional acrylate includes functionality chosen from alkyl, hydroxyl (OH), methyl-polyethylene glycol (PEG-CH$_3$), hydroxy-PEG (PEG-OH), carboxyl (COOH), and combinations thereof; non-covalently associating a biological agent with the excipient, wherein the biological agent is chosen from active pharmaceutical ingredients, proteins, polynucleotides, and mixtures and combinations thereof; introducing the excipient and associated biological agent into a pharmaceutically effective liquid carrier to form a drug composition; and administering the drug composition to a patient such that the biological agent is delivered into a cell of the patient.

In another aspect, the present disclosure is directed to a method of making a drug composition, the method including spray drying a biological agent chosen from active pharmaceutical ingredients, proteins, polynucleotides, and mixtures and combinations thereof with an excipient comprising a backbone polymer derived from norbornene and a plurality of filamentous arms attached to the backbone polymer, wherein the arms include a polyacrylamide copolymer with terminal functionality chosen from a hydrogen atom (H) and a functionalized acrylate with functionality chosen from alkyl, hydroxyl (OH), methyl-polyethylene glycol ((PEG)-CH), hydroxy-PEG (PEG-OH), carboxyl (COOH), and combinations thereof.

The details of one or more embodiments of the invention are set forth in the accompanying drawings and the description below. Other features, objects, and advantages of the invention will be apparent from the description and drawings, and from the claims.

BRIEF DESCRIPTION OF DRAWINGS

(FIG. 9D), -PEG-OH (FIG. 9E), -tButyl (FIG. 9F), and —COOH (FIG. 9G). The samples were 9 mg/mL in PBS (pH 6.5) measured at both 25 (dotted lines) and 37 (solid lines) ° C.

Like symbols in the drawings indicate like elements.

DETAILED DESCRIPTION

Figure 1A:
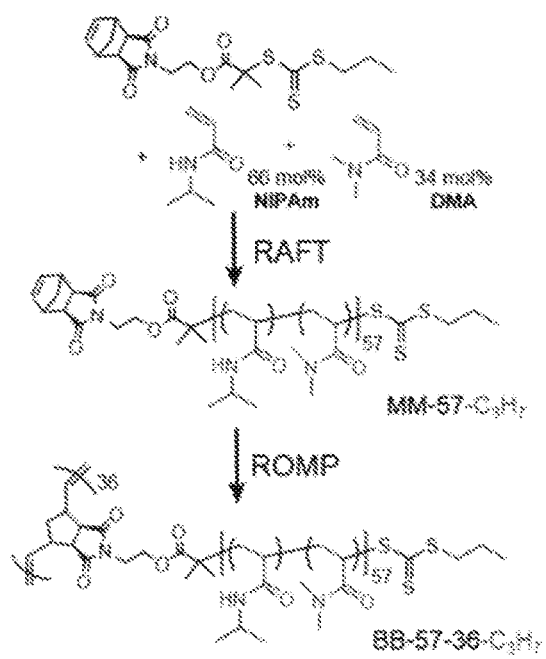
FIG. 1A is a schematic representation of an embodiment of a synthetic scheme for preparing an example macromolecule MM-57-C$_3$H$_7$ according to the present disclosure using reversible addition-fragmentation chain transfer (RAFT) polymerization to synthesize a polyacrylamide copolymer with a ring-opening metathesis polymerization (ROMP) active R-group facilitated through use of a norbornene functionalized trithiocarbonate compound and a propyl Z-group. The RAFT polymerization step is followed by optional ROMP that grafts the norbornyl functional ends of the macromolecule MM-57-C$_3$H$_7$ together to form an example bottlebrush polymer BB-57-36-C$_3$H$_7$.

In one embodiment, the present disclosure is directed to a composition including a macromolecular excipient and a biopharmaceutical compound non-covalently bound with the macromolecular excipient. Referring now to FIG. 1A, the macromolecular excipient is synthesized by polymerizing a copolymer using a trithiocarbonate chain transfer agent (CTA) functionalized at a first (α) end with a strained ring structure and a second (ω) end with an alkyl terminal Z-group.

The terminal functionality on the first end of the trithiocarbonate chain transfer agent (sometimes referred to as the R-group) is selected to be polymerizable in subsequent reaction steps using a ring-opening metathesis polymerization (ROMP) process. The first end functionality can vary widely depending on the intended application of the macromolecule or bottlebrush polymer. In the exemplary embodiment of FIG. 1A, which is not intended to be limiting, the first end of the trithiocarbonate compound includes a polymerizable norbornene chain end. In some examples which are not intended to be limiting, the ring of the norbornene may optionally be substituted with a carboxylic acid, a dicarboxylic acid anhydride, a dicarboxylic acid imide, or an alcohol such as methanol, ethanol and the like.

The second end of the trithiocarbonate compound includes a terminal alkyl group, which may be linear or branched, and may include about 2 to about 18 carbon atoms. In some examples, the alkyl group is propyl ($C_3H_7$) may be used to initially reduce the hydrophobic contribution of the end groups in subsequent reaction steps in which the terminal groups are modified to add functionality selected to physically sequester a desired biopharmaceutical compound.

Referring again to FIG. 1A, hydrophilic and thermally responsive monomeric units are polymerized into the functionalized trithiocarbonate CTA using a reversible addition-fragmentation chain transfer (RAFT) polymerization step to form a generally linear macromolecule referred to therein as MM-57-$C_3H_7$. In the RAFT polymerization method, the CTA can be used to "control" the reactivity of and shuttle the radical between an active and dormant state during the polymerization facilitating greater control over the resulting polymer's dispersity and composition in comparison to a free radical polymerization process. There are many types of reversible deactivation radical polymerizations (RDRPs) like atom-transfer radical polymerization and nitroxide mediated polymerization, but RAFT is preferred for its use of the CTA to achieve the reversible deactivation of the radical needed to give "control" to the polymerization. The CTA then also imparts two functional end groups (R and Z-group that can either be functionalized pre- or post-polymerization.

The selection of monomeric units to be polymerized via RAFT using a norbornene functionalized trithiocarbonate CTA can vary widely, but polyacrylamides have been found to be particularly suitable due to the R-group structure of the CTA prior to norbornene functionalization shown in FIG. 1A. In the example of FIG. 1A, an acrylamide copolymer including poly(N-isopropylacrylamide-stat-N,N-dimethyl-acrylamide) (poly(NIPAm-stat-DMA) or PND) were selected to interact with rapidly crystallizing small molecule therapeutics. Polyacrylamides such as poly(NIPAm-stat-DMA) have been demonstrated to balance at least three synergistic effects: (i) inhibition of crystallization by NIPAm repeat units, (ii) enhanced solubility imparted by the DMA at a desired ratio NIPAm:DMA, and (iii) formation of nanoaggregates that host the biopharmaceutical compound during dissolution.

The ratio of NIPAm:DMA in the grafted in portion of the macromolecule may be adjusted for a particular application, but in various examples the NIPAm:DMA molar ratio can be about 70:30 to about 60:40, or about 65:35, or about 66:34.

The side chains of the macromolecule resulting from the RAFT polymerization step may have any desired degree of polymerization from about 1 to about 100, but in various embodiments the degree of polymerization can be about 20 to about 80, or about 40 to about 60.

In various embodiments, which are not intended to be limiting and are provided by way of example, the macromolecule formed in the RAFT polymerization step has a Mn of about 1 kDa to about 50 kDa, or about 5 kDa to about 35 kDa, a cloud point ($T_{cp}$) of about 20° C. to about 35° C., and a hydrodynamic radius ($R_h$) at 25° C. of about 10 nm to about 20 nm.

Referring again to FIG. 1A, in some examples the macromolecule produced from the RAFT polymerization step may optionally be further reacted using a ring-opening metathesis polymerization (ROMP) reaction that polymerizes the norbornyl functional end. In FIG. 1A, the macromolecule MM-57-$C_3H_7$ is polymerized to form an example polymer BB-57-36-$C_3H_7$ having a bottlebrush morphology.

Following the ROMP reaction, the polymerized first end of the macromolecule forms the polynorbornene backbone portion of the bottlebrush polymer. The backbone polymer portion of the bottlebrush polymer includes multiple filamentous arms covalently bonded thereto, wherein each arm includes an acrylamide copolymer with an alkyl functionalized trithiocarbonate end group.

The degree of polymerization of the backbone polymer portion of the bottlebrush polymer may vary widely depending on the intended application, and in various embodiments may range from about 2 to about 100, or about 10 to about 50, or about 20 to about 40.

In various embodiments, which are not intended to be limiting and are provided by way of example, the bottlebrush polymer formed in the ROMP reaction step has a Mn of about 200 kDa to about 300 kDa, a cloud point ($T_{cp}$) of about 20° C. to about 25° C., and a hydrodynamic radius ($R_h$) at 25° C. of about 10 nm.

Figure 1B:
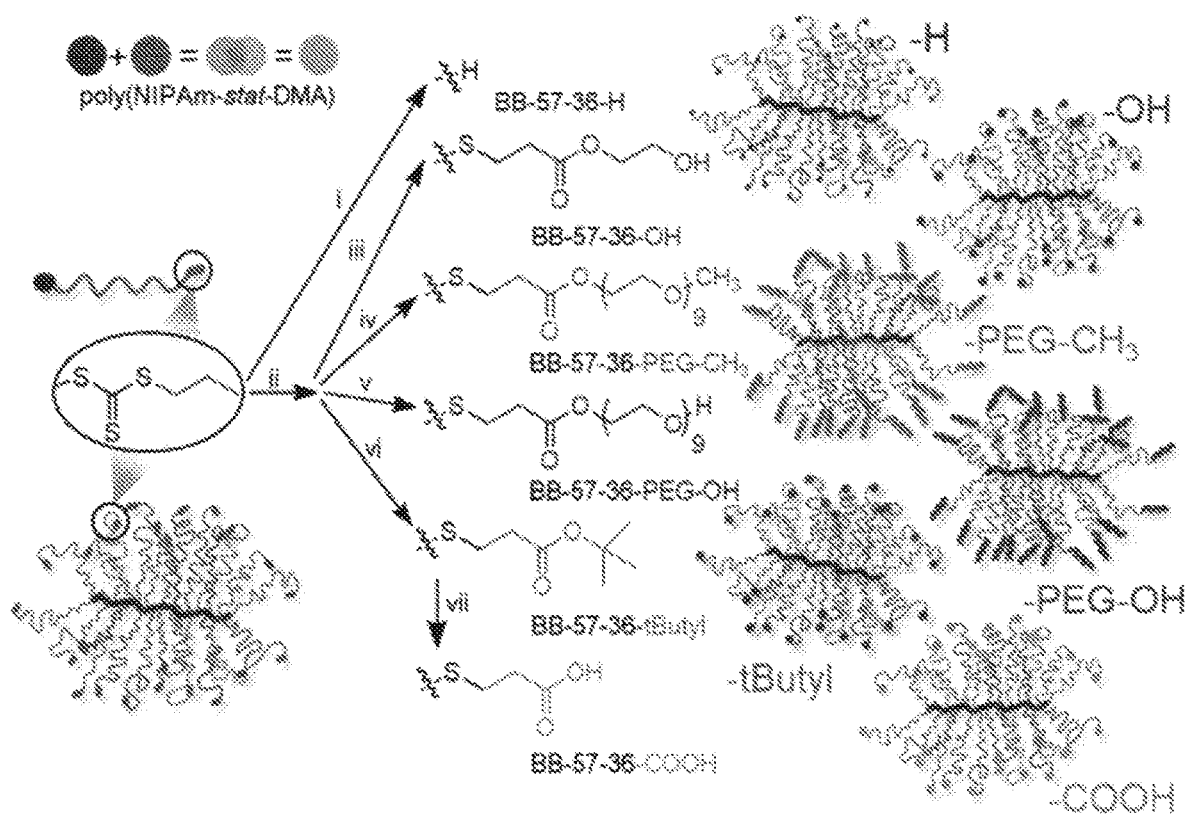
FIG. 1B is a schematic representation of embodiments of possible end-group modifications of the alkyl functional Z-group of the trithiocarbonate on the macromolecule MM-57-C$_3$H$_7$ following the RAFT polymerization step, or of the bottlebrush polymer BB-57-36-C$_3$H$_7$ following the ROMP step.

Referring now to FIG. 1B, the alkyl functional ($C_3H_7$) terminal group on the trithiocarbonate of the macromolecule MM-57-$C_3H_7$, or on the side chains of the bottlebrush polymer BB-57-36-$C_3H_7$, may be modified to form a wide variety of excipients configured to non-covalently physically sequester a desired bioactive compound. In the process schematically illustrated in FIG. 1B, which is not intended to be limiting, in one example the trithiocarbonate end-group may be removed completely using photoinduced chain transfer in the presence of a proton donor (H). In another example, thia-Michael addition may be used to install a spectrum of functionalized acrylates yielding the following end-groups: hydroxyl (—OH), methyl-PEG (-PEG-$CH_3$), hydroxy-PEG (-PEG-OH), tert-butyl (-tButyl), and carboxyl (—COOH).

As shown schematically in FIG. 1B, the bottlebrush polymers include a polymeric backbone polymer derived from the norbornene functionalized end of the RAFT polymerized macromolecule, and the polyacrylamide copolymers with alkyl functional thiocarbonates form a plurality of filamentous polymeric arms extending outwardly in all directions from the backbone polymer. While FIG. 1B depicts the bottlebrush polymers extending in two dimensions, the arms form a three-dimensional structure and extend in multiple planes from the backbone polymer.

Selected properties of the functionalized macromolecules and bottlebrush polymers are shown in Table 1.

In Table 1, samples 1-5 represent linear copolymeric NIPAm:DMA (PND) comparative controls polymerized via RAFT with four distinct chain transfer agents (CTAs): (1) propionic acid(PA)-PND-245-$C_3H_7$, (2) PA-PND-61-$C_3H_7$, (3) PA-PND-62-$C_{12}H_{25}$, (4) cyano-acid(CA)-PND-62-$C_{12}H_{25}$, and (5) cyano-propyl(CP)-PND-72-$C_{12}H_{25}$.

TABLE 1

| Sample | mol %$^a$ (N/D) | $M_n^b$ (kDa) | $M_{w,SEC}^b$ (kDa) | Đ$^b$ | $T_{cp}^c$ (°C.) | $R_{h, 25°C.}^d$ (nm) | $\mu_2/\Gamma^{2,d}$ | Density$^e$ (mg/mL) |
|---|---|---|---|---|---|---|---|---|
| 1 PA—PND-245-C$_3$H$_7$ | 65/35 | 31$^\dagger$ | 30 | 1.11 | 39 | 5.5, 34.0 | 0.29, 0.22 | — |
| 2 PA—PND-61-C$_3$H$_7$ | 66/34 | 7.3$^\dagger$ | 7.0 | 1.02 | 44 | 2.5 | 0.18 | — |
| 3 PA—PND-62-C$_{12}$H$_{25}$ | 66/34 | 7.1$^\dagger$ | 7.2 | 1.02 | 50 | 7.4$^\ddagger$ | 0.21$^\ddagger$ | 80$^{40}$ |
| 4 CA—PND-62-C$_{12}$H$_{25}$ | 66/34 | 7.0$^\dagger$ | 7.2 | 1.02 | 51 | 7.2 | 0.12 | — |
| 5 CP—PND-72-C$_{12}$H$_{25}$ | 64/36 | 9.0$^\dagger$ | 8.3 | 1.02 | 38 | 7.9 | 0.04 | — |
| MM-57-C$_3$H$_7$ | 66/34 | 6.2$^\dagger$ | 6.9 | 1.04 | 31 | 1.6 | 0.11 | — |
| BB-57-36-C$_3$H$_3$ | 66/34 | 240 | 280 | 1.15 | 22 | 9.5*$^{,\ddagger}$ | 0.11*$^{,\ddagger}$ | 105* |
| MM-57-H | 66/34 | 6.3 | 6.6 | 1.04 | 37 | 2.7, 11.7 | 0.29, 0.22 | — |
| BB-57-36-H | 66/34 | 230 | 260 | 1.15 | 35 | 9.6$^\ddagger$ | 0.07$^\ddagger$ | 101 |
| MM-57-OH | 66/34 | 6.4 | 6.7 | 1.04 | 41 | 2.6 | 0.31 | — |
| BB-57-36-OH | 66/34 | 240 | 280 | 1.19 | 35 | 10.0$^\ddagger$ | 0.09$^\ddagger$ | 91 |
| MM-57-PEG—CH$_3$ | 66/34 | 6.5 | 6.7 | 1.04 | 44 | 2.5 | 0.17 | — |
| BB-57-36-PEG—CH$_3$ | 66/34 | 240 | 290 | 1.20 | 39 | 10.0$^\ddagger$ | 0.07$^\ddagger$ | 89 |
| MM-57-PEG—OH | 66/34 | 6.6 | 7.0 | 1.05 | 43 | 2.3, 47.6 | 0.06, 0.11 | — |
| BB-57-36-PEG—OH | 66/34 | 240 | 280 | 1.15 | 39 | 9.7$^\ddagger$ | 0.13$^\ddagger$ | 99 |
| MM-57-tButyl | 66/34 | 6.3 | 6.4 | 1.03 | 38 | 2.2 | 0.22 | — |
| BB-57-36-tButyl | 66/34 | 230 | 270 | 1.15 | 29 | 9.6$^\ddagger$ | 0.07$^\ddagger$ | 100 |
| MM-57-COOH | 66/34 | 6.4 | 6.6 | 1.03 | 43 | 2.4 | 0.34 | — |
| BB-57-36-COOH | 66/34 | 230 | 250 (250$^\dagger$) | 1.07 | 42 | 9.8$^\ddagger$ | 0.08$^\ddagger$ | 96 |

In Table 1, the mol % NIPAm:DMA was determined by $^1$H NMR ratio of peak integrations for 1H at 4.00 ppm to 6H at 3.25 ppm. $^b$SEC-MALS in DMF with 0.05M LiBr $^c$Cloud point measurements determined at 80% transmittance $^d$DynaPro plate reader DLS—regularization fit (9 mg/mL) $^e$Calculated using equation S1 $^\downarrow$M$_n$ by $^1$H NMR in CDCl$_3$ *measured at 20° C. $^\ddagger$multiangle DLS $2^{nd}$ cumulant fit (1 mg/mL) $^\dagger$M$_w$ calculated by SLS.

The influence of end-group functionality on the bottlebrush (BB) polymers was assessed as a function of cloud point temperature ($T_{cp}$), solution structure, and density and compared to the linear copolymer analogues (1-5) and end-group modified macromonomers (MM) shown in Table 1.

The $T_{cp}$ of BB-57-36-C$_3$H$_7$ decreased to 22° C. due to the increased molecular weight and hydrophobic contributions from 36 propyl end-groups compared to the linear copolymer controls 1-5 ($T_{cp} \geq 38°$ C.). Because the molecular weight and composition of the side chains remained constant, Z-groups were responsible for the incremental increase in $T_{cp}$ with increasing hydrophilicity, -tButyl to —H to —OH to -PEG-CH$_3$ to -PEG-OH to —COOH, where $T_{cp}=42°$ C. for BB-57-36-COOH. Therefore, using end-group modification alone, the $T_{cp}$ of the thermoresponsive bottlebrush polymers may be adjusted over a range of 22-42° C., which can be useful for managing interactions with a selected biological compound.

Figure 2A:
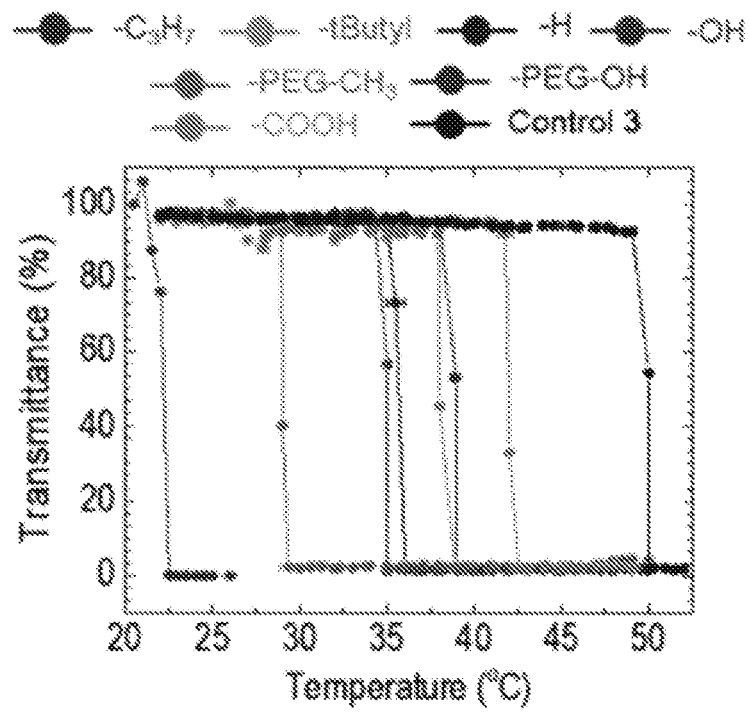
FIG. 2A is a plot of transmittance data for the end-group modified bottlebrush polymers BB-57-36-Z(Table 1) and Control 3 upon heating a 9 mg/mL sample in PBS buffer at pH 6.5.
Figure 2B:
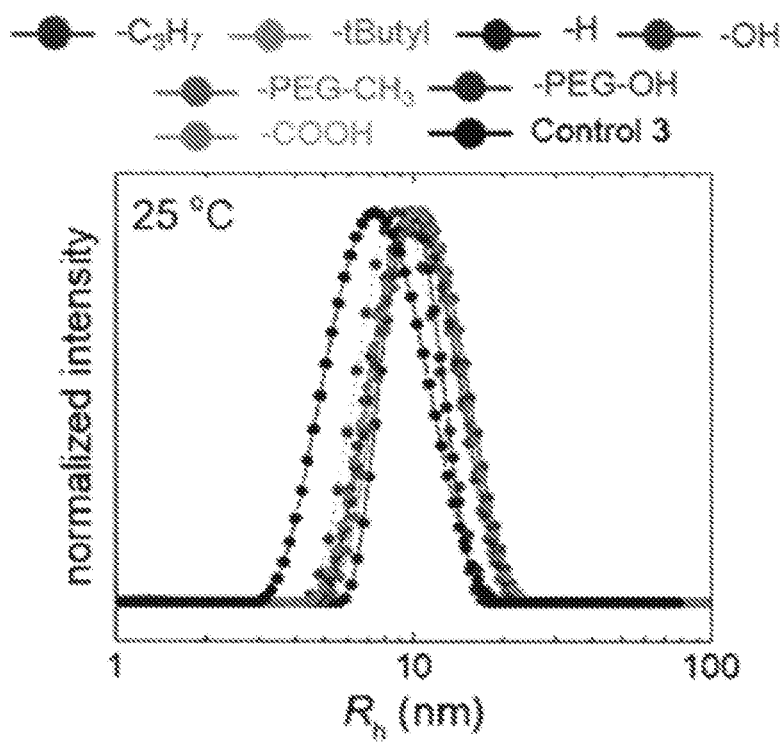
FIG. 2B is a plot of distributions of bottlebrush polymer

As shown schematically in FIG. 1B, the bottlebrush polymers of the present disclosure may be used to produce synthetically fixed unimolecular micelle-like or globular nanoparticles. The hydrodynamic radius ($R_h$) of BB-57-36-C$_3$H$_7$ was measured at 20° C. to demonstrate that, below its cloud point ($T_{cp}=22°$ C.), the particles with a $R_h=9.5$ nm did not aggregate in solution (Table 1 and FIG. 2B). Each Z-group variation of BB-57-36-C$_3$H$_7$ was measured to have a polydispersity index (PDI) less than about 0.35, or less than about 0.15, which indicated the bottlebrush polymers exist in solution as well-defined, monodisperse unimers in solution with a $R_h$=about 9 nm to about 20 nm, or about 9.6-10 nm (Table 1, FIG. 2B). These data confirm that the bottlebrush polymers were not coupled together through di-sulfide bond formation or other radical side-reactions during end-group modification. In contrast, the dodecyl Z-groups drive Control 3 to form a monomodal population of micelles with a $R_h=7.4$ nm (FIG. 2B). Therefore, Control 3 could be directly compared to the globular macromolecular bottlebrushes as a non-covalent supramolecular architecture.

Due to a $T_{cp}$ above 37° C., BB-57-36-PEG-CH$_3$, -PEG-OH, and —COOH maintained monomodal populations in solution at 37° C. with minimal change in $R_h$ from 25° C. In various embodiments, the average density ($\rho_{BB}$) of each end-group modified bottlebrush polymer can be estimated to be between 89 to 105 mg/mL (Table 1), which in some embodiments can provide a density range similar to that exhibited by micelles and crosslinked nanogels previously utilized for drug delivery. While not wishing to be bound by any theory, based on these data, an excipient utilizing the bottlebrush architecture should facilitate sustained solubilization at higher drug loading due to a high density of polymer chains promoting non-covalent associations with APIs through the polyacrylamide copolymeric NIPAm moieties.

The bottlebrush polymers of the present disclosure were utilized to non-covalently interact with a model BCS Class II API, phenytoin (PTN), an anticonvulsant on the World Health Organization's list of essential medicines (log P=2.14, $T_m$=295° C.). Each BB-57-36-Z, MM-57-Z, and Control 1-5 in Table 1 above was spray dried with 10 wt % of PTN (confirmed by synchrotron WAXS, see working examples below). The concentration of solubilized PTN in fasted-state simulated intestinal fluid (FaSSIF) during the dissolution experiment was evaluated using high-pressure liquid chromatography at 4, 10, 20, 40, 90, 180, and 360 minutes (at both 25 and 37° C.). At 37° C. (FIG. 3), the bottlebrush dissolution performance improved incrementally with increasing hydrophilicity of the Z-group (from —C$_3$H$_7$, to —COOH), mirroring the trend in $T_{cp}$ shown in FIG. 2A.

Both PEGylated bottlebrush polymers had $T_{cp}$ above 37° C. and showed burst-like release profiles. Static light scattering (SLS) measurements revealed that the second virial coefficient ($A_2$) measured at 25° C. was four times larger for BB-57-36-COOH versus BB-57-36-PEG-CH$_3$. Therefore, while not wishing to be bound by any theory, this evidence indicates that the carboxylic acid groups increased the solvent quality for this bottlebrush facilitating rapid dissolution and sustained solubility of the PASD in FaSSIF. The top performing polymer excipients were Control 3 and BB-57-36-COOH, which both solubilized amorphous API by forming ~20 nm drug-loaded particles that were stable in solution for 6 hours.

Figure 3:
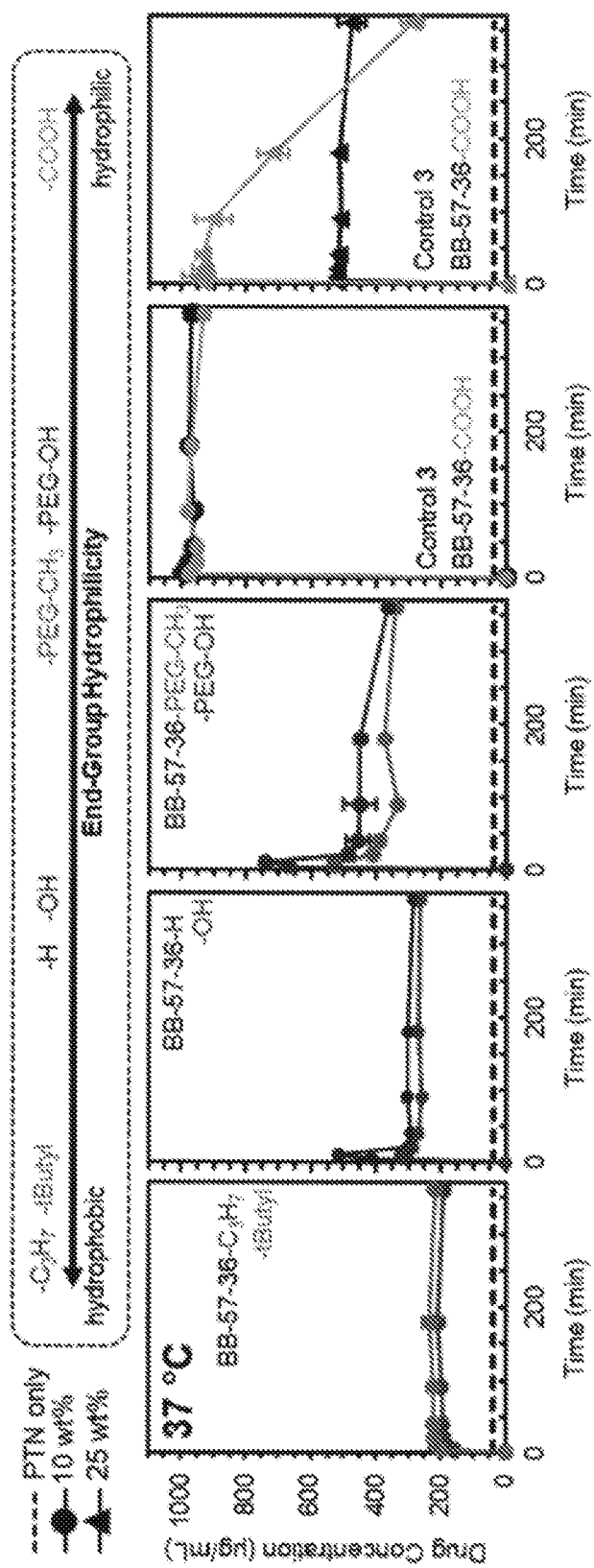

The dissolution results for Control 3 and BB-57-36-COOH with 25 wt % PTN loading at 37° C. are shown in FIG. 3. While the linear control was unable to solubilize greater than 600 µg/mL of PTN, the BB-57-36-COOH PASD fully solubilized 1000 µg/mL of PTN at 25 wt % loading for up to 90 minutes. The results summarized in FIG. 3 show that the importance of polymer architecture through tailoring the density of chains in enhancing solubility through the non-covalent sequestration of small molecule APIs. Although crystallization occurred over time due to the transition from polymer-API to API-API non-covalent interactions leading to drug crystal nucleation and growth, BB-57-36-COOH fully solubilized 1000 µg/mL of the API at early time points.

DLS studies during dissolution with 25 wt % PTN revealed that BB-57-36-COOH solubilized and stabilized amorphous PTN monomodal drug-loaded nanoparticles (~26 nm) despite slow crystallization over time. In contrast, Control 3 could not stabilize 25 wt % of PTN without significant aggregation and polymer-drug separation.

These data show that the bottlebrush polymers of the present disclosure can sequester small biologically active molecules as distinct unimolecular nanoparticles that, due to a synthetically defined density of polymer chains, are more stable in solution—despite higher loadings of hydrophobic small molecules—making them superior to linear polymer excipients.

The present disclosure is directed to the use of bottlebrush polymers for the physical sequestration and solubilization of hydrophobic pharmaceuticals enabled through post-polymerization end-group modification of a thermoresponsive bottlebrush copolymer template. While not wishing to be bound by any theory, this superior performance can be attributed to the synthetically-fixed density of bottlebrush copolymer side chains. Bottlebrush architectures can be used as vehicles for the physical encapsulation of hydrophobic small biologically active molecules and can be used for sequestration, stabilization, and delivery of these materials.

In various embodiments, the unimolecular micelle-like nanoparticles formed by the macromolecules and bottlebrush polymers of the present disclosure can facilitate intracellular delivery of the biological agent, effective protein expression and genome editing.

In various embodiments, which are not intended to be limiting, the biological compounds that can be sequestered and non-covalently bound with the macromolecules and bottlebrush polymers of the present disclosure can include active pharmaceutical ingredients (API), proteins, polynucleotides, and mixtures and combinations thereof. The biological compound or agent is non-covalently bound within the arms of the micellar macromolecules and bottlebrush polymers, which in some embodiments means that the biological compound or agent is physically entangled or sequestered within at least some of the arms of the unimolecular micellar nanoparticles formed by the macromolecules and bottlebrush polymers.

Examples of the biological compounds or agents that can be hound with the macromolecules and bottlebrush polymers include a peptide fragment, nuclease, a nucleic acid encoding a nuclease, an oligo nucleotide, an antisense oligonucleotide, a protein, peptide a DNA editing template, guide RNA, a therapeutic agent (such as, for example, a drug), a plasmid DNA encoding protein, siRNA, monoclonal antibodies, Cas9 mRNA, and mixtures and combinations thereof. In various embodiments, the micellar polymers are configured to bind with plasmid DNA (pDNA), which encode protein (fluorescence or therapeutic); pDNA encode Cas9 nuclease and/or sgRNA; mRNA that encodes for proteins (fluorescence or therapeutic), Cas9 nuclease and a separate sgRNA, or a ribonucleoprotein (RNP) that consists of recombinant Cas9 protein precomplexed directly with a sgRNA.

In various embodiments, peptide fragments include two or more amino acids covalently linked by at least one amide bond (i.e. a bond between an ammo group of one amino acid and a carboxyl group of another amino acid selected from the amino acids of the peptide fragment). The terms polypeptide and peptide fragments are used interchangeably. The term peptide fragment includes salts thereof, including pharmaceutically acceptable salts. For example, in some embodiments the peptide fragments may include pDNA encoded fluorescence or therapeutic proteins.

In various embodiments, DNA editing templates include an exogenous strand of DNA that bears homology arms to a section of genomic DNA that has been cut by a nuclease (for example, CAS9, TALEN or zinc finger) along with an intervening sequence between these homology arms that differs with the natural segment of genomic DNA that has been cut. This intervening segment serves as the template for repair of the cut genomic DNA and, in so doing, the cell corrects its own DNA to match that of the DNA template. The DNA template may be included in a single DNA expression vector that also encodes the nuclease.

The term guide RNA includes an engineered, non-naturally occurring Clustered Regularly Interspaced Short Palindromic Repeats (CRISPR) guide RNA that hybridizes with a target nucleic acid sequence of interest.

The term Cas9 mRNA includes a nucleotide sequence encoding a Type-II Cas9 protein, pDNA that encodes Cas9 protein, and pDNA that encode sgRNA. The CRISPR-Cas system is useful for precise editing of genomic nucleic acids (e.g., for creating null mutations). In such embodiments, the CRISPR guide RNA and/or the Cas enzyme may be expressed. For example, a composition containing only the guide RNA can be administered to an animal or cells transgenic for the Cas9 enzyme. Similar strategies may be used (e.g., designer zinc finger, transcription activator-like effectors (TALEs) or homing meganucleases).

The CRISPR-Cas system is known in the art for deleting, modifying genome sequences or incorporating transgenes. Transgene refers to any nucleotide sequence, particularly a DNA sequence, that is integrated into one or more chromosomes of a host cell by human intervention, such as by the methods of the present invention. For example, a transgene can be an RNA coding region or a gene of interest, or a nucleotide sequence, preferably a DNA sequence, that is used to mark the chromosome where it has integrated or may indicate a position where nucleic acid editing, such as by the CRSPR-CAS system, may occur. In this situation, the transgene does not have to include a gene that encodes a protein that may be expressed.

A gene of interest is a nucleic acid sequence that encodes a protein or other molecule, such as a RNA or targeting nucleic acid sequence, that is desirable for integration in a host cell. The gene of interest may include a 1, 2, 3, 4, 5, 6, 7, 8, 9, 10, or more genes of interest.

Genes of interest are useful for modulating the expression and/or activity of target biomolecules, either within the transduced cell or expressed for secretion outside of the transduced cell. Generally, genes of interest may be nucleic acids themselves or encode a polypeptide, a naturally-occurring binding partner of a target of interest, an antibody against a target of interest, a combination of antibodies against a target of interest and antibodies against other immune-related targets, an agonist or antagonist of a target of interest, a peptidomimetic of a target of interest, a small RNA directed against or a mimic of a target of interest, and the like. Such modulators are well known in the art and include, for example, an antisense nucleic acid molecule, RNAi molecule, shRNA, mature miRNA, pre-miRNA, pri-miRNA, miRNA, anti-miRNA, or a miRNA binding site, or a variant thereof, or other small RNA molecule such as a Piwi RNA, triplex oligonucleotide, ribozyme, coding sequence for a target of interest. Such agents modulate the expression and/or activity of target biomolecules, which includes any decrease in expression or activity of the target biomolecule of at least about 30% to about 99% or more as compared to the expression or activity of the target biomolecule which has not been targeted by a modulating agent.

In one embodiment, the gene of interest is useful for expressing and; or enhancing the activity of a nucleic acid or protein of interest. For example, the gene of interest may encode a protein or other molecule the expression of which is desired in the host cell. Such protein-encoding nucleic acid sequences are not particularly limited and are selected based on the desired exogenous perturbation desired. Thus, the gene of interest includes any gene that the skilled practitioner desires to have integrated and/or expressed. For example, exogenous expression of proteins related to autoimmune, allergic, vaccination, immunotolerance, cancer immunotherapy, immune exhaustion, immunological memory, or immunological epitope responses may be used. The gene of interest encode a protein or be a nucleic acid that serves as a marker to identify cells of interest or transduced cells. The gene of interest may encode a protein that modifies a physical characteristic of the transduced cell, such as a protein that modifies size, growth, or eventual tissue composition. In another example, the gene of interest may encode a protein of commercial value that may be harvested. Generally, the gene of interest is operatively linked to other sequences that are useful for obtaining the desired expression of the gene of interest, such as transcriptional regulator sequences like inducible promoters, as described further below.

In another embodiment, the gene of interest is useful for inhibiting the expression and/or activity of a nucleic acid or protein of interest. For example, target biomolecule expression and/or activity, such as an RNA coding region, may be reduced or inhibited using inhibitory RNAs. An RNA coding region is a nucleic acid that may serve as a template for the synthesis of an RNA molecule, such as an siRNA. RNA interference (RNAi) is an evolutionarily conserved process whereby the expression or introduction of RNA of a sequence that is identical or highly similar to a target biomarker nucleic acid results in the sequence specific degradation or specific post-transcriptional gene silencing (PTGS) of messenger RNA (mRNA) transcribed from that targeted gene (see, for example. Coburn and Cullen (2002) J. Virol. 76:9225), thereby inhibiting expression of the target biomarker nucleic acid. In one embodiment, the RNA coding region is a DNA sequence. The ability to down-regulate a target gene has many therapeutic and research applications, including identifying the biological functions of particular genes. Moreover, such inhibition may be achieved in screening assays that take advantage of pooling techniques, whereby groups of about 2 to about 100, or more, or any number or range in between, of RNA inhibitory agents are transduced into cells of interest. Suitable inhibitory RNAs include, but are not limited to siRNAs, shRNAs, miRNAs, Piwis, dicer-substrate 27-mer duplexes, single-stranded interfering RNA, and the like.

siRNAs typically refer to a double-stranded interfering RNA. In addition to siRNA molecules, other interfering RNA molecules and RNA-like molecules may be used. Examples of other interfering RNA molecules that may to inhibit target biomolecules include, but are not limited to, short hairpin RNAs (shRNAs), single-stranded siRNAs, microRNAs (miRNAs), piwiRNA, dicer-substrate 27-mer duplexes, and variants thereof containing one or more chemically modified nucleotides, one or more non-nucleotides, one or more deoxyribonucleotides, and/or one or more non-phosphodiester linkages. Typically, all RNA or RNA-like molecules that may interact with transcripts RISC complexes and participate in RISC-related changes in gene expression may be referred to as interfering RNAs or "interfering RNA molecules.

Suitable interfering RNAs may readily be produced based on the well-known nucleotide sequences of target biomolecules: In various embodiments interfering RNAs that inhibit target biomolecules may comprise partially purified RNA, substantially pure RNA, synthetic RNA, recombinant produced RNA, as well as altered RNA that differs from naturally-occurring RNA by the addition, deletion, substitution, and/or alteration of one or more nucleotides. Such alterations may include, for example, addition of non-nucleotide material, such as to the end(s) of the interfering RNAs or to one or more internal nucleotides of the interfering RNAs, including modifications that make the interfering RNAs resistant to nuclease digestion. Such alterations result in sequences that are generally at least about 80%, or more, or even 100% identical to the sequence of the target biomolecule. When the gene to be down regulated is in a family of highly conserved genes, the sequence of the duplex region may be chosen with the aid of sequence comparison to target only the desired gene. On the other hand, if there is sufficient identity among a family of homologous genes within an organism, a duplex region may be designed that would down regulate a plurality of genes simultaneously.

In another aspect, the present disclosure is directed to compositions including the unimolecular macromolecules or micellar nanoparticles described above which have been dispersed in a liquid carrier. In some embodiments, the nanoparticles may be added to the liquid carrier and stored in liquid form until needed, or alternatively may be spray dried as described above and introduced into and dispersed in the liquid carrier prior to administration to a subject.

In some embodiments the liquid carrier is a pharmaceutically acceptable carrier, which refers to a pharmaceutically-acceptable material, composition or vehicle for administration of a biological agent described herein. Pharmaceutically acceptable carriers include any and all solvents, dispersion media, coatings, antibacterial and antifungal agents, isotonic and absorption delaying agents, and the like which are compatible with the activity of the biological agent and are physiologically acceptable to the subject.

Some non-limiting examples of materials which can serve as pharmaceutically-acceptable carriers include: sugars, such as lactose, glucose and sucrose; starches, such as corn starch and potato starch: cellulose, and its derivatives, such as sodium carboxymethyl cellulose, methylcellulose, ethyl cellulose, microcrystalline cellulose and cellulose acetate; powdered tragacanth; malt; gelatin; lubricating agents, such as magnesium stearate, sodium lauryl sulfate and talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol (PEG); esters, such as ethyl oleate and ethyl laurate; agar; buffering agents, such as magnesium hydroxide and aluminum hydroxide; alginic acid; pyrogen-free water; isotonic saline; Ringer's solution; ethyl alcohol; pH buffered solutions; polyesters, polycarbonates and/or polyanhydrides; bulking agents, such as polypeptides and amino acids serum component, such as serum albumin, HDL, and LDL; C2-C12 alcohols, such as ethanol; and other non-toxic compatible substances employed in pharmaceutical formulations.

Wetting agents, coloring agents, release agents, coating agents, sweetening agents, flavoring agents, perfuming agents, preservative and antioxidants can also be present in the liquid carrier formulation.

Pharmaceutically acceptable liquid carriers can vary in a formulation described herein, depending on the administration route. The formulations described herein can be delivered to a cell or an organism via any administration mode known to a skilled practitioner. For example, the formulations described herein can be delivered in a systemic manner, via administration routes such as, but not limited to, simply applying the composition to an exterior surface of a cell, oral, intravenous, intramuscular, intraperitoneal, intradermal, and subcutaneous. In some embodiments, the compositions described herein are in a form that is suitable for injection. In other embodiments, the formulations described herein are formulated for oral administration.

In some embodiments, the liquid carrier for the nanoparticles can be a solvent or dispersing medium, containing, for example, water, cell culture medium, buffers (e.g., phosphate buffered saline), polyol (for example, glycerol, propylene glycol, liquid polyethylene glycol, and the like), suitable mixtures thereof. In some embodiments, the pharmaceutical earlier can be a buffered solution (e.g., PBS).

The formulations can also contain auxiliary substances such as wetting or emulsifying agents, pH buffering agents, gelling or viscosity enhancing additives, preservatives, colors, and the like, depending upon the route of administration and the preparation desired. Standard texts, such as "REMINGTON'S PHARMACEUTICAL SCIENCE," 17th edition, 1985, incorporated herein by reference, may be consulted to prepare suitable preparations. With respect to formulations described herein, however, any vehicle, diluent, or additive used should be biocompatible with the biological agents described herein.

The present disclosure is further directed to methods for delivering the biological agent non-covalently bonded with the macromolecules and bottlebrush polymers described above to a cell or to a subject. For example, after a composition including the micellar nanoparticles and bound biological agent payload bonded thereto is applied to the cell, the nanoparticles are delivered into the cell and the biological agent payload disassociates partially or completely therefrom, and a therapeutic amount of the biological agent takes effect therein.

In various embodiments, which are not intended to be limiting, the compositions may be administered to a cell in vitro by removing a cell from a subject, culturing the cells, applying to the cells a composition including a nanoparticle and bonded biological agent to deliver a therapeutic amount of the biological agent into at least a portion of the cells, and optionally re-introducing the cell to the subject.

In another embodiment, a tissue cell therapy technique may be used in which a tissue sample is removed from a subject, a composition including a macromolecule or a bottlebrush polymer and an non-covalently bonded biological agent is applied to the tissue to deliver a therapeutic amount of the biological agent to modify a selected cell or region of the tissue, and the modified tissue is transplanted into the subject.

In another embodiment, a composition including a macromolecule or a bottlebrush polymer and an associated biological agent is administered to a subject in vivo via oral administration or direct injection into the bloodstream such that a therapeutic amount of the biological agent is delivered into desired target cells of the subject. In various embodiments, for in vivo administration a delivery device can be used to facilitate the administration of any composition described herein to a subject, e.g., a syringe, a dry powder injector, a nasal spray, a nebulizer, or an implant such as a microchip, e.g., for sustained-release or controlled release of any formulation described herein.

The methods and compositions of the present disclosure will now be further described in the following nonlimiting examples.

EXAMPLES

Materials

The following reagents were used as received from Sigma-Aldrich, St. Louis, MO, unless otherwise noted: ethanolamine (98%), toluene, acetone, potassium phosphate tribasic (98%), propane thiol (97%), carbon disulfide ($CS_2$, 99%), 2-bromo-2-methylpropionic acid (98%), hexanes, ethyl acetate, dichloromethane, N-isopropylacrylamide (NIPAm, 97%), N,N-dimethylacrylamide (DMA, contains 500 ppm MEHQ as inhibitor, 99%) 2,2'-azobis(2-methylpropionitrile) (AIBN, 98%), 1,4-dioxane, methanol, Dichloro[1,3-bis(2,4,6-trimethylphenyl)-2-imidazolidinylidene](benzylidene)bis(3-bromopyridine)ruthenium(II) (Grubbs Catalyst M300, G3), 2-(Dodecylthiocarbonothioylthio)-2-methylpropionic acid (98%), 4-Cyano-4-[(dodecylsulfanyl-thiocarbonyl) sulfanyl]pentanoic acid (97%), 2-Cyano-2-propyl dodecyl trithiocarbonate (97%), poly(ethylene oxide) (PEG, average $M_n$=400 Da), triethylamine (≥99%), tetrahydrofuran (THF, anhydrous, contains 250 ppm BHT as inhibitor, ≥99.9%), acryloyl chloride (contains <210 ppm MEHQ as stabilizer, 97%), 1-ethylpiperidine hypophosphite (EPHP, 95%), Tris(2-carboxyethyl)phosphine hydrochloride (TCEP, powder), n-propylamine (≥99%), 2-hydroxyethyl acrylate (HEA, contains 200-650 ppm MEHQ as inhibitor, 96%), poly(ethylene glycol) methyl ether acrylate (methyl-PEGA, average $M_n$=480, contains 100 ppm BHT as inhibitor), tert-butyl acrylate (contains 10-20 ppm MEHQ as inhibitor, 98%), trifluomacetic acid (TFA, 99%), and phenytoin (99%).

N,N-dimethylacrylamide was passed through a small basic alumina column to remove inhibitor prior to use.

Cis-5-norbornene-exo-2,3-dicarboxylic anhydride (>98%) was purchased from AOKChem, Shanghai, China.

SiliaMetS-DMT was purchased from SiliCycle Inc., Quebec, Canada.

Diisopropylcarbodiimide (DIC, 97%) was purchased from Matrix Scientific, Columbia, SC.

Synthesis of (2-(1,3-dioxo-4,3,3a,4,7,7a-hexahydro-2H-4,7-methanoisoindol-2-yl)ethyl2-methyl-2-(((propylthio)carbonothioyl)thio)propanoate The synthesis of (2-(1,3-dioxo-1,3,3a,4,7,7a-hexahydro-2H-4,7-methanoisoindol-2-yl)ethyl2-methyl-2-(((propylthio)carbonothioyl)thio)propanoate is shown in the scheme below.

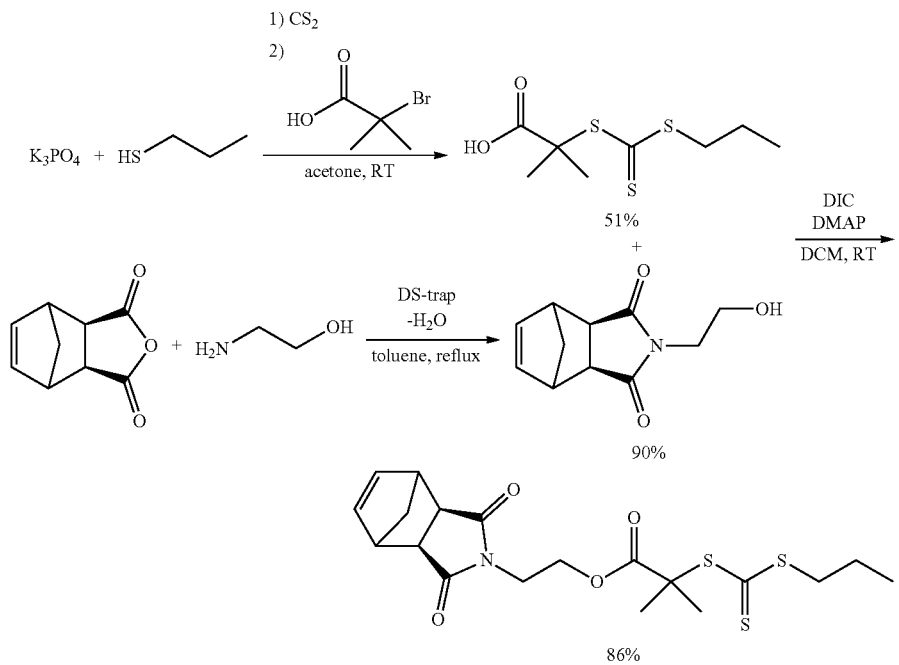

Exo-Imide Norbornene Alcohol (Yield: 90%)

Exo-carbic anhydride (9.850 g, 60.0 mmol) was charged to a 500 mL round bottom flask with 300 mL of toluene. While stirring vigorously, ethanolamine (3.8 mL, 63.0 mmol) was added dropwise to the reaction mixture. After 25 hours at reflux conditions with a Dean-Stark trap, the reaction mixture was removed from heat. The toluene was removed under rotary evaporation and an off-white crystalline solid was collected as pure product (11.15 g, 90% yield). $^1$H NMR (500 MHz, CDCl$_3$) δ 6.30 (s, 1H), 3.79 (t, J=4.6 Hz, 2H), 3.71 (t, J=5.0 Hz, 2H), 3.29 (s, 2H), 2.72 (s, 2H), 2.09 (s, 1H), 1.53 (d, J=9.8 Hz, 1H), 1.35 (d, J=10.2 Hz, 1H). $^{13}$C NMR (500 MHz, CDCl$_3$) δ 178.8, 137.9, 60.7, 45.3, 42.8, 41.4.

2-(propylocarbonothioylthio)-2 methyl Propionic Acid (Yield: 51%)

Potassium phosphate tribasic (13.9880 g, 65.9 mmol) was dissolved in a 500 mL round bottom flask with 200 mL of acetone. The reaction mixture was purged for 5 min with N$_2$(g). Propane thiol (6.1 mL, 65.9 mmol) was added dropwise to the reaction mixture while stirring. After 10 minutes, carbon disulfide (10.7 mL, 177.9 mmol) was added dropwise to the reaction mixture and stirred for 20 minutes. To add the 2-bromo-2-methylpropionic acid (12.1040 g, 72.5 mmol) the reaction flask was opened to atmosphere. The reaction flask was then re-sealed and stirred for 24 hours at room temperature. After 24 hours, the reaction was orange in color with solid precipitate. The salt precipitate was removed via vacuum filtration and rinsed with acetone. The filtrate was concentrated using rotary evaporation to a dark orange oil. The oil was diluted with 100 mL of DCM and rinsed with 300 mL of 1N HCl. The aqueous layer was extracted 3 times with 100 mL of DCM which was washed with 100 mL of ultra-pure water two times. The organic layer was dried over magnesium sulfate and concentrated under rotary evaporation. Product was isolated on a silica gel column, eluting with 4:1 hexanes-ethyl acetate, to give 7.94 g of pure product as a yellow solid (51% yield). $^1$H NMR (500 MHz, CDCl$_3$) δ 3.28 (t, J=7.3 Hz, 2H), 1.73 (s, 8H), 1.01 (t, J=7.4 Hz, 3H). $^{13}$C NMR (500 MHz, CDCl$_3$) δ 178.2, 60.5, 55.6, 38.9, 25.2, 24.2, 21.4, 13.5.

(2-(1,3-dioxo-1,3,3a,4,7,7a-hexahydro-2H-4,7-methanoisoindol-2-yl)ethyl2-methyl-2-(((propylthio)carbonothioyl)thio)propanoate (NB-CTA) (yield: 86%)

2-(propylthiocarbonothioylthio)-2 methyl propionic acid (7.49 g, 33.33 mmol), 4 dimethylaminopyridine (0.339 g, 2.77 mmol) and exo-imide norbornene alcohol (5.80 g, 27.75 mmol) was charged to a 1 liter round bottom with 300 mL of dichloromethane. The reaction mixture was purged with N2 (g) for 30 minutes prior to adding diisopropylcarbodiimide (5.6 mL, 36.08 mmol) dropwise to the reaction mixture. The reaction was stirred under a static N2 atmosphere overnight. The reaction mixture was filtered to remove the urea precipitate. The crude product was purified on a neutral alumina column eluting with 5:1 hexanes:ethyl acetate to isolate the coupled product (10.4 g, 86% yield) which was dried under vacuum to yield a yellow solid. $^1$H NMR (500 MHz, CDCl$_3$) δ 6.28 (s, 2H), 4.26 (t, J=5.3 Hz, 2H), 3.77 (t, J=5.2 Hz, 2H), 3.27 (s, 3H), 3.23 (t, J=7.4 Hz, 2H), 2.69 (s, 2H), 1.73-1.63 (m, 8H), 1.52 (d, J=10.0 Hz, 1H), 1.30 (d, J=9.8 Hz, 1H), 0.99 (t, J=7.4 Hz, 3H). $^{13}$C NMR (500 MHz, CDCl$_3$) δ 177.7, 137.8, 62.3, 61.1, 55.6, 47.9, 45.3, 42.9, 41.2, 38.8, 37.4, 25.1, 24.6, 21.4, 13.5.

Synthesis of exo-norbornene imide-PND-57-$C_3H_7$ (MM-57-$C_3H_7$)

The synthesis of exo-norbornene imide-PND-57-$C_3H_7$ (MM-57-$C_3H_7$) is shown in the Scheme below.

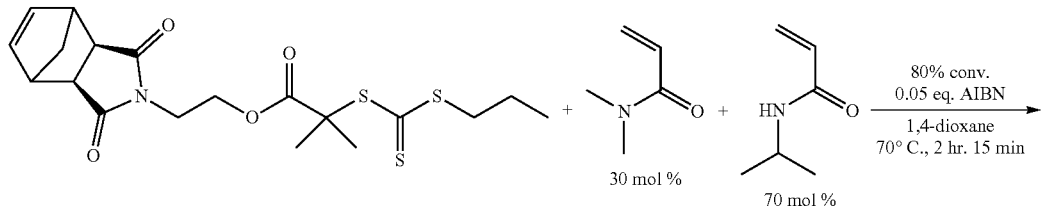

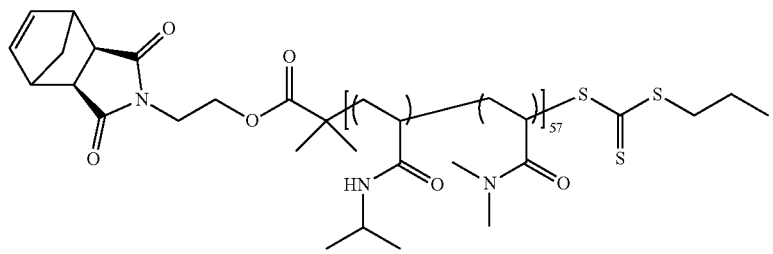

A representative polymerization procedure is as follows: NB-CTA (1.60 g, 3.74 mmol), N-isopropylacrylamide (15.84 g, 140.0 mmol), N,N-dimethylacrylamide (6.31 mL, 60.0 mmol), and AIBN (30.7 mg, 0.187 mmol) were dissolved in 200 mL of 1,4-dioxane. The reaction mixture was purged with N2 gas for 90 minutes before stirring for 2 hours and 15 minutes at 70° C. (approx. 80% conv.). The reaction was quenched in liquid nitrogen and opened to air. Polymer was purified by dialysis (1 kDa RC dialysis tubing) in methanol and characterized via 1H NMR in $CDCl_3$ and SEC-MALS (DMF with 0.05 M LiBr).

Synthesis of the Bottlebrush Copolymer Scaffold via ROMP

The synthesis of BB-57-36-$C_3H_7$ is shown in the scheme below:

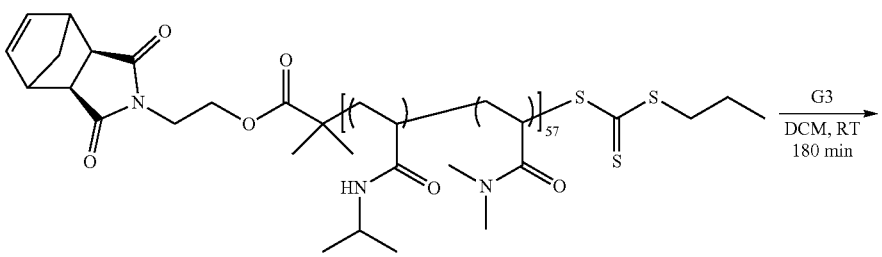

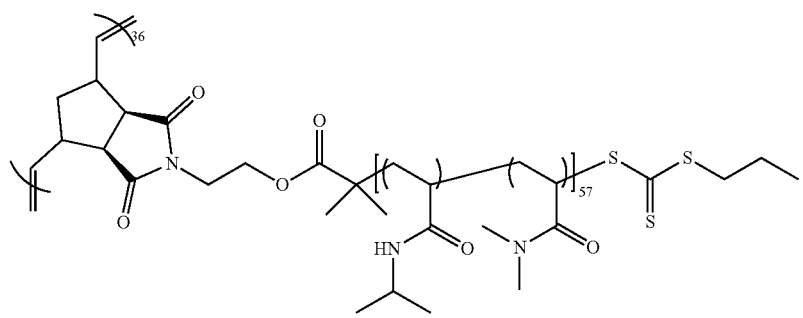

MM-57-C$_3$H$_7$ (9.95 g, 1.5 mmol) was dissolved in anhydrous DCM (30 mL, 0.05 M) under N$_{2(g)}$ atmosphere in a glove box. A stock solution (60 mg/mL) of G3 in anhydrous DCM was prepared, and 890 μL of the stock was added to the vigorously stirring macromonomer solution. An immediate color change was observed of the catalyst from green to brown. The reaction was stirred at room temperature for 3 hours and quenched with ethyl vinyl ether and exposed to air. The diluted reaction mixture was stirred with SiliaMetS-DMT to remove the Ru catalyst and filtered to remove the silica particles. The bottlebrush was further purified by dialysis (12-14 kDa RC dialysis tubing) in methanol. The bottlebrush polymer was characterized using $^1$H NMR in CDCl$_3$ and by SEC-MALS (DMF with 0.05 M LiBr).

End-Group Modification Procedures

Figure 4:
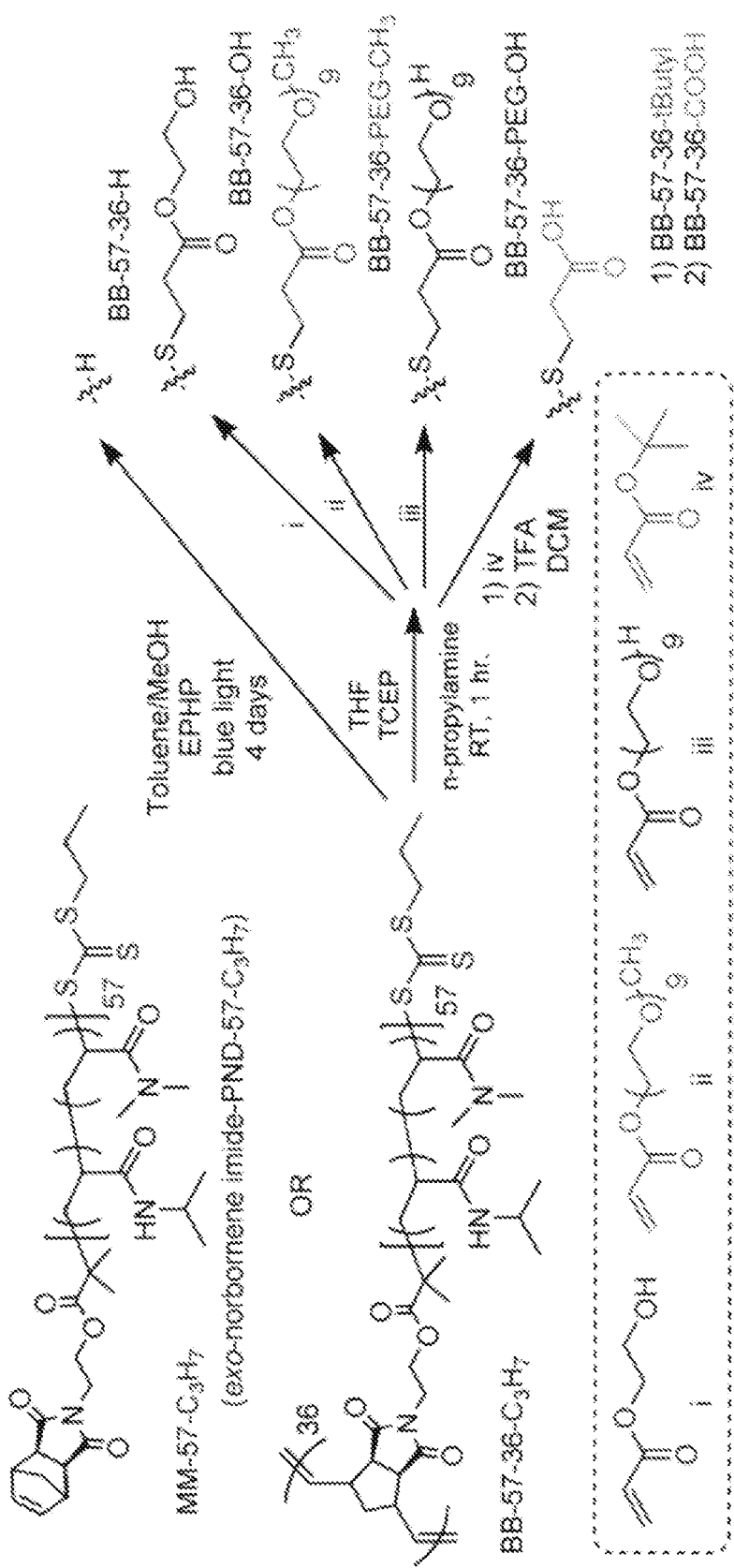

Post polymerization end-group modification of both the macromonomers and bottlebrushes were conducted through photoinitiated end-group cleavage with blue light (450-470 nm) or aminolysis followed by Michael addition of: (i) hydroxyethyl acrylate, (ii) polyethylene glycol) methyl ether acrylate, (iii) polyethylene glycol) hydroxy ether acylate, or (iv) tort-butyl acrylate. The end group modification procedures are shown in the schemes set forth in FIG. 4.

Photoinitiated Trithiocarbonate Cleavage: MM-57-C$_3$H$_7$ or BB-57-36-C$_3$H$_7$ was dissolved in a mixture of toluene and methanol (70:30) and EPHP (30 eq. to each Z-group). After the reaction mixture was purged with N$_{2(g)}$ for 30 minutes, the reaction mixture was stirred at room temperature while irradiating with blue light (450-470 nm) for 4 days or until the reaction mixture was colorless. The colorless reaction mixture was purified by dialysis in methanol.

Thio-Michael Addition End-Group Modification: MM-57-C$_3$H$_7$ or BB-57-36-C$_3$H$_7$ was dissolved in THF (0.1 M) with TCEP (1 eq. to each Z-group). The solution was degassed with N$_{2(g)}$ for 15 minutes before n-propylamine (50 eq. to each Z-group) was added dropwise to the solution. The solution was stirred at room temperature for 1 hour. After only 20 minutes, the reaction mixture was colorless. After 1 hour, acrylate [hydroxy-ethyl acrylate (50 eq. to each Z-group), poly(ethylene glycol) methyl ether acrylate (25 eq. to each Z-group), polyethylene glycol) methyl ether acrylate (25 eq. to each Z-group), tert-butyl acrylate (25 eq. to each Z-group)] was added dropwise to the reaction mixture and the reaction was stirred at room temperature overnight (14 hours) The reaction mixture was purified by dialysis in methanol. The tert-butyl group was removed by stirring MM-57-tButyl or BB-57-36-tButyl in DCM (0.01 M) with TFA (200 eq. for the MM end group cleavage and 15 eq. per Z-group for the BB) for 5 hours. The DCM and TFA was removed by rotary evaporation with a base trap and further purified by dialysis in methanol.

Synthesis of Copolymer Controls

Five linear statistical copolymer controls were synthesized via RAFT polymerization with four different chain transfer agents. The general schemes are summarized in FIG. 5.

Figure 5A:
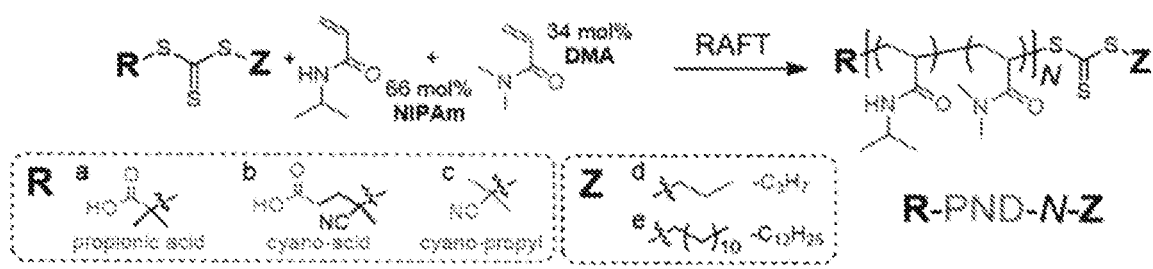
Figure 5B:
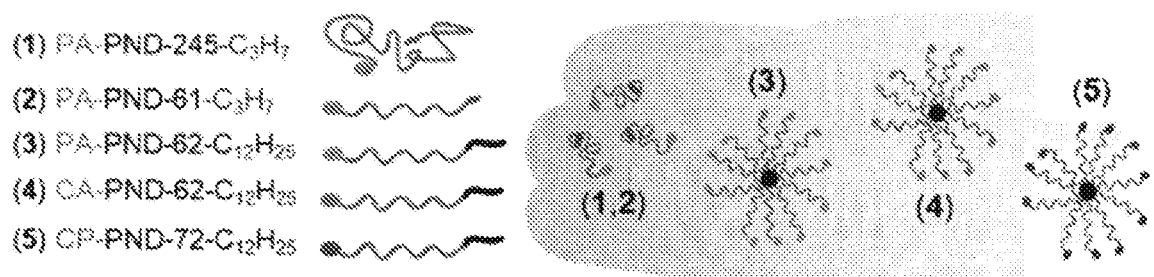
Figure 6A:
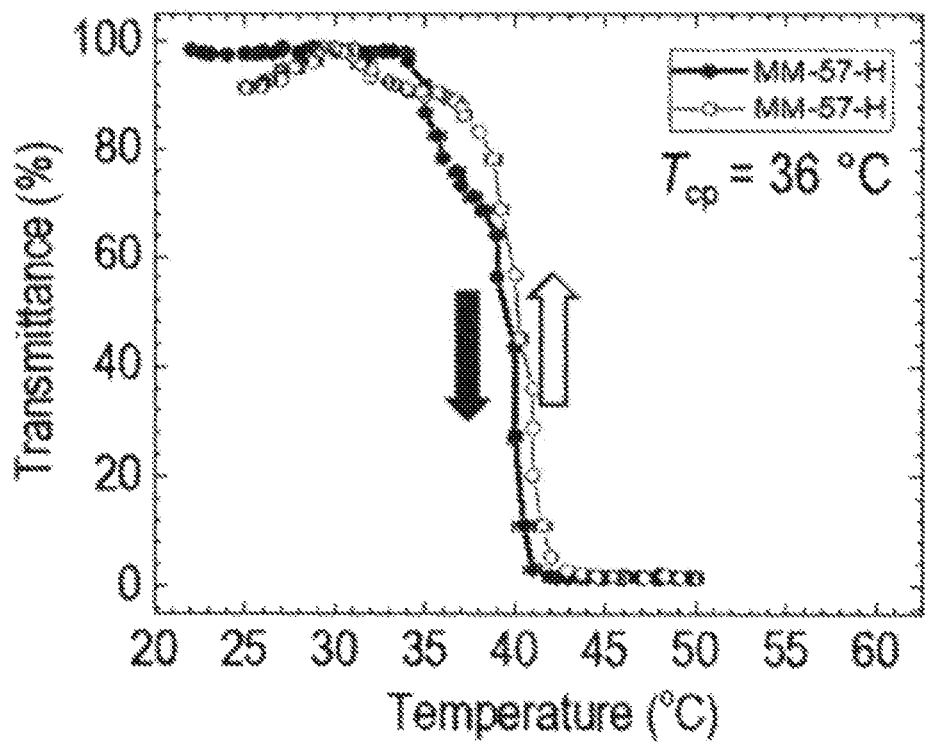
FIG. 6C includes a series of plots of transmission data upon heating (closed dots) and cooling (open dots) of all end-group modified MM-57-PEG-CH$_3$ in PBS pH 6.5 at 9.0 mg/mL.
FIG. 6D includes a series of plots of transmission data upon heating (closed dots) and cooling (open dots) of all end-group modified MM-57-PEG-OH in PBS pH 6.5 at 9.0 mg/mL.
FIG. 6E includes a series of plots of transmission data upon heating (closed dots) and cooling (open dots) of all end-group modified MM-57-tButyl in PBS pH 6.5 at 9.0 mg/mL.
FIG. 6F includes a series of plots of transmission data upon heating (closed dots) and cooling (open dots) of all end-group modified MM-57-COOH in PBS pH 6.5 at 9.0 mg/mL.
Figure 6B:
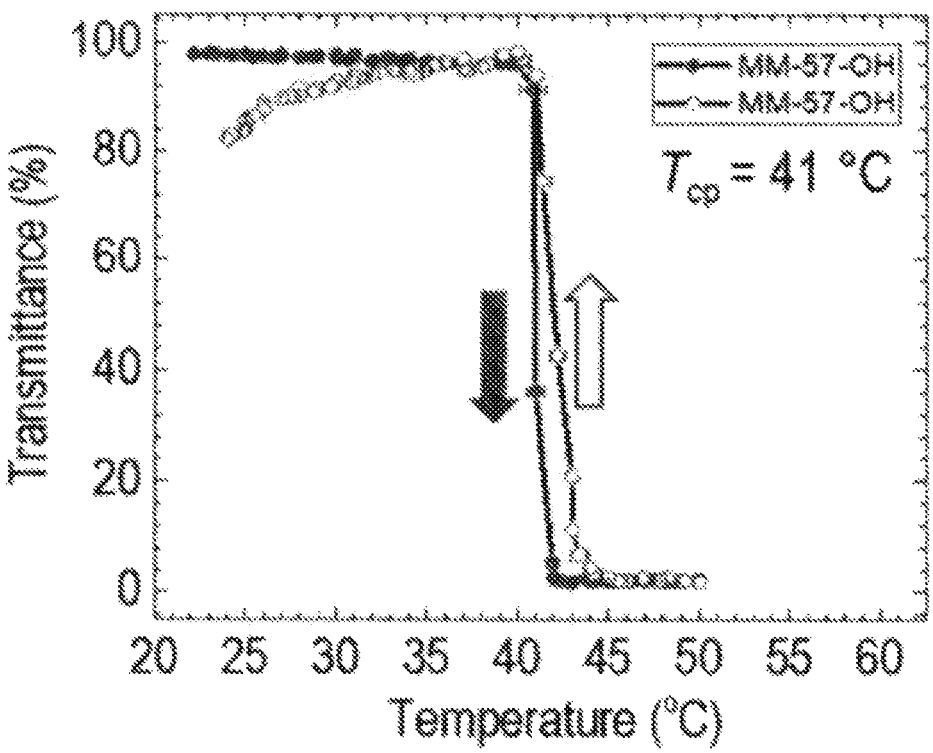
Figure 6C:
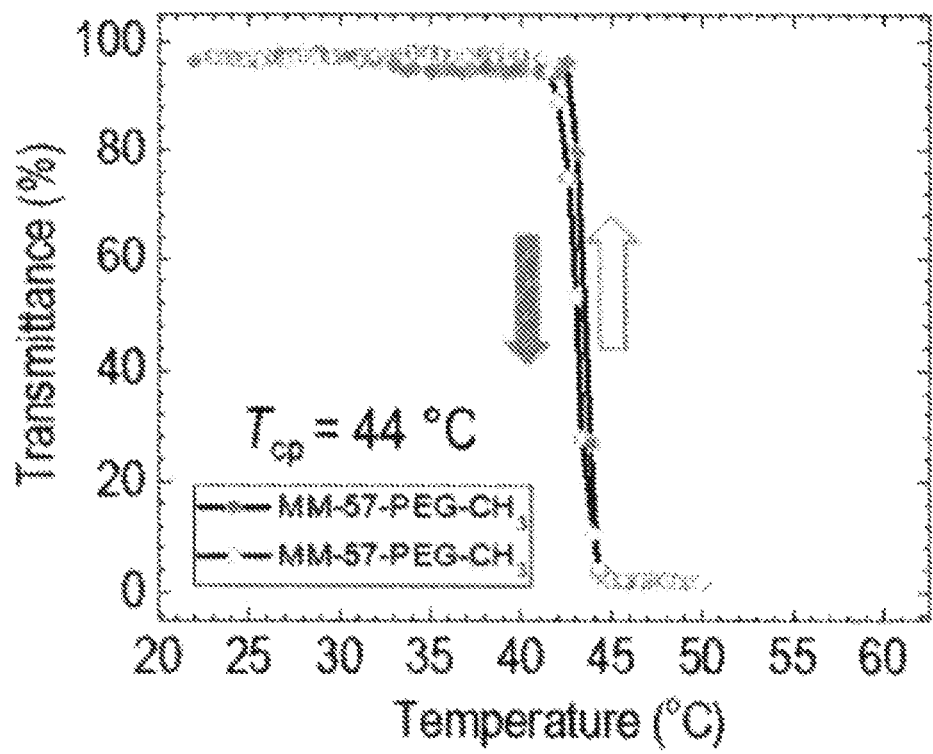
Figure 6D:
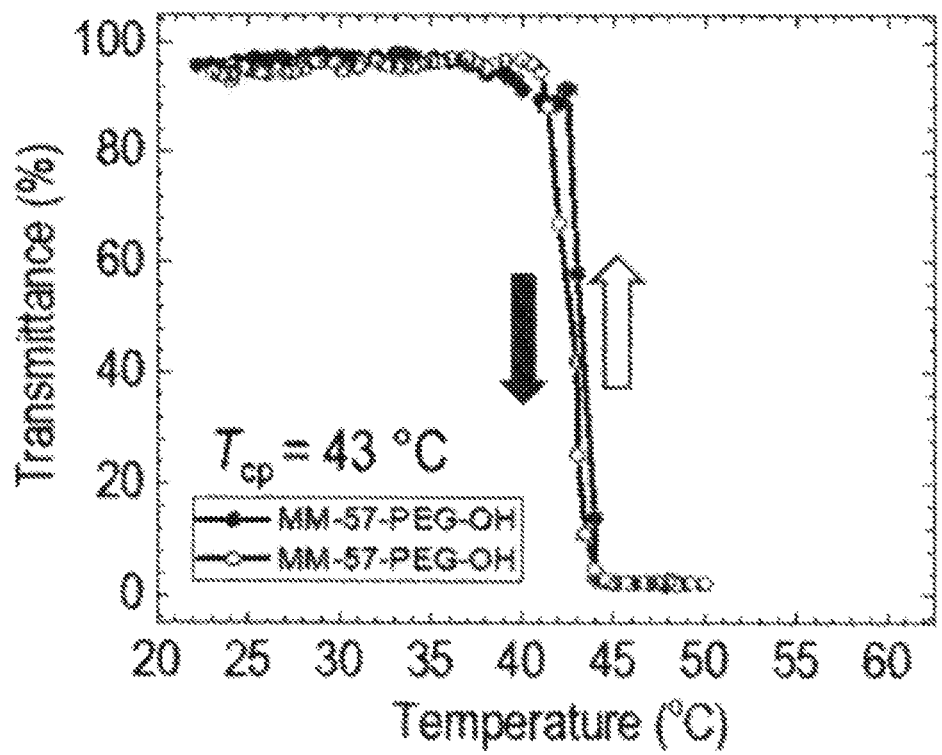
Figure 6E:
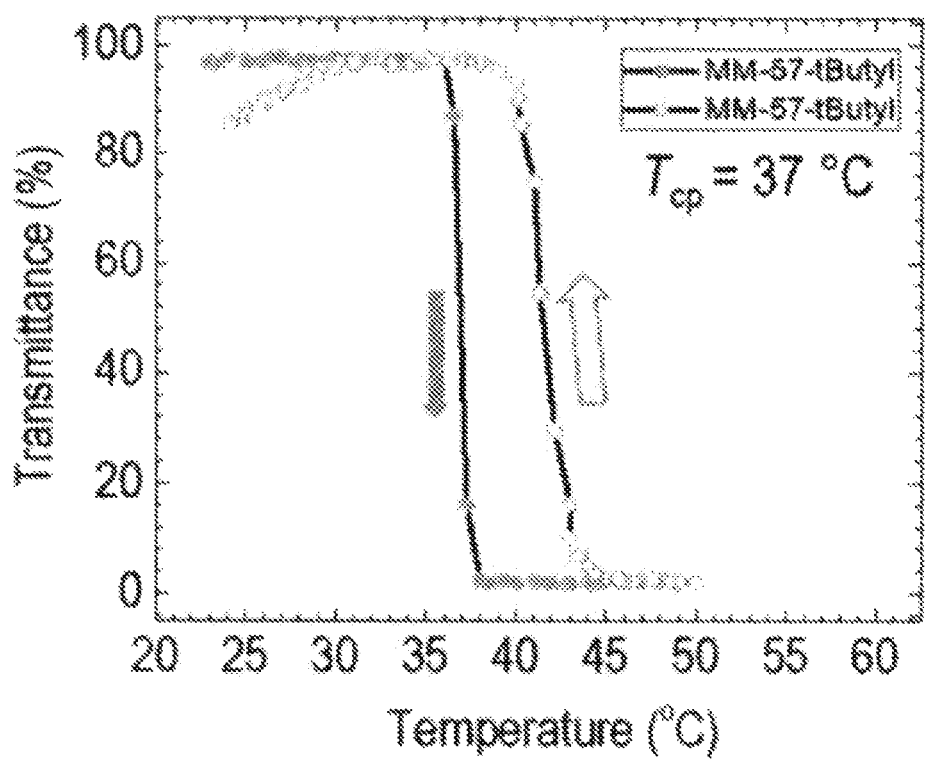
Figure 6F:
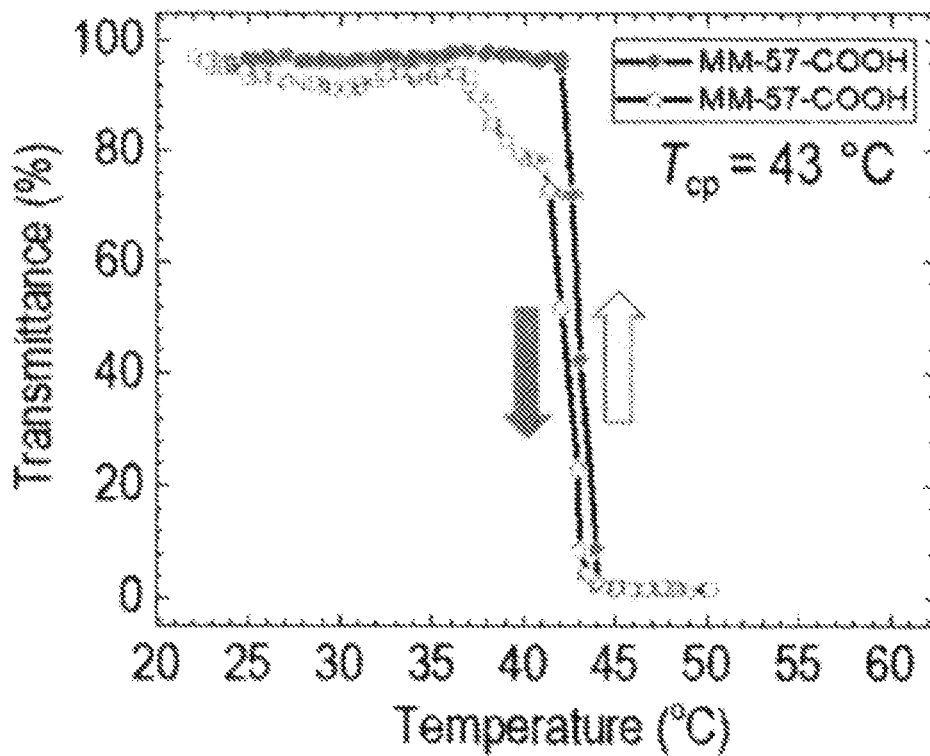
Figure 7A:
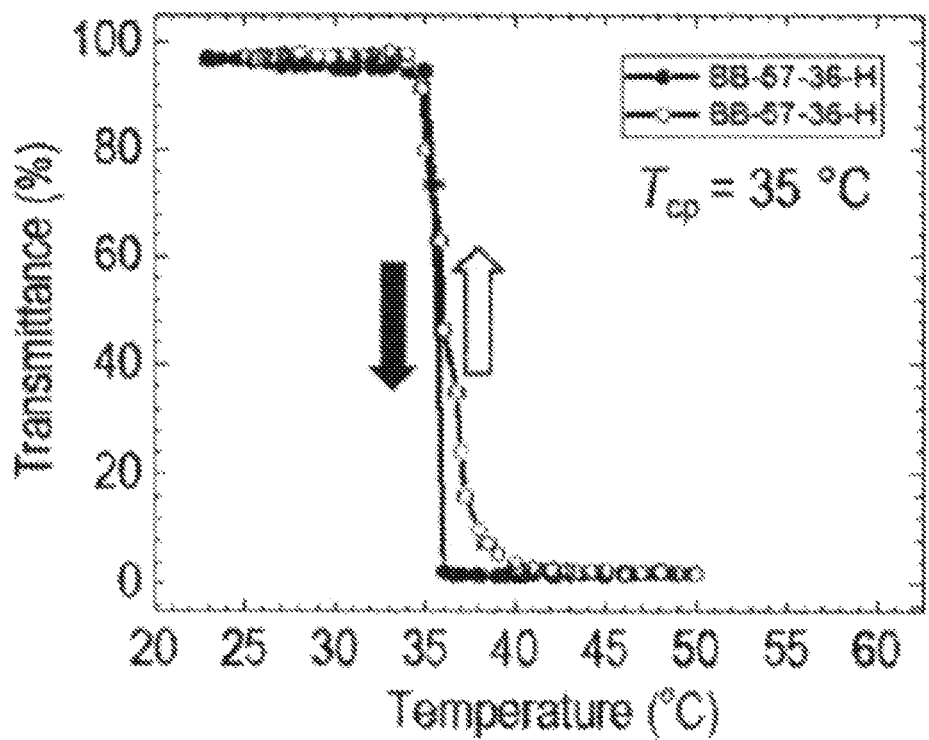
FIG. 7A includes a series of plots of transmission data upon heating (closed dots) and cooling (open dots) of all end-group modified BB-57-36-H in PBS pH 6.5 at 9.0 mg/mL.
Figure 7B:
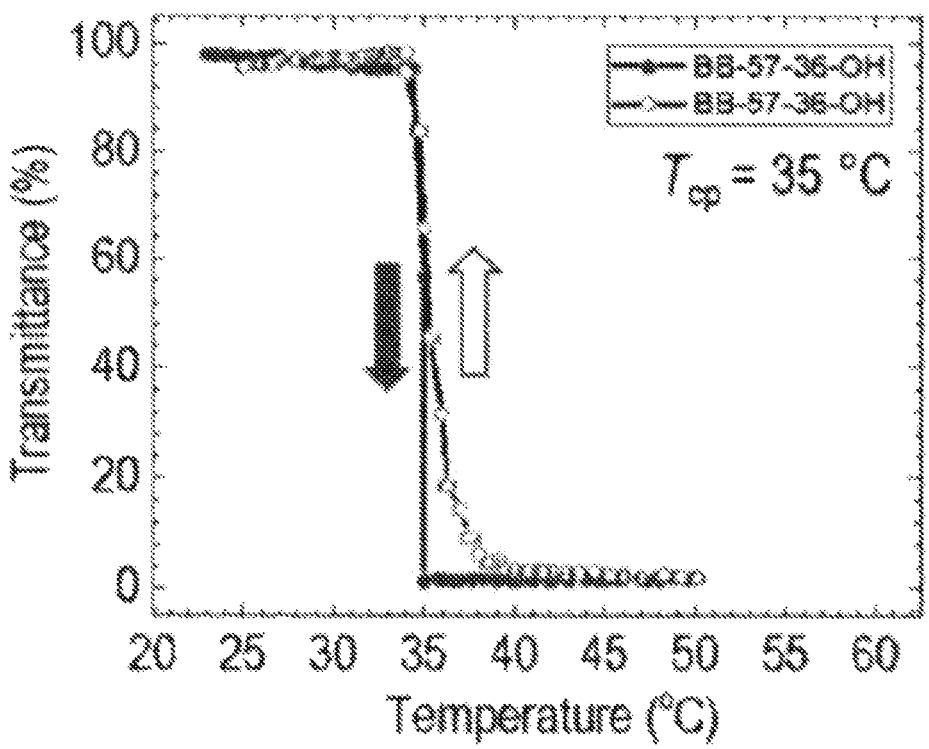
FIG. 7B includes a series of plots of transmission data upon heating (closed dots) and cooling (open dots) of all end-group modified BB-57-36-OH in PBS pH 6.5 at 9.0 mg/mL.
Figure 7C:
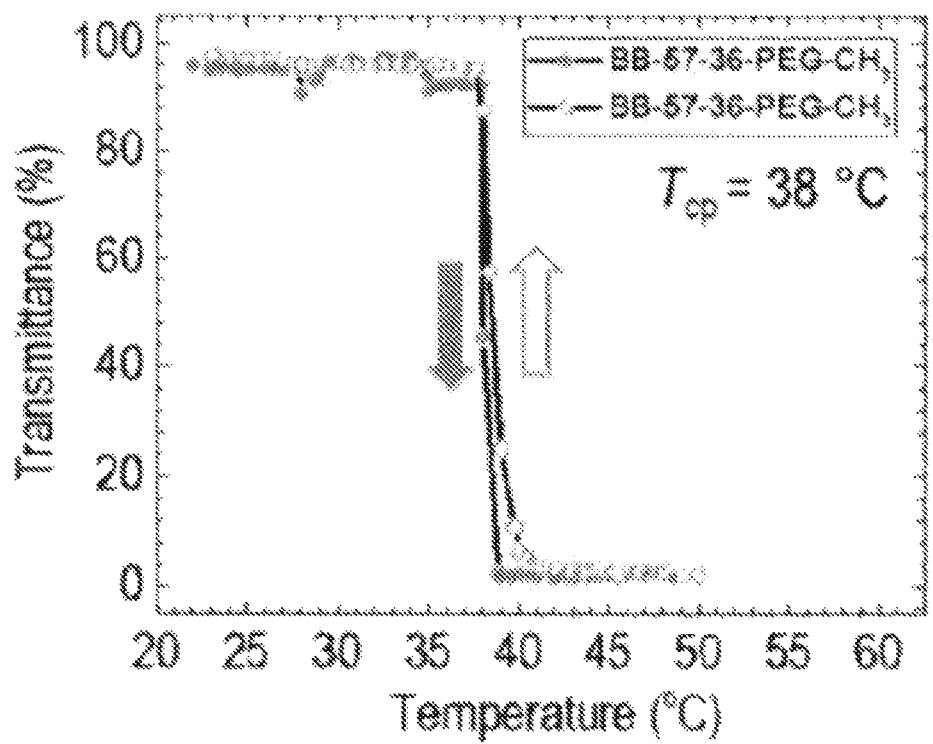
FIG. 7C includes a series of plots of transmission data upon heating (closed dots) and cooling (open dots) of all end-group modified BB-57-36-PEG-CH$_3$ in PBS pH 6.5 at 9.0 mg/mL.
Figure 7D:
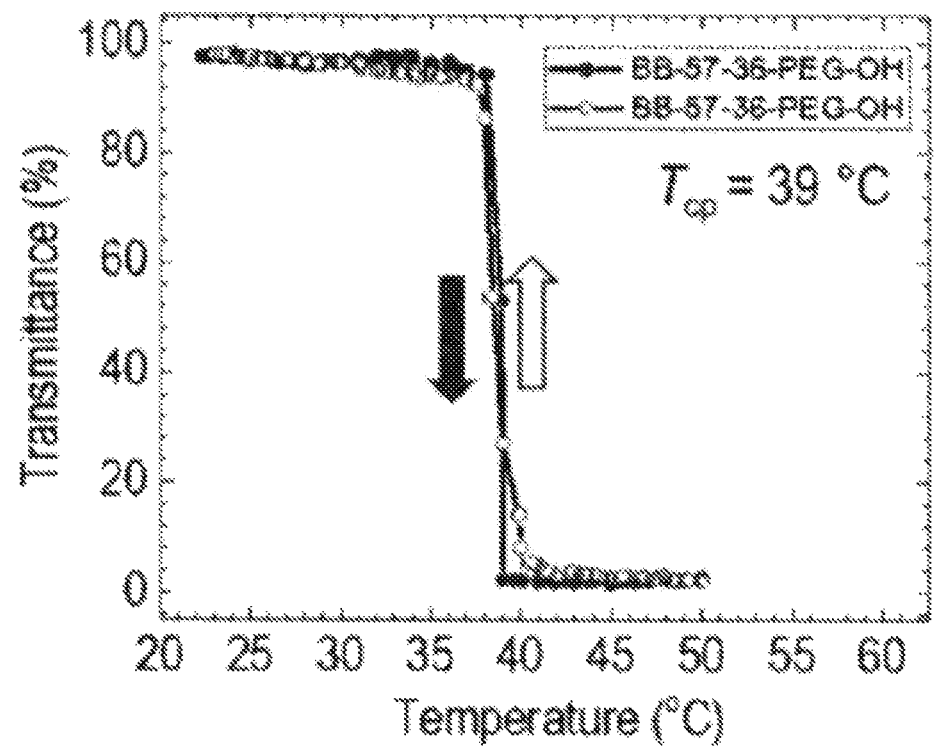
FIG. 7D includes a series of plots of transmission data upon heating (closed dots) and cooling (open dots) of all end-group modified BB-57-36-PEG-OH in PBS pH 6.5 at 9.0 mg/mL.
Figure 7E:
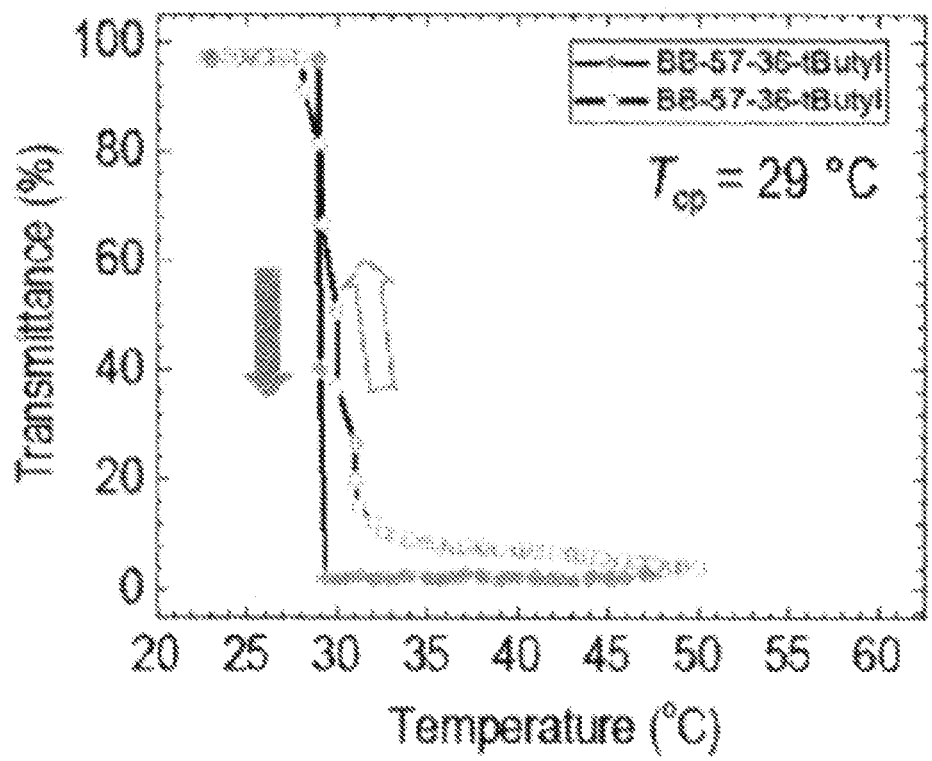
FIG. 7E includes a series of plots of transmission data upon heating (closed dots) and cooling (open dots) of all end-group modified BB-57-36-tButyl in PBS pH 6.5 at 9.0 mg/mL.
Figure 7F:
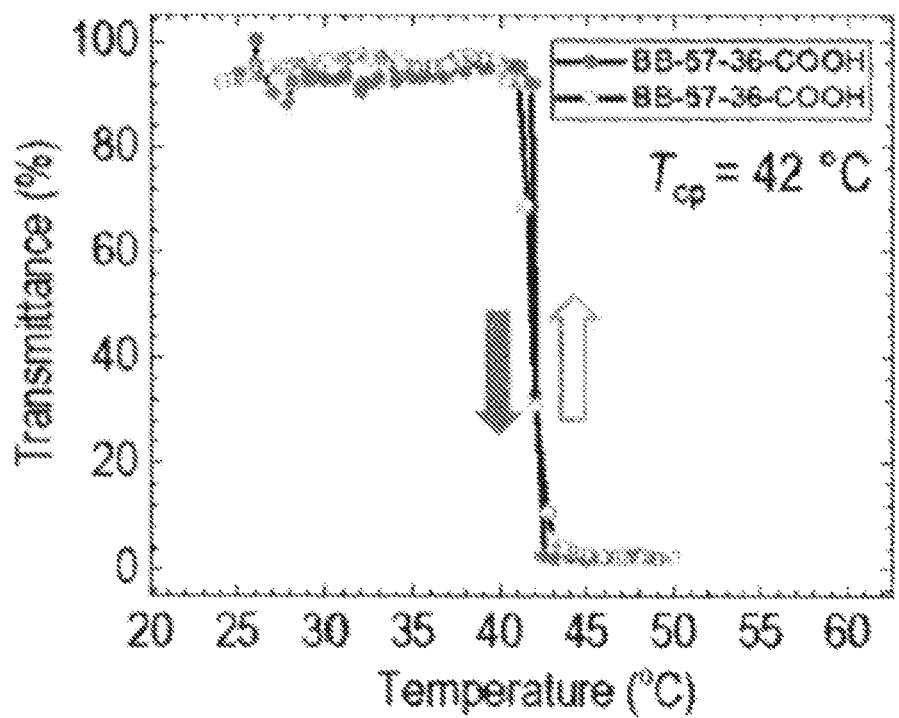
FIG. 7F includes a series of plots of transmission data upon heating (closed dots) and cooling (open dots) of all end-group modified BB-57-36-COOH in PBS pH 6.5 at 9.0 mg/mL.
Figure 8A:
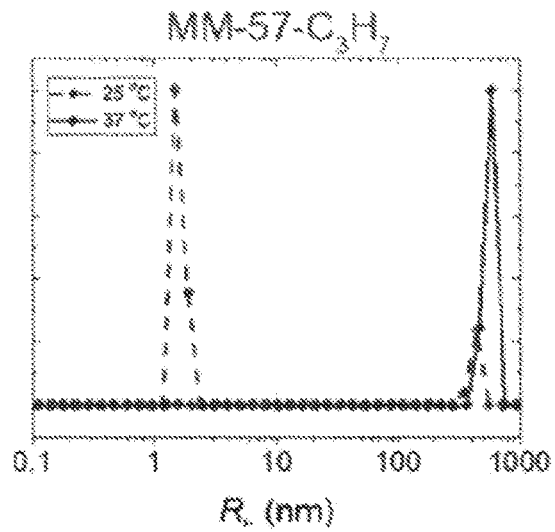
FIG. 8A-G includes a series of plots summarizing MM-57-Z R$_h$ distributions using a regularization fit for —C$_3$H$_7$ (FIG. 8A), —H (FIG. 8B), —OH (FIG. 8C), -PEG-CH$_3$ (FIG. 8D), -PEG-OH (FIG. 8E), -tButyl (FIG. 8F), and —COOH (FIG. 8G). Samples were 9 mg/mL in PBS (pH 6.5) measured at both 25 (dotted lines) and 37 (solid lines) ° C.
Figure 8B:
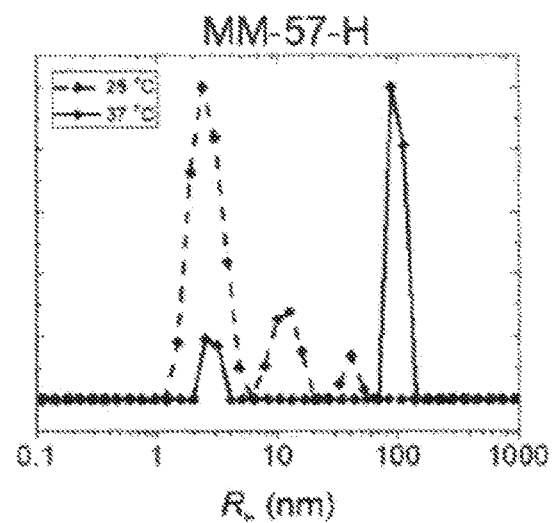
Figure 8C:
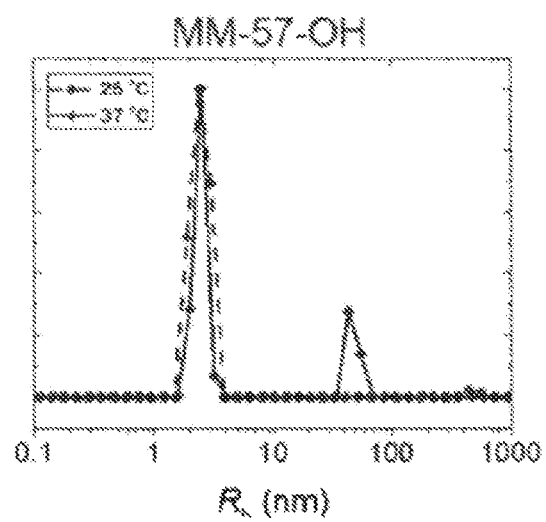
Figure 8D:
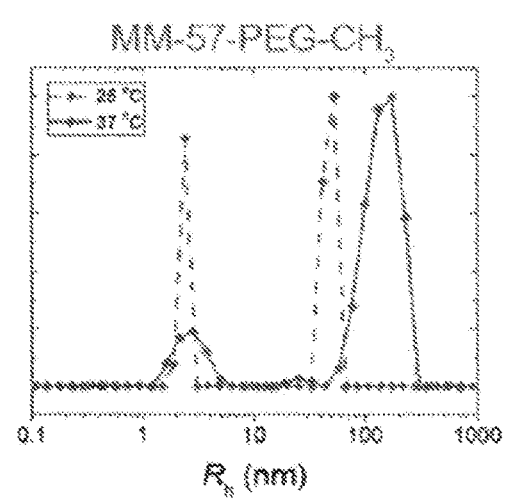
Figure 8E:
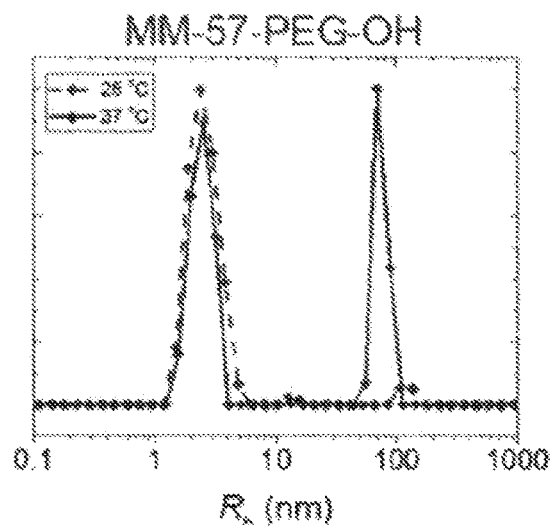
Figure 8F:
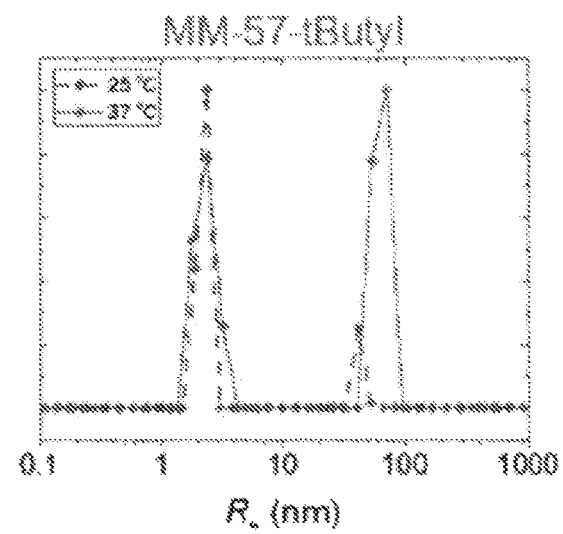
Figure 8G:
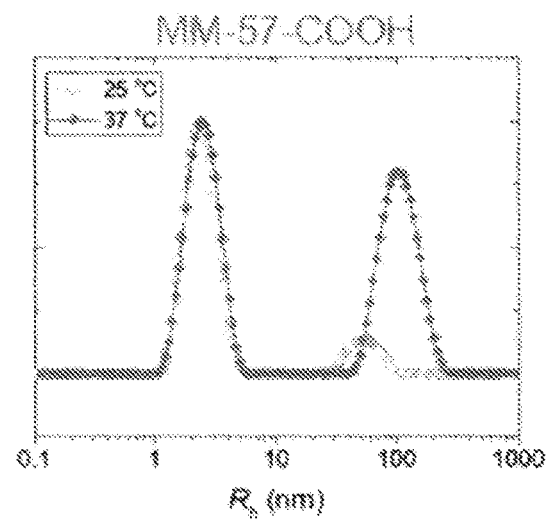
Figure 9A:
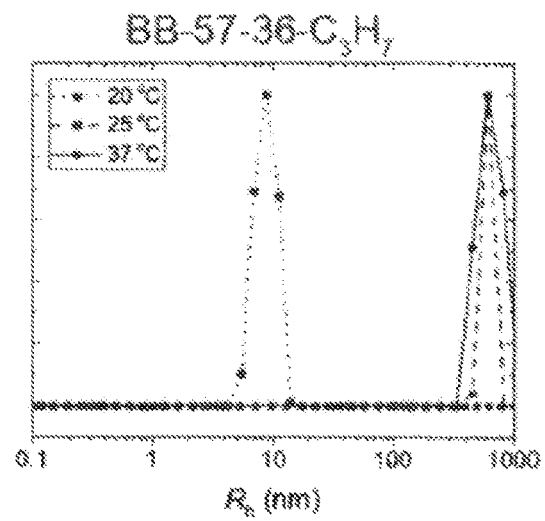
FIGS. 9A-G includes a series of plots summarizing R$_h$ distributions for BB-57-36-Z fit using a regularization fit for —C$_3$H$_7$ (FIG. 9A), —H (FIG. 9B), —OH (FIG. 9C), -PEG-CH.
Figure 9B:
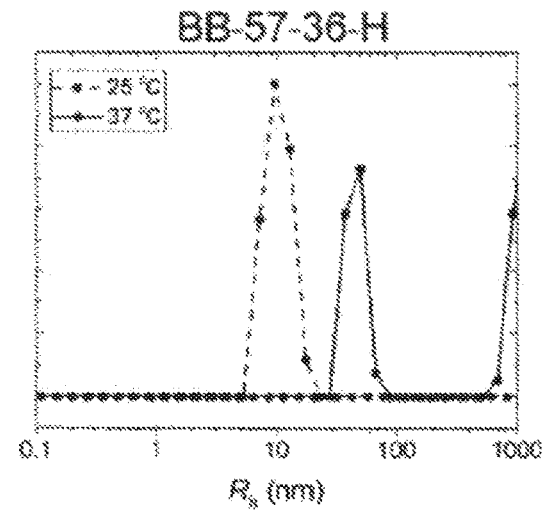
Figure 9C:
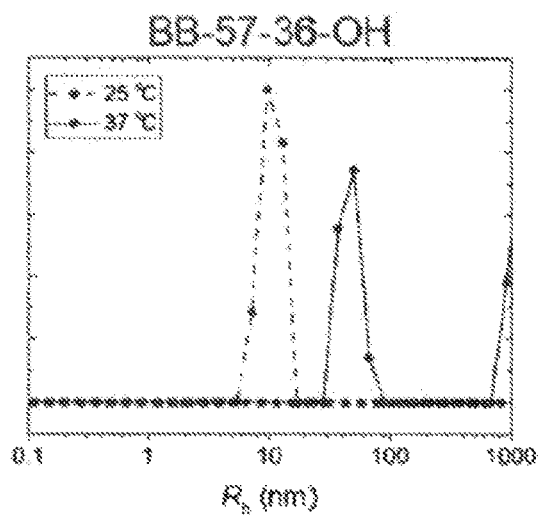
Figure 9D:
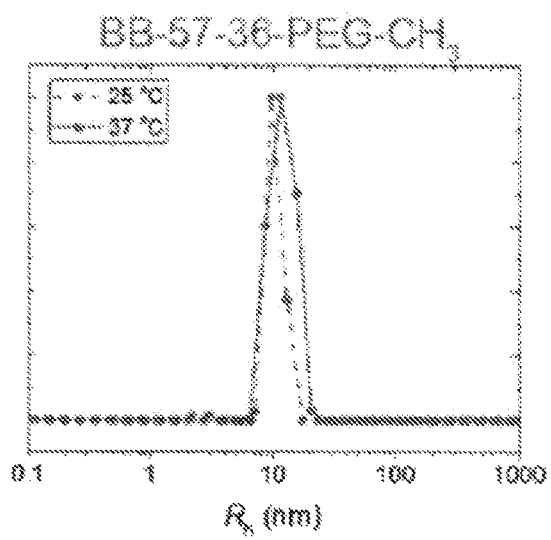
Figure 9E:
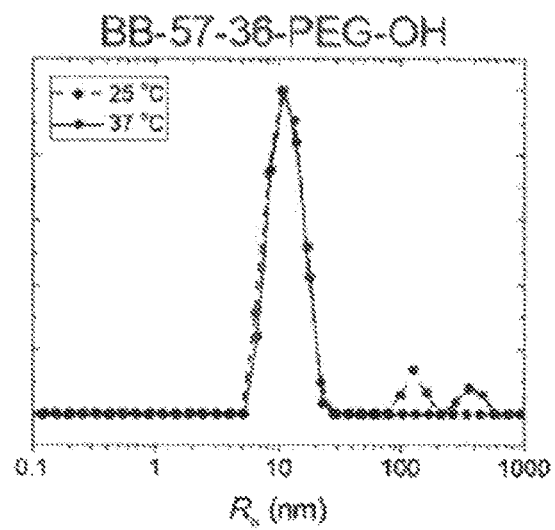
Figure 9F:
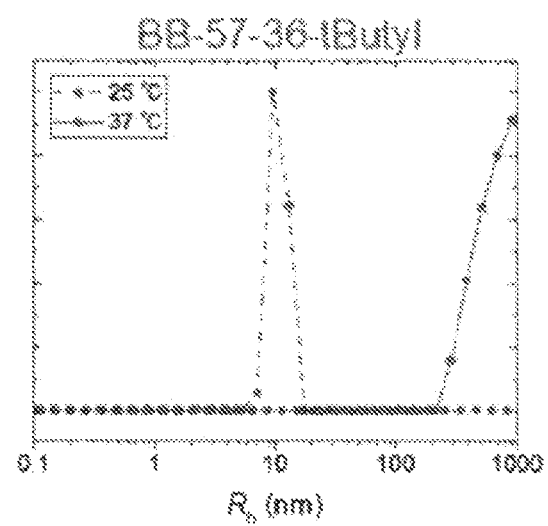
Figure 9G:
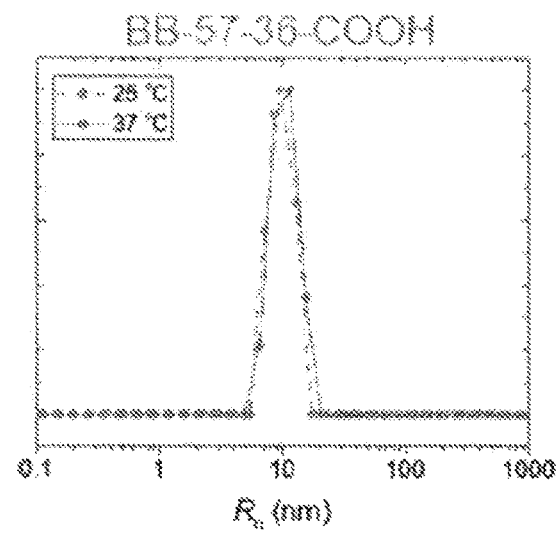

Scheme A in FIG. 5 was the general RAFT polymerization scheme for linear controls 1-5 with the following chain transfer agents: (1,2) 2-(propyithiocarbonothioyithio)-2 methyl propionic acid, (3) 2-(Dodecylthiocarbonothioyl-thio)-2-methylpropionic acid. (4) 4-Cyano-4-[(dodecylsul-fanylthiocarbonyl) sulfanyl]pentanoic acid, and (5) 2-Cyano-2-propyl dodecyl trithiocarbonate. The R- and Z-groups of the trithiocarbonate CTA and molecular weight were changed to create the five controls: (a) propionic acid (PA, orange), (b) cyano-acid (CA, orange), (c) cyano-acid (CA, grey), (d) propyl hydrocarbon chain (—C$_3$H$_7$, green), and (e) dodecyl hydrocarbon chain (—C$_{12}$H$_{25}$, black).

Scheme B in FIG. 5 shows cartoon representations of the linear polymer controls and their solution structures in aqueous media—grey lines represent the copolymer: (1) PA-PND-245-C$_3$H$_7$ and (2) PA-PND-61-C$_3$H$_7$ exist as free chains, (3) C$_{12}$H$_{25}$ forms micelles, (4) CA-PND-62-C$_{12}$H$_{25}$ forms micelles, and (5) CP-PND-62-C$_{12}$H$_{25}$ forms micelles.

The general polymerization procedure was as follows: DMA was filtered through basic alumina. NIPAm (140 mmol, 15.83 g) and the respective chain transfer agent (3.74 mmol, 1.61 g) was dissolved in 1,4-dioxane (200 mL, 1.0 M). DMA (60 mol, 6.314 mL) was added along with AIBN (0:187 mmol, 30.7 mg). The solution was degassed with N$_{2(g)}$ for 30 minutes and stirred overnight at 70° C. The reaction was quenched in liquid nitrogen and opened to air. The polymer was either purified by precipitation in 60/40 Hexanes/Ethyl Ether three times to remove all monomer (1 and 2) or dialysis in methanol with a 1 kDa (3-5) and dried in a vacuum oven. The polymers were characterized by $^1$H NMR in CDCl$_3$ and SEC-MALS in DMF with 0.05M LiBr.

A summary the properties of the copolymer controls is shown in Table 2 below:

TABLE 2

| # Control | Composition (N/D) | M$_{n,SEC}$ (kDa) | M$_{w,SEC}$ (kDa) | M$_{a,NMR}$ (kDa) | Đ | T$_{cp}$ (° C.) |
|---|---|---|---|---|---|---|
| 1 Proponic acid-PND-245-C$_3$H$_7$ | 65/35 | 27 | 30 | 31* | 1.11 | 39 |
| 2 Proponic acid-PND-61-C$_3$H$_7$ | 66/34 | 7.0 | 6.8 | 7.3* | 1.02 | 44 |
| 3 Proponic acid-PND-62-C$_{12}$H$_{25}$ | 66/34 | 7.0 | 7.2 | 7.1** | 1.02 | 50 |
| 4 Cyano-acid-PND-62-C$_{12}$H$_{25}$ | 66/34 | 7.0 | 7.2 | 7.0** | 1.02 | 52 |
| 5 Cyano-propyl-PND-72-C$_{12}$H$_{25}$ | 64/36 | 8.1 | 8.3 | 9.0** | 1.02 | 38 |

*end-group analysis calibrated to CH$_2$ at 3.35 ppm
**end-group analysis calibrated to CH$_3$ at 0.87 ppm Solution Characterization Cloud Point Measurements:

Polymers were dissolved at 9 mg/mL in PBS pH 6.5 and filtered into glass ampules. The samples were heated at an approximate rate of 0.25 C/min from room temperature to 50 or 60° C. The optical transmittance of a 30 mW 633 run HeNe laser was recorded on a Spex Industries Laser Power Meter 1448 photometer (Metuchen, NJ) upon heating and cooling. The cloud point was defined as when the transmittance dropped below 80% from the normalized transmittance at room temperature.

Transmission data upon heating (closed dots) and cooling (open dots) of all end-group modified MM-57-Z in PBS pH 6.5 at 9.0 mg/mL are shown in FIGS. 6A-6F.

Transmission data upon heating (closed dots) and cooling (open dots) of all end-group modified BB-57-36-Z in PBS pH 6.5 at 9.0 mg/mL are shown in FIGS. 7A-7F.

Dynamic Light Scattering

The hydrodynamic radius of each Control, MM, and BB were measured at 9 mg/mL in PBS (pH 6.5) at 25 and 37° C. using a high-throughput plate reader DLS (DynaPro Plate Reader DLS, Wyatt Technologies, Santa Barbara, CA). Each $R_h$ distribution was calculated using Regularization (a non-negative least squares fitting algorithm defined by Wyatt Technology) of the correlation function and the results are summarized in Table 3 below.

TABLE 3

Summary of dynamic light scattering results of Control's, MM-57-X, and BB-57-36-X

| Sample | $R_{h, 25°C.}$ 9 mg/mL (nm) | PDI | $R_{h, 37°C.}$ 9 mg/mL (nm) | PDI |
|---|---|---|---|---|
| 1 Proponic acid-PND-245-$C_3H_7$ | 5.5, 34.0 | 0.29, 0.22 | 55, 25.1 | 0.23, 0.23 |
| 2 Proportic acid-PND-61-$C_3H_7$ | 2.5 | 0.18 | 2.2 | 0.12 |
| 3 Proponic acid-PND-62-$C_{12}H_{25}$ | 7.4 | 0.16 | 7.5 | 0.12 |
| 4 Cyano-acid-PND-62-$C_{12}H_{25}$ | 7.1 | 0.12 | 7.5 | 0.12 |
| 5 Cyano-propylPND-72-$C_{12}H_{25}$ | 7.9 | 0.04 | 8.7 | 0.11 |
| MM-57-$C_3H_7$ | 1.6 | 0.11 | turbid | turbid |
| BB-57-36-$C_3H_7$ | 8.8* | 0.20* | turbid | turbid |
| MM-57-H | 2.7, 11.7 | 0.29, 0.22 | turbid | turbid |
| BB-57-36-H | 10.5 | 0.25 | turbid | turbid |
| MM-57-OH | 2.6 | 0.31 | 2.4, 71 | 0.18, 0.14 |
| BB-57-36-OH | 10.6 | 0.19 | turbid | turbid |
| MM-57-PEG-$CH_3$ | 2.5 | 0.17 | 2.5, 46 | 0.16, 0.09 |
| BB-57-36-PEG-$CH_3$ | 10.5 | 0.15 | 10.8 | 0.19 |
| MM-57-PEG-OH | 2.3, 47.6 | 0.06, 0.11 | 2.8, 140 | 0.33, 0.30 |
| BB-57-36-PEG-OH | 10.5 | 0.32 | 11.0 | 0.29 |
| MM-57-tButyl | 2.2 | 0.22 | 2.4, 67 | 0.19, 0.15 |
| BB-57-36-tButyl | 10.8 | 0.13 | turbid | turbid |
| MM-57-COOH | 2.4‡ | 0.34 | 2.4, 99.6‡ | — |
| BB-57-36-COOH | 10.0 | 0.20 | 10.8 | 0.20 |

*measure at 20° C.,
‡radius distribution calculated using REPES at 90°

A summary of MM-57-Z $R_h$ distributions using a regularization fit are shown in FIGS. 8A-8G. The samples were 9 mg/mL in PBS (pH 6.5) measured at both 25 and 37° C.

A summary of $R_h$ distributions for BB-57-36-Z fit using a regularization fit are shown in FIGS. 9A-9G. The samples were 9 mg/mL in PBS (pH 6.5) measured at both 25 and 37° C.

Multiangle Dynamic Light Scattering

DLS measurements were performed on an in-house photometer (30 mW laser power, avalanche photodiode detector with a 200 μm pinhole) over a range of angles (60-120°) with a Brookhaven BI-200SM goniometer and a Brookhaven BI-9000AT correlator at λ=637 nm at 25° C. The dispersity of particle size was quantified by the either the second or third cumulant $\mu_2/\Gamma^2$ with $\Gamma$ being the mean decay rate of first-order scattering autocorrelation. The size distribution was also assessed through the REPES Laplace inversion routine. The results are shown in Table 4 below.

TABLE 4

Summary of solution characterization with multi-angle dynamic light scattering

| Sample | $R_{h, 25°C.}$ 2nd cumulant (nm) | $\mu_2/\Gamma^2$ | $R_{h, 25°C.}$ REPES (nm) | Density (mg/mL) |
|---|---|---|---|---|
| PA-PND-62-$C_{12}H_{25}$ | 7.0† | 0.21† | 7.4 | 74a |
| BB-57-36-$C_3H_7$ | 9.5* | 0.11* | 10.1* | 105* |
| BB-57-36-H | 9.6 | 0.07 | 9.7 | 101 |
| BB-57-36-OH | 10.0 | 0.09 | 10.7 | 91 |
| BB-57-36-PEG-$CH_3$ | 10.0 | 0.07 | 10.7 | 89 |
| BB-57-36-PEG-OH | 9.7 | 0.13 | 10.0 | 99 |
| BB-57-36-tButyl | 9.6 | 0.07 | 9.8 | 100 |
| BB-57-36-COOH | 9.8 | 0.08 | 10.3 | 96 |

Figure 10A:
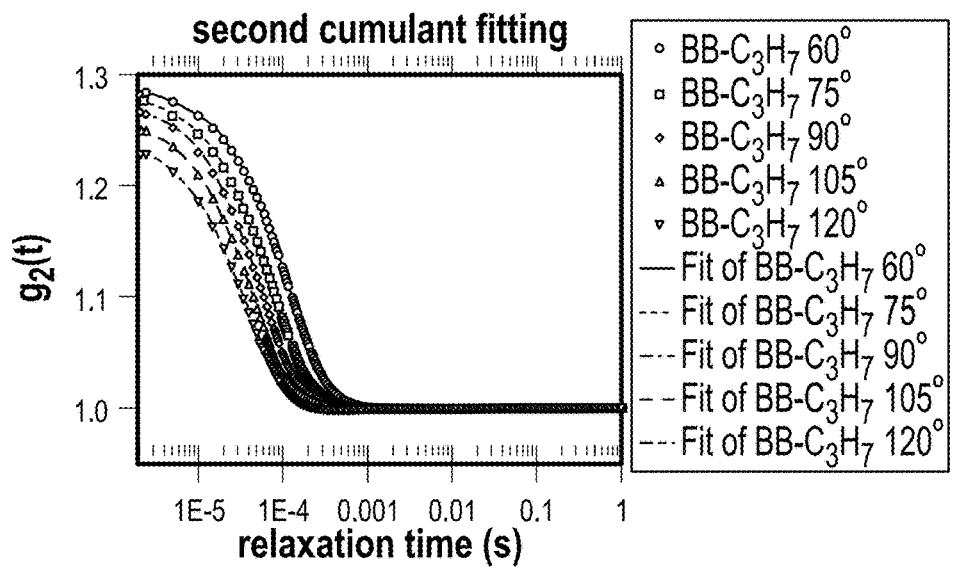
FIGS. 10A-U are a series of plots showing a second cumulant fits for BB-57-36-C$_3$H$_7$, —H, —OH, -PEG-CH$_3$, -PEG-OH, -tButyl, and —COOH measured at 60, 75, 90, 105, and 120° at 25° C. at 1 mg/mL in PBS (pH 6.5). Each fit is shown along with the Γ vs. q$^2$ plot and overlay of all REPES distributions over the multiple angles.
Figure 10B:
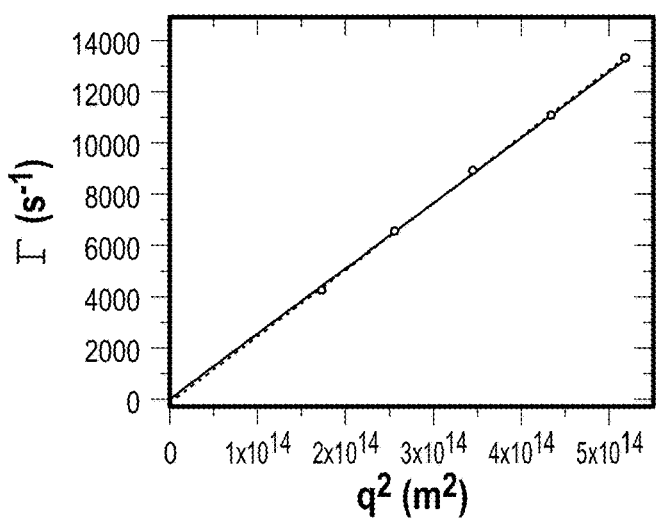
Figure 10C:
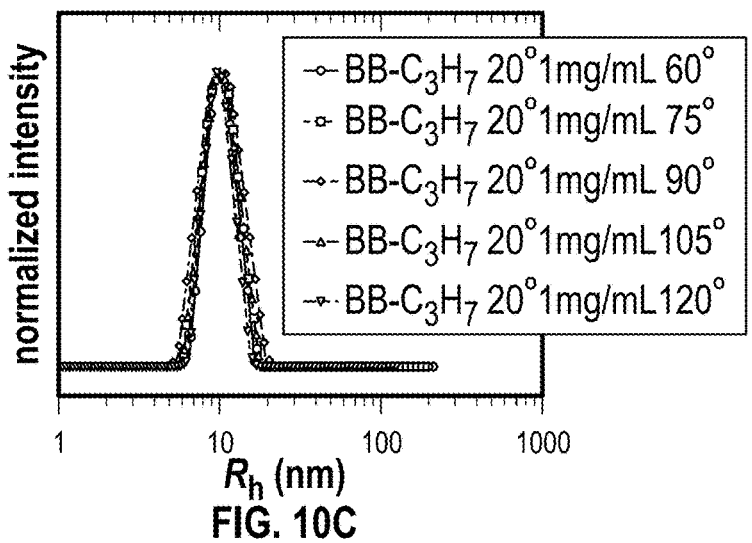
Figure 10D:
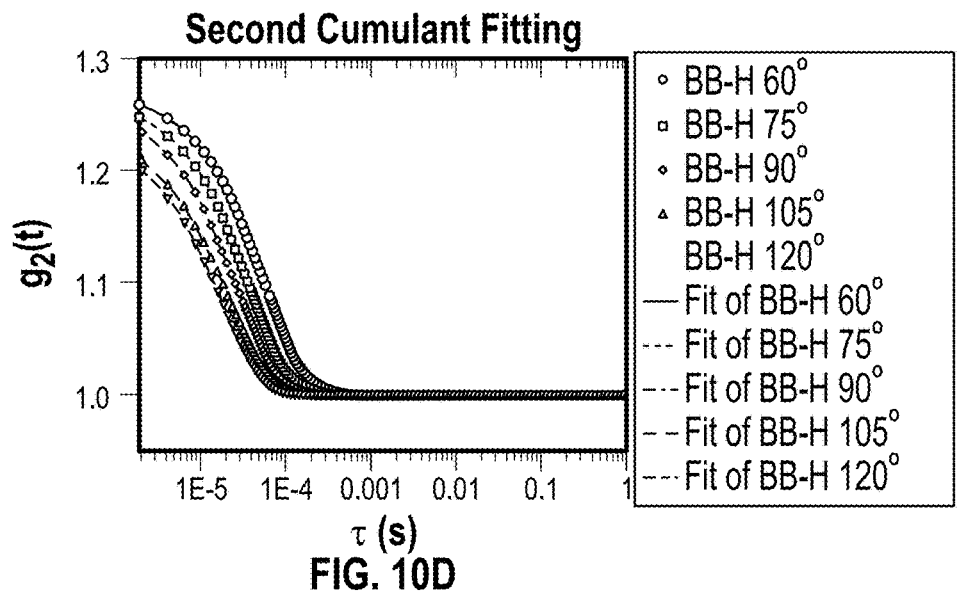
Figure 10E:
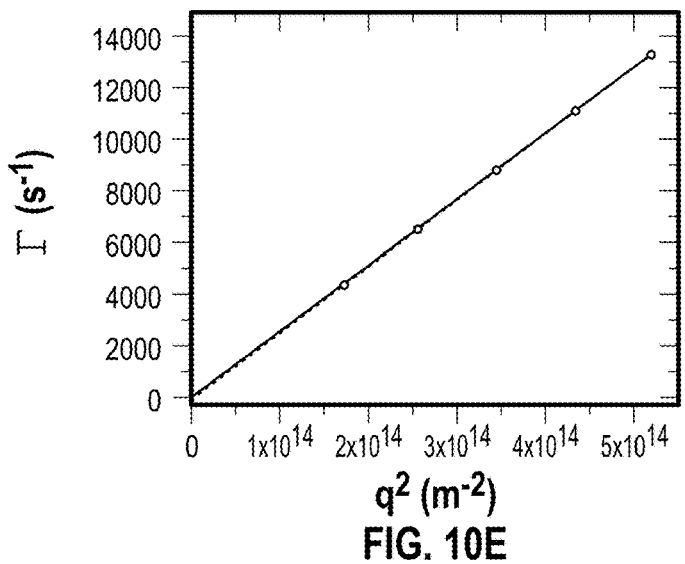
Figure 10F:
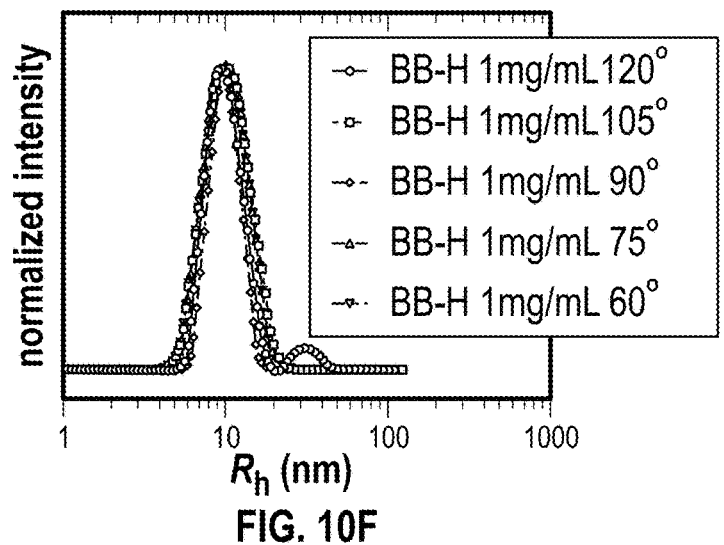
Figure 10G:
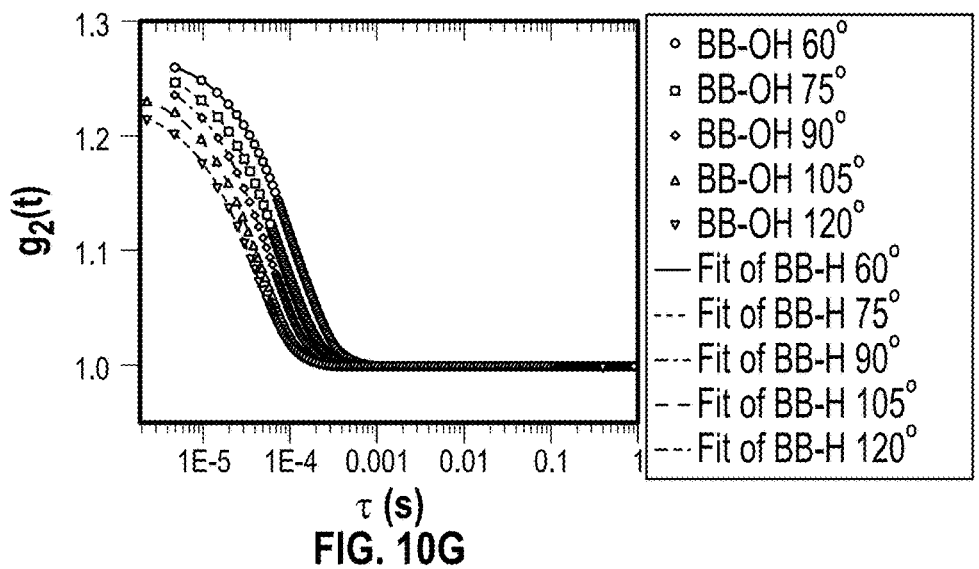
Figure 10H:
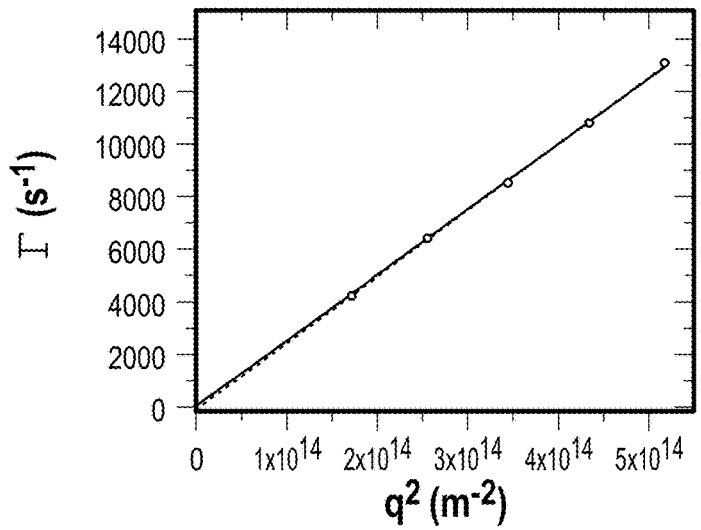
Figure 10I:
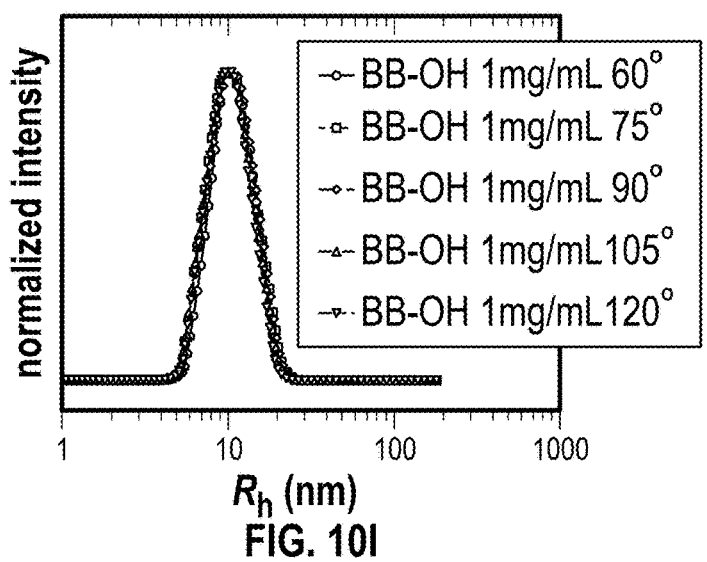
Figure 10J:
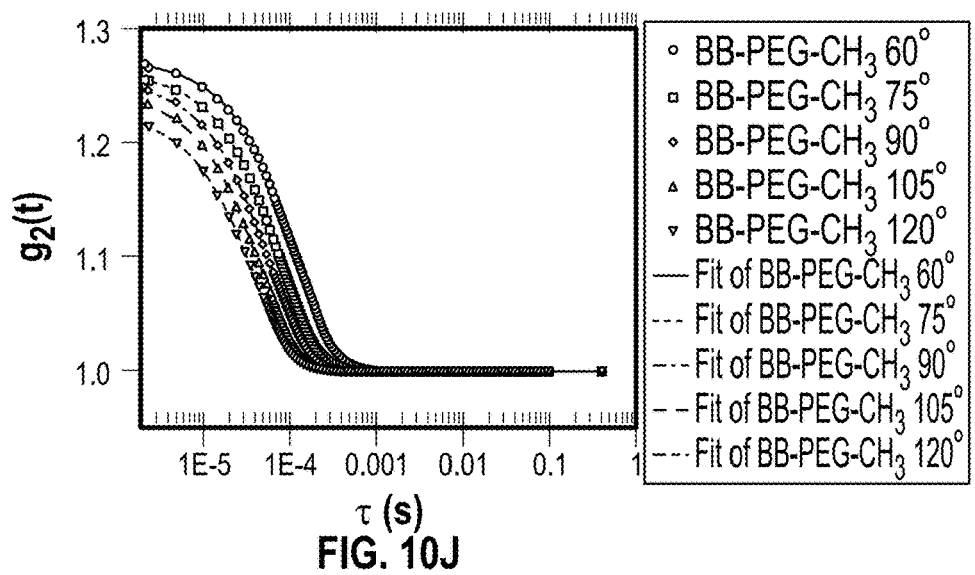
Figure 10K:
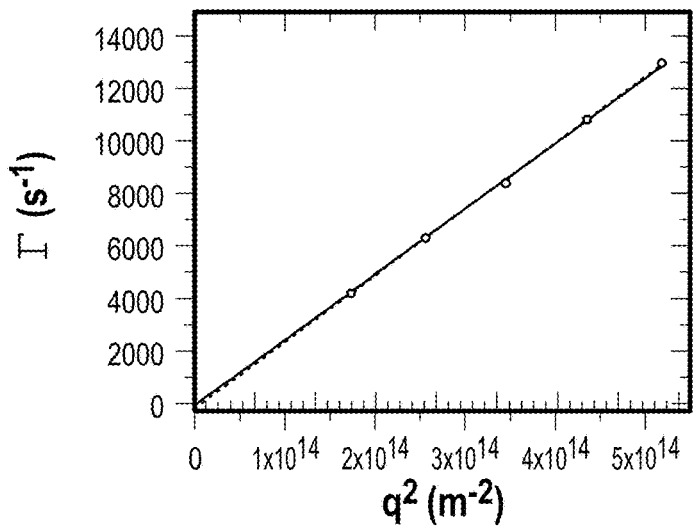
Figure 10L:
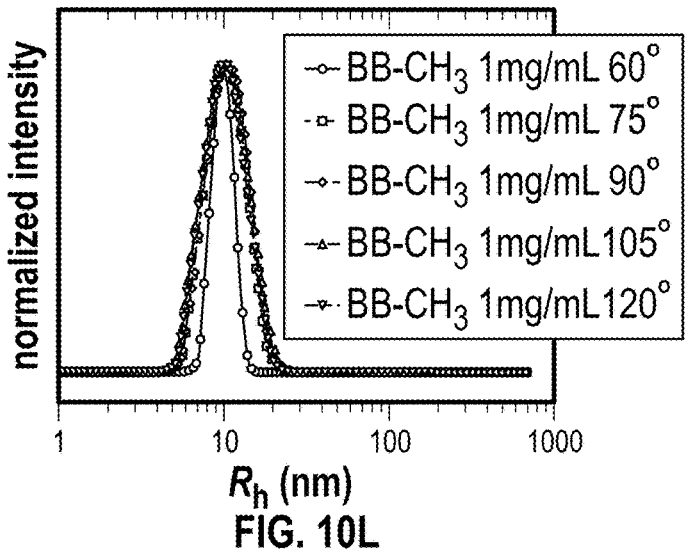
Figure 10M:
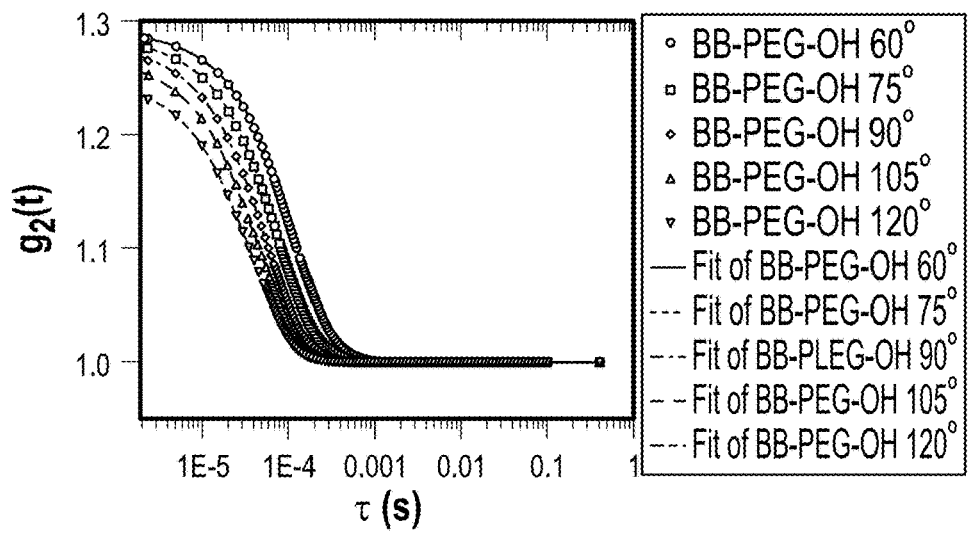
Figure 10N:
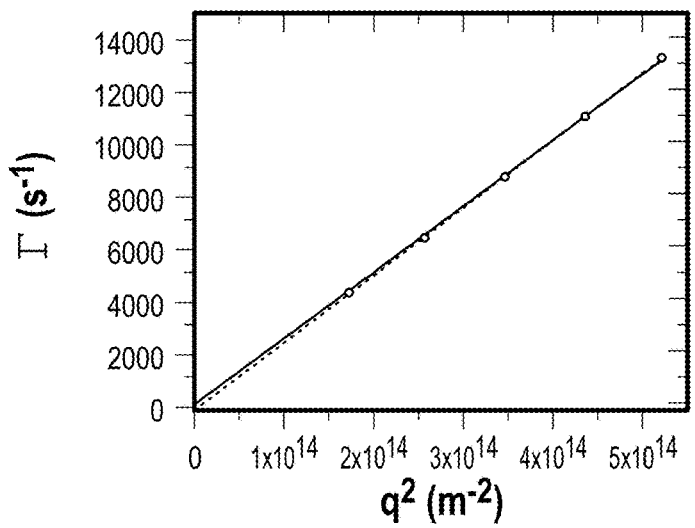
Figure 10O:
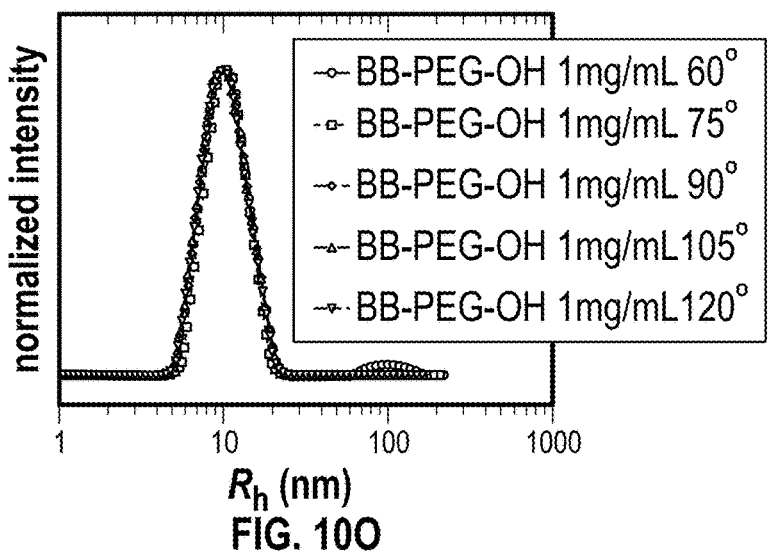
Figure 10P:
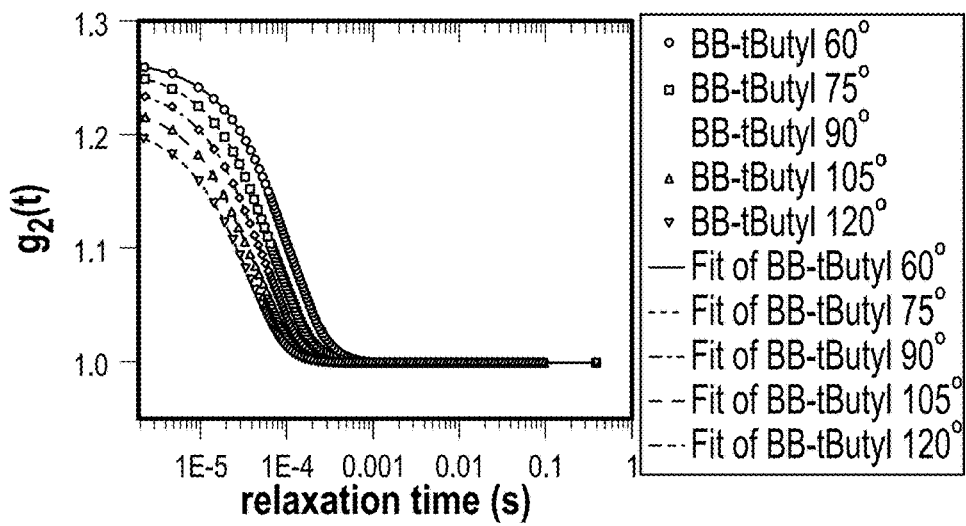
Figure 10Q:
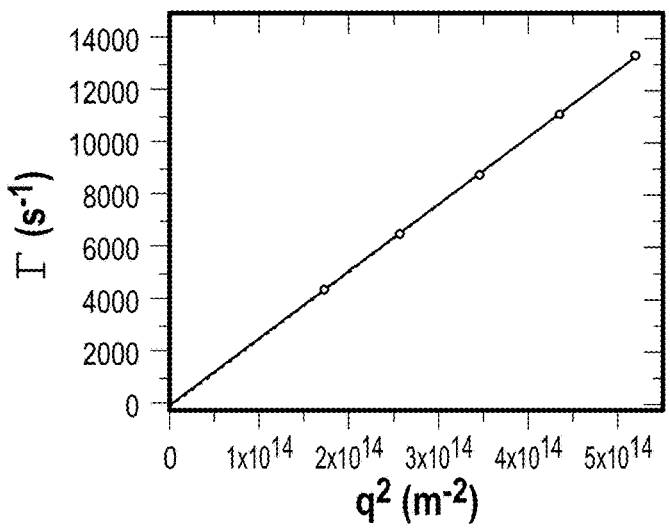
Figure 10R:
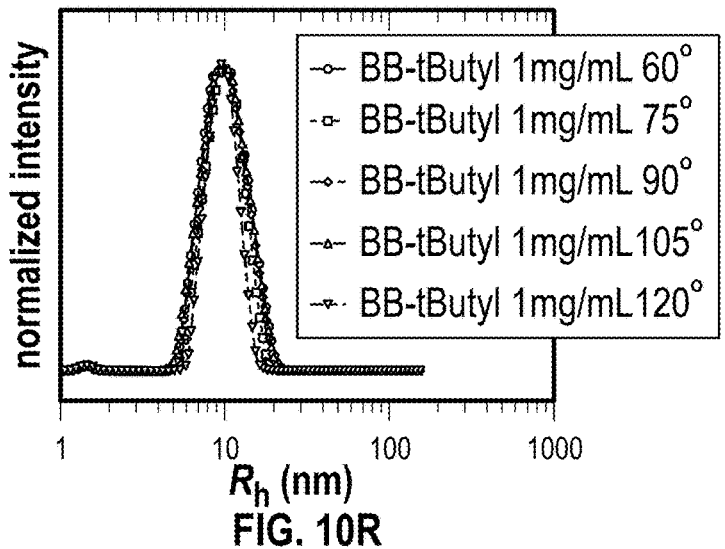
Figure 10S:
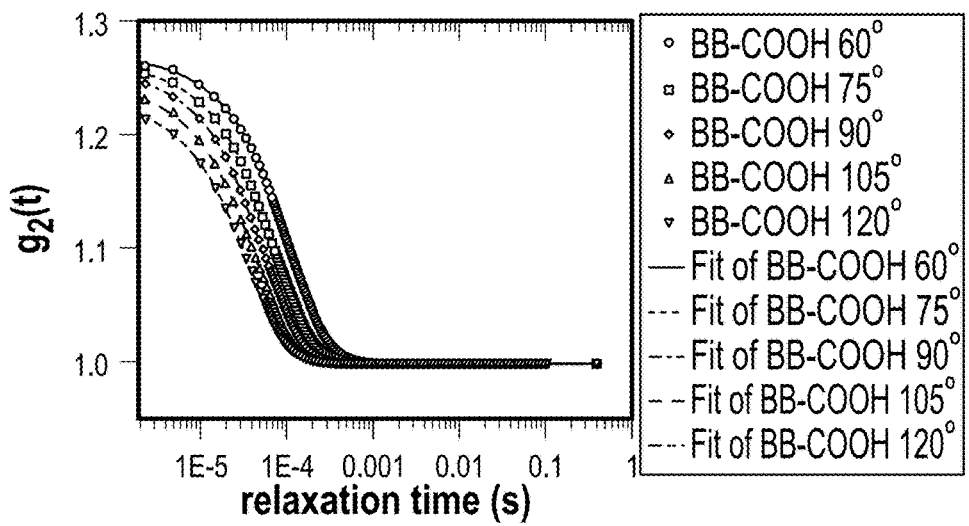
Figure 10T:
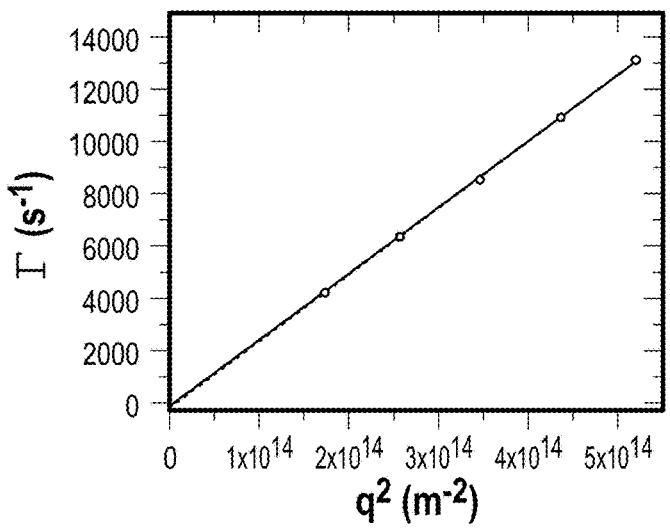
Figure 10U:
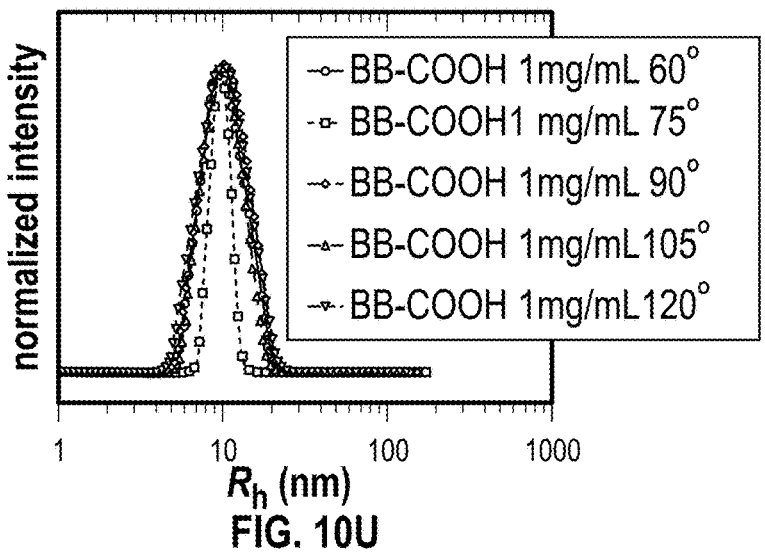

†Third cumulant analysis
*measured at 20° C.
a estimated from literature precedent FIGS. 10A-10U are a series of plots showing a second cumulant fits for BB-57-36-$C_3H_7$, —H, —OH, -PEG-$CH_3$, -PEG-OH, -tButyl, and —COOH measured at 60, 75, 90, 105, and 120° at 25° C. at 1 mg/mL in PBS (pH 6.5), Each fit is shown along with the $\Gamma$ vs. $q^2$ plot and overlay of all REPES distributions over the multiple angles.

Static Light Scattering (SLS)

Solutions for SLS were prepared by serial dilutions of the polymers in filtered PBS with a pH 6.5. The dn/dc values for each polymer in PBS with a pH 6.5 were measured and are recorded in Table 5 below. Scattering measurements were collected using the same in-house instrument described in Multiangle Dynamic Light Scattering. Zimm analysis was used to calculate the molar mass ($M_w$), second virial coefficient ($A_2$), and radius of gyration ($R_g$).

TABLE 5

Summary of Zimm Plot Results

| Sample | dn/dc (mL/g) | $M_w$ (kDa) | $N_{bb}$ | $A_2$ (×10$^{-5}$ mol cm$^3$/g$^2$) | $R_{g,\ 25°C}$ (nm) | $R_g/R_{h,\ 25°\ C.}$ |
|---|---|---|---|---|---|---|
| BB-57-36-PEG—CH$_3$ | 0.18 ± 0.01 | 230 | 34 | 6 | 10.1 | 1.01 |
| BB-57-36-COOH | 0.17 ± 0.01 | 252 | 38 | 23 | 9.41 | 0.96 |

Figure 11A:
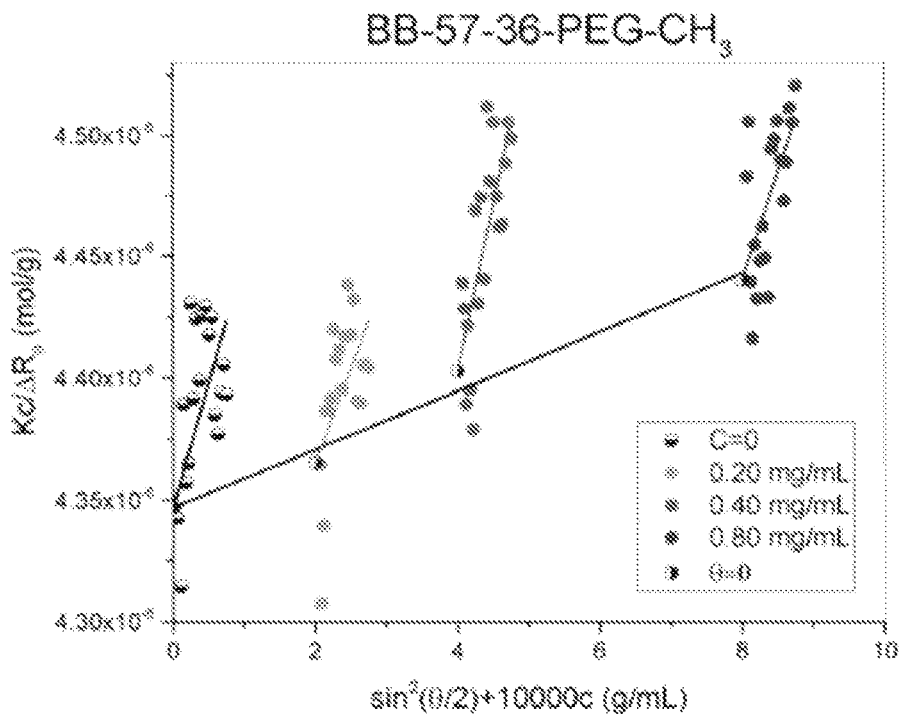
FIG. 11A is a Zimm plot for BB-57-36-PEG-CH$_3$.
Figure 11B:
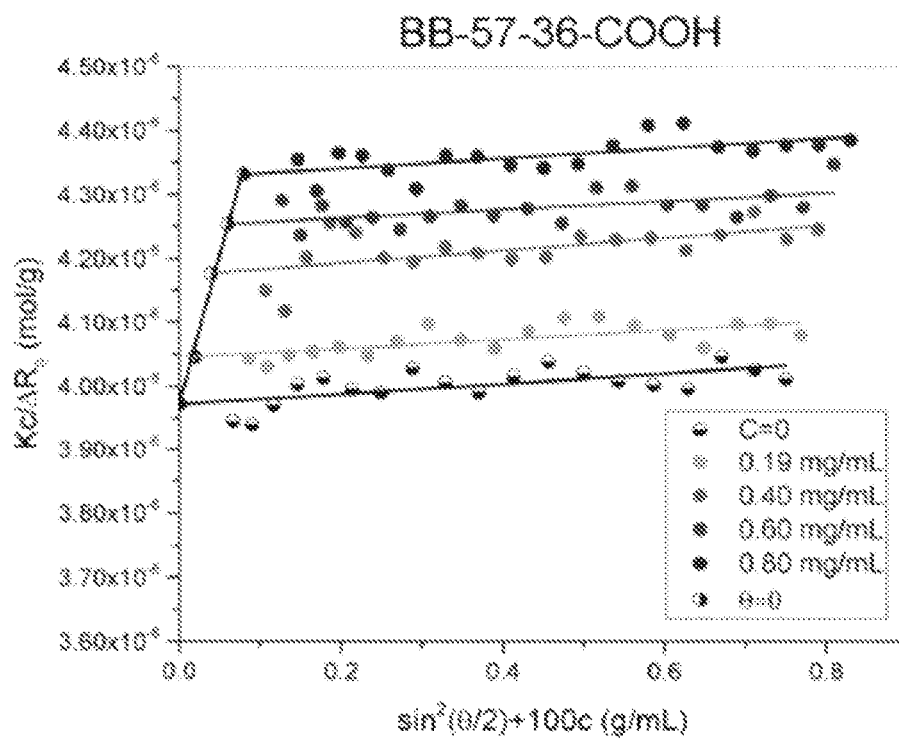
FIG. 11B is a Zimm plot for BB-57-36-COOH, each measured at 25° C. in PBS buffer at pH 6.5.
Figure 12A:
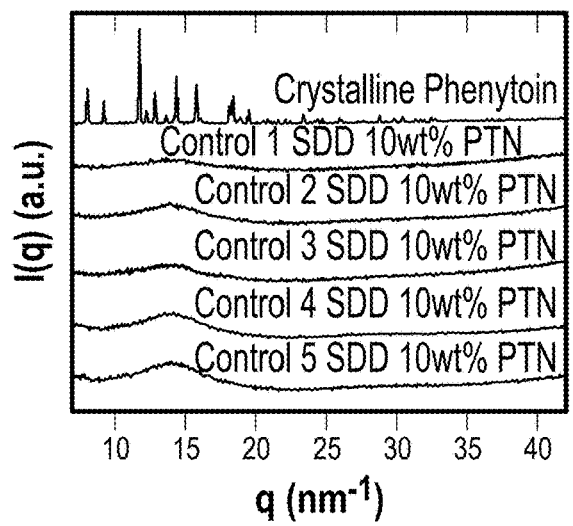
FIGS. 12A-E shows WAXS patterns for all PASD's with 10 and 25 wt % PTN, compared to the crystalline PTN control showing that all PASD's are amorphous. Controls were (1) PA-PND-245-C$_3$H$_7$, (2) PA-PND-61-C$_3$H$_7$, (3) PA-PND-62-C$_3$H$_7$, (4) CA-PND-62-C$_{12}$H$_{25}$, and (5) CP-PND-72-C$_{12}$H$_{25}$.
Figure 12B:
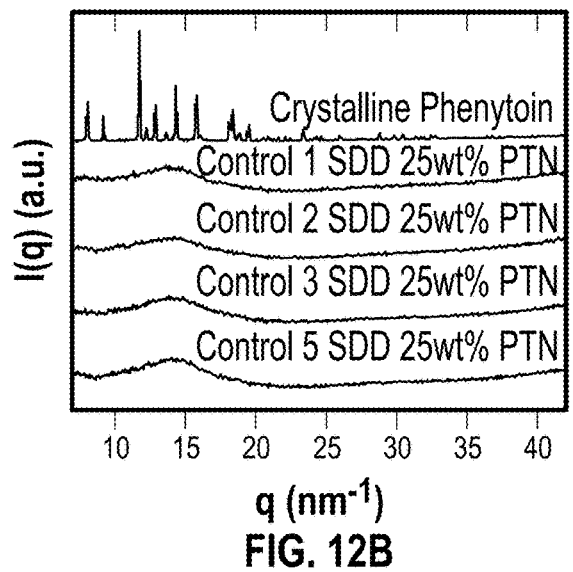
Figure 12C:
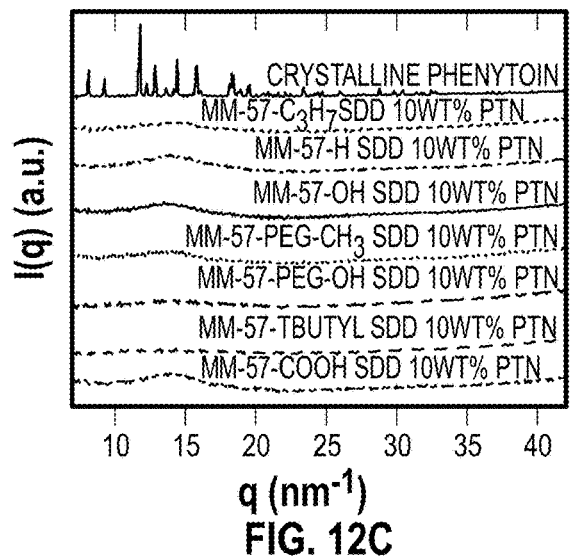
Figure 12D:
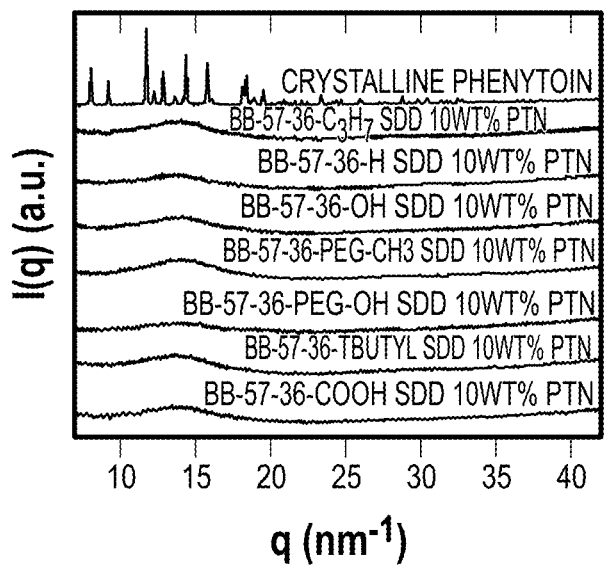
Figure 12E:
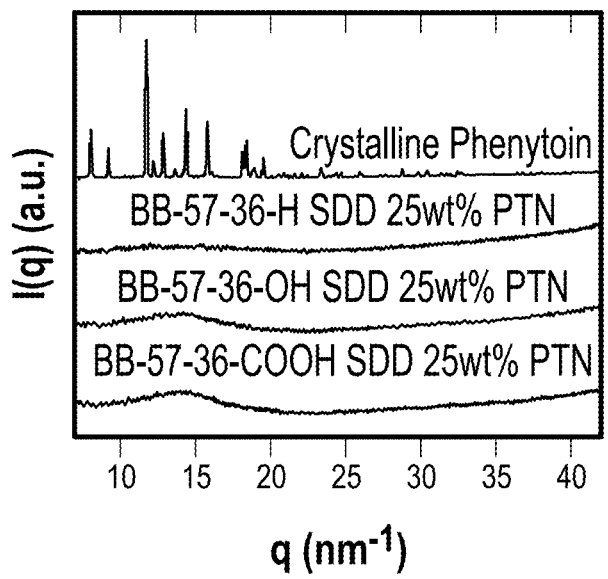
Figure 13A:
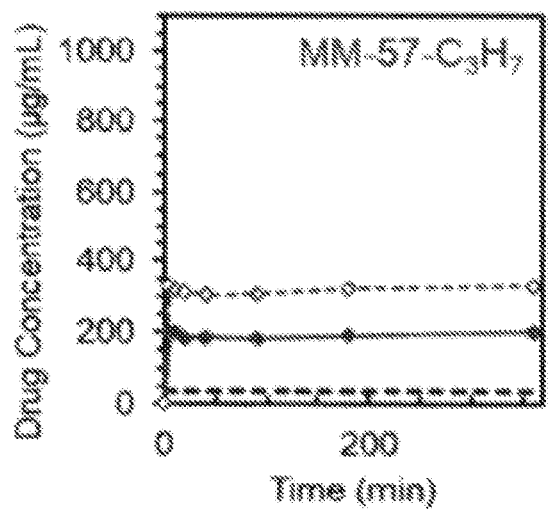
FIGS. 13A-G) includes a series of plots showing dissolution performance of MM-57-Z in 0.5 wt % FaSSIF at 25 (dashed lines) and 37 (solid lines) ° C. with 10 wt % PTN FIGS. 14A-C includes a series of plots showing dissolution performance of BB-57-36-H, —OH, and —COOH in 0.5 wt % FaSSIF at 25 and 37° C. with 25 wt % PTN loading.
Figure 13B:
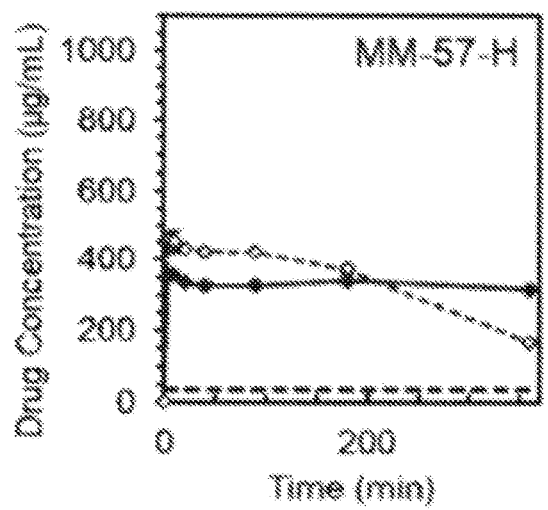
Figure 13C:
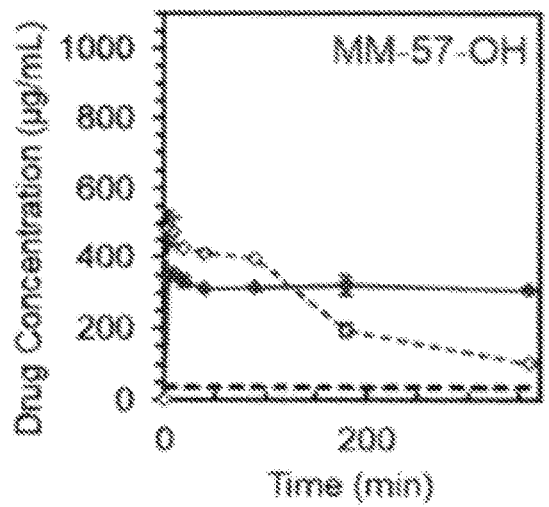
Figure 13D:
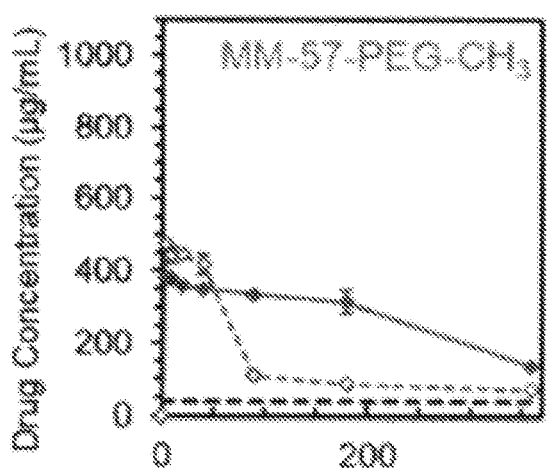
Figure 13E:
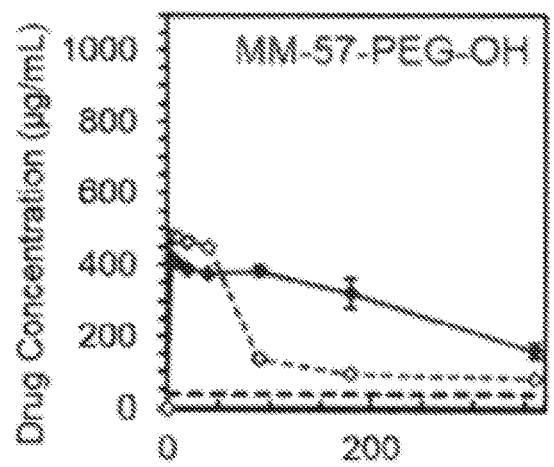
Figure 13F:
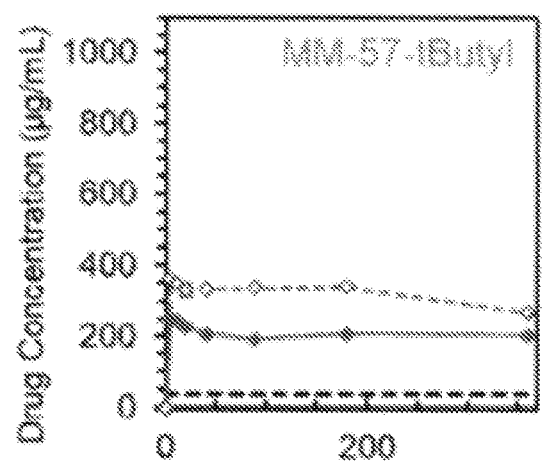
Figure 13G:
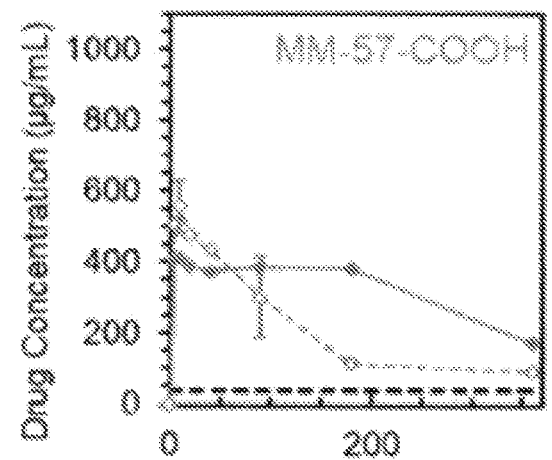

Zimm plots for BB-57-36-PEG-CH$_3$ are shown in FIG. 11A, and BB-57-36-COOH are shown in FIG. 11B, both in PBS buffer at pH 6.5.

Performance Testing

Spray Drying

Each sample with appropriate amount of phenytoin (10 or 25 wt %) was dissolved in methanol (2 mg/mL). After thorough mixing, the sample was transferred to a 20 mL syringe, and using a Bend Research Mini Spray Dryer (Bend, OR), the sample was spray dried using the following parameters: solution flow rate=0.65 mL/min, inlet temperature=70° C. nitrogen flow rate=12.8 standard liter per minute (SLPM). The powder was collected on filter paper and dried under vacuum overnight before dissolution tests. The samples were stored in a vacuum desiccator at room temperature.

Wide-Angle X-Ray Scattering

Polymer amorphous spray dried dispersions were characterized using WAXS from the Advanced Photon Source (APS) at Argonne National Lab on the DND-CAT 5-ID-D beamline. Samples were suspended between two layers of Kapton tape on a silicon washer for sampling. The x-ray beam wavelength at APS was 0.7293 Å and 8.5025 m sample-to-detector distance. The samples were processed by subtracting a blank run of two layers of Kapton tape as a background.

WAXS patterns for all PASD's with PTN are shown in FIGS. 12A-12E compared to the crystalline PTN control showing that all PASD's are amorphous. Controls (1) PA-PND-245-C$_3$H$_7$, (2) PA-PND-61-C$_3$H$_7$, (3) PA-PND-62-C$_3$H$_7$, (4) CA-PND-62-C$_{12}$H$_{25}$, and (5) CP-PND-72-C$_{12}$H$_{25}$.

Dissolution

Each dissolution experiment was run in triplicate. Each spray dried dispersion was weighed out into 2 mL centrifuge tubes to which FaSSIF pH 6.5 was added at the desired temperature. The samples were vortexed for 1 minute and placed in a hot plate set at the desired temperature. At 4 minutes, the samples were removed from the hot plate and centrifuged for 1 minute at 13,000 rpm in a pre-heated centrifuge to maintain temperature. After centrifugation, a 50 µL aliquot of each supernatant was taken and then the samples were again vortexed for 1 minute before returning to the hot plate. This process was repeated at 4, 10, 20, 40, 90, 180, and 360 minutes. Each aliquot was diluted with 450 µL of HPLC grade methanol and filtered through a 0.2 um filter prior to analyzing with HPLC with a mobile phase of 60:40 water:acetonitrile.

Dissolution performance of MM-57-Z in 0.5 wt % FaSSIF at 25 (dashed lines) and 37 (solid lines) ° C. with 10 wt % PTN loading is shown in FIGS. 13A-13G.

Figure 14A:
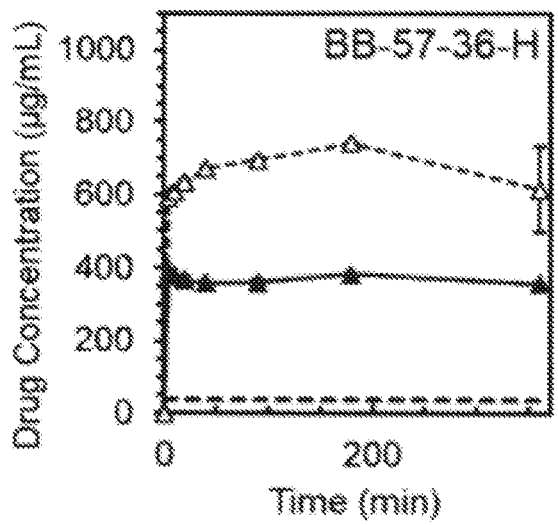
Figure 14B:
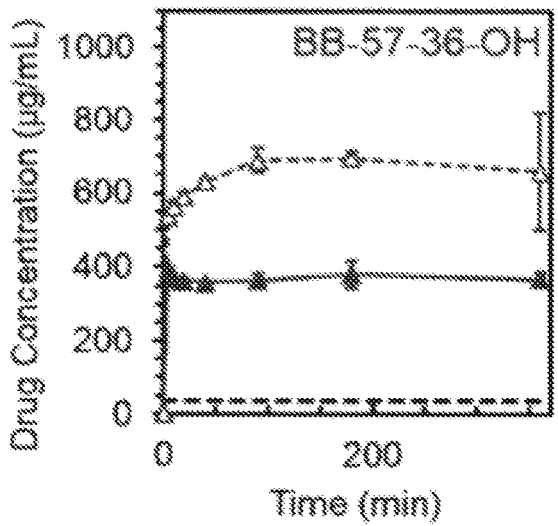
Figure 14C:
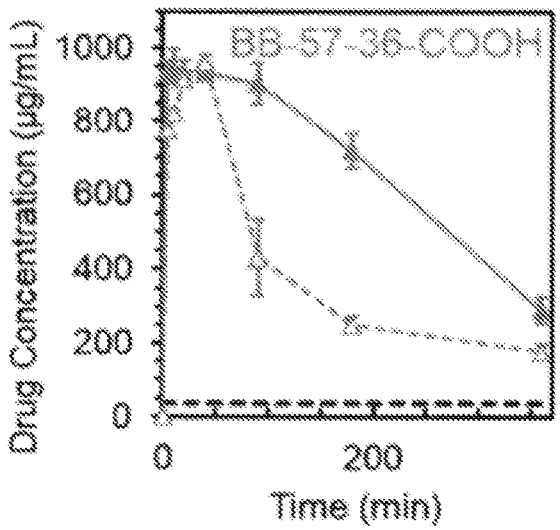
Figure 15A:
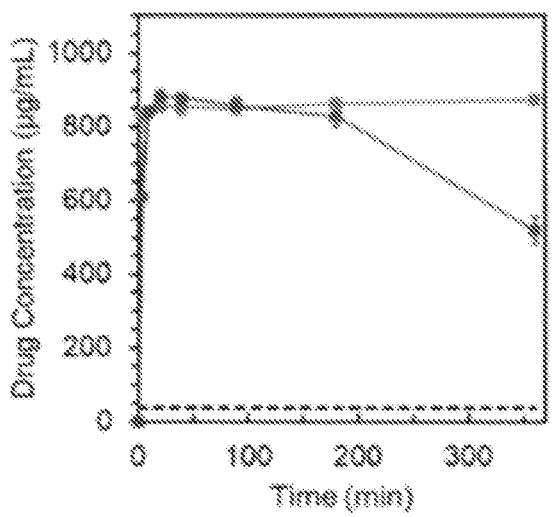
FIGS. 15A-C are a series of plots showing dissolution performance of BB-57-36-COOH at 10 wt % (light orange) and 25 wt % (dark orange) PTN loading and DLS analysis of the supernatant at 37° C. in PBS to investigate the mechanism of drug solubilization and nanoparticle formation with drug.
Figure 15B:
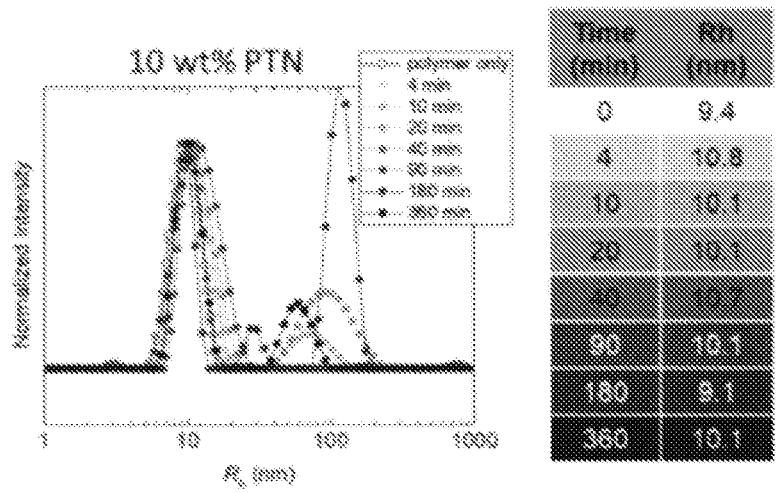
Figure 15C:
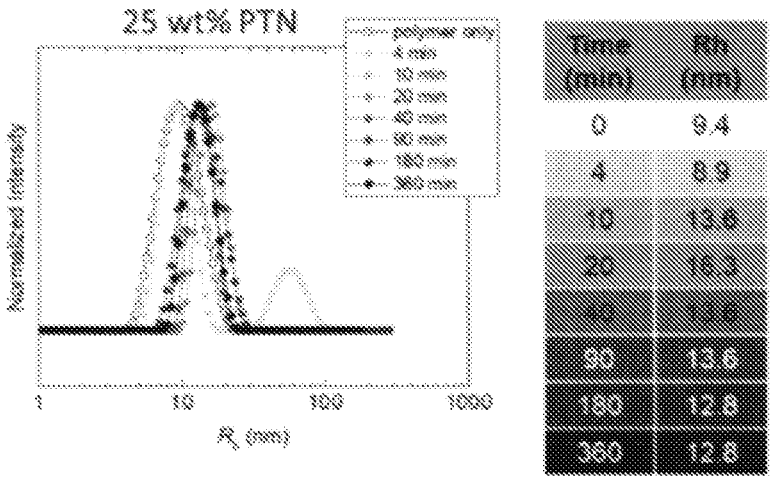

Dissolution performance of BB-57-36-H, —OH, and —COOH in 0.5 wt % FaSSIF at 25 and 37° C. with 25 wt % PTN loading is shown in FIGS. 14A-14C.

Dynamic Light Scattering Dissolution:

All measurements were taken on an in-house photometer (30 mW laser power, avalanche photodiode detector with a 200 µm pinhole) over a range of angles (60-120°) with a Brookhaven BI-200SM goniometer and a Brookhaven BI-9000AT correlator at λ=637 nm at 37° C. Dissolution experiments were performed in PBS (pH 6.5) alone without FaSSIF to mimic the dissolution environment during the DES measurements. The dissolution data collected at 10 and 25 wt % PTN loading at 37° C. in PBS only are shown to the right of the DLS distributions in Figures S # and S #. A DLS measurement was collected of each polymer at 9 and 4 mg/mL at 37 C as a polymer only control. Dissolution vials were vortexed and incubated at 37° C. following the dissolution procedure described above. After centrifugation, a 250 µL aliquot was taken of the supernatant and filtered through a 0.45 µm filter (to remove dust) into a DLS tube before being placed into a Brookhaven Instrument which had been preheated to 37° C. The DLS measurement was taken for 30 sec to 5 minutes depending on baseline stability. For the more dynamic samples, shorter acquisition times were observed. Each correlation function collected was fit with a REPES Laplace inversion to acquire the intensity vs. $R_h$ plots.

Dissolution performance of BB-57-36-COOH at 10 wt % (light orange) and 25 wt % (dark orange) PTN loading and DLS analysis of the supernatant at 37° C. in PBS to investigate the mechanism of drug solubilization and nanoparticle formation with drug is shown in FIG. 16.

Figure 16A:
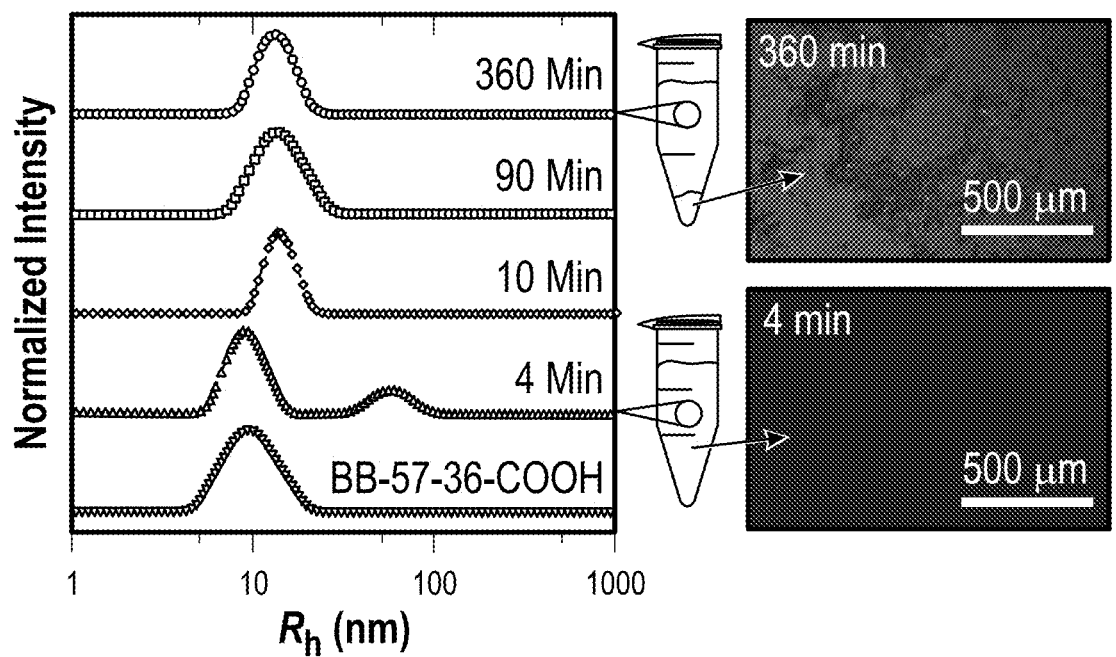
FIG. 16A shows dynamic light scattering measurements during dissolution of BB-57-36-COOH with 25 wt % PTN in PBS at pH 6.5 and 37° C. at 4, 10, 90, and 360 minutes during dissolution. BB-57-36-COOH in PBS at pH 6.5 and 37° C. at 9 mg/mL without drug (open circles).
Figure 16B:
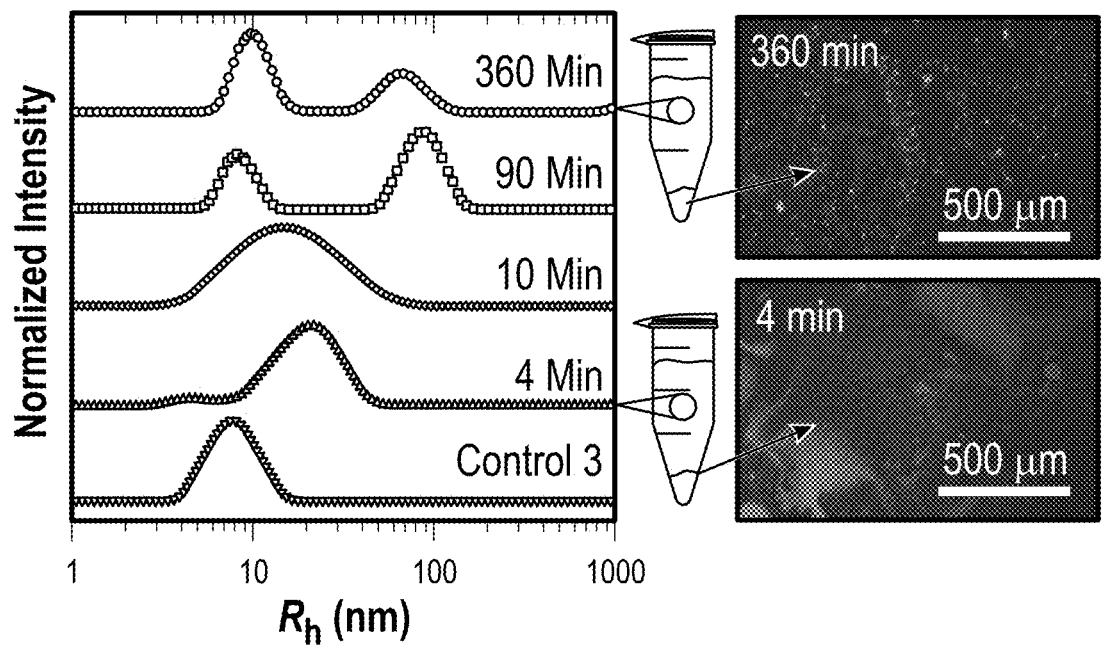
FIG. 16B shows dynamic light scattering measurements during dissolution of PA-PND-62-C$_{12}$H$_{25}$ with 25 wt % PTN in PBS at pH 6.5 and 37° C. at 4, 10, 90, and 360 minutes during dissolution. PA-PND-62-C$_{12}$H$_{25}$ in PBS at pH 6.5 and 37° C. at 9 mg/mL without drug (open circles).

Dynamic light scattering measurements during dissolution in PBS pH 6.5 at 37° C. and 25 wt % PTN are shown in FIGS. 16A-B.

FIG. 16A shows BB-57-36-COOH at 9 mg/mL without drug (open circles) at 4, 10, 90, and 360 minutes during dissolution. At 4-10 min, no precipitate was observed in the sample vial as shown in the cartoon and the PLM image (bottom right), but there was a pellet of crystallized drug after centrifugation during 90-360 min as shown in the PLM image (top right).

FIG. 16B shows 9 mg/mL of PA-PND-62-$C_{12}H_{25}$ without drug (open circles) at 4, 10, 90, and 360 minutes during dissolution. All samples were observed to have a precipitate in the bottom of vial after centrifugation. At 4 min, the precipitate is amorphous as shown in the PLM image (bottom right), but by 360 min the precipitated pellet was crystalline as shown by the birefringence m the PLM image (top right).

Polarized Light Microscopy

Images were collected under normal dissolution conditions. However, each sample aliquot was taken after 30 sec of vortexing instead of centrifugation to gain a holistic understanding about the presence of crystalline or amorphous precipitates in the dissolution vial. At each timepoint, after vortexing, a 20 μL aliquot was taken and deposited on a precleaned glass slide (3"×1", Thermo Scientific) the droplet was dispersed with a glass cover slip (24×40 mm², Fisher). The samples were imaged with a Canon SL 1 digital camera mounted on a Nikon Optiphoto polarized microscope at 10× magnification. Each image, bright field or polarized was taken within 3 minutes of sampling. The images of the pellet were taken at the respective timepoints after 1 minute of centrifugation (13,000 rpm) after removing all of the supernatant and transferring the remaining pellet onto a glass slide. Image analysis was performed using Image) (Nation institutes of Health, MD, USA).

Figure 17A:
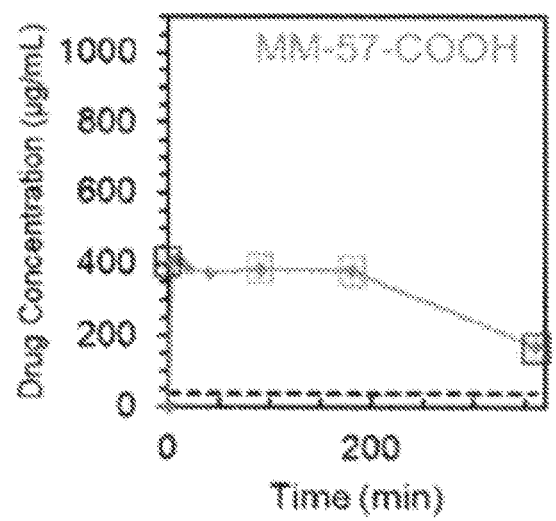
FIGS. 17A-B show polarized and bright field light microscopy images of MM-57-COOH at 37° C. during dissolution with 10 wt % PTN at (a) 4, (b) 90, (c) 180, and (d) 360 minutes.
Figure 17B:
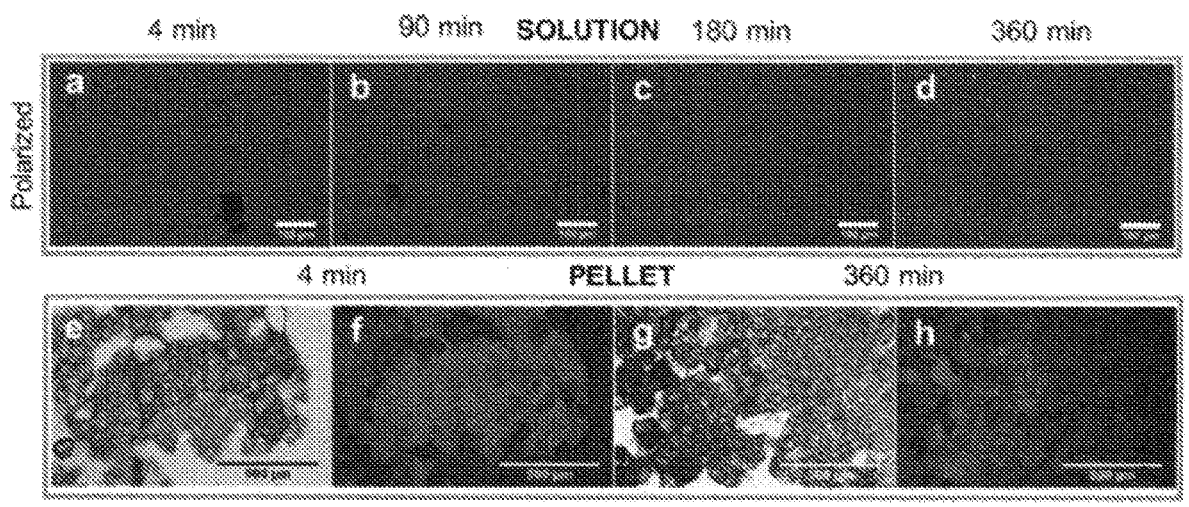

The polarized and bright field light microscopy images of MM-57-COOH at 37° C. during dissolution with 10 wt % PTN at 4, 90, 180, and 360 minutes are shown in FIGS. 17A-B. The polarized light microscopy images at (a) 4 min, (b) 90 min, (c) 180 min, and (d) 360 min show 10-100 micron sized amorphous particles that decrease in size overtime before crystallization occurs at 360 min. The (e) bright field and (f) polarized images of the pellet at 4 minutes confirms that the suspended particles when centrifuged down are amorphous, and at 360 min, the (g) bright field and (h) polarized images show that the centrifuged are partially crystalline as seen in the solution.

Figure 18A:
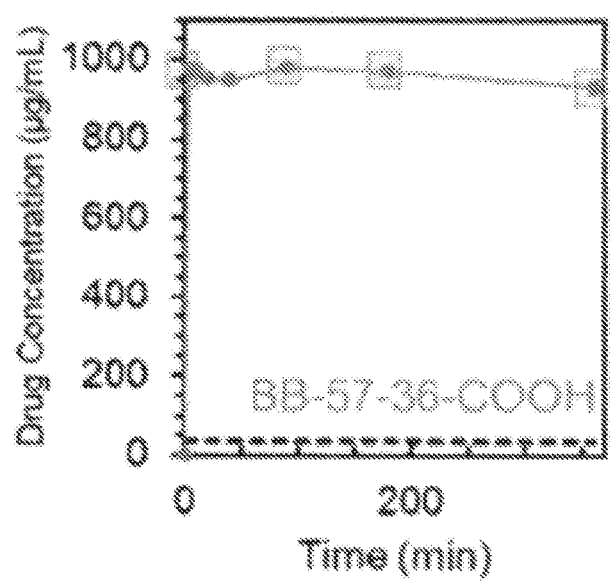
FIGS. 18A-B show polarized light microscopy images for the solution of BB-57-36-COOH during dissolution at 37° C. with 10 wt % PTN loading at (a) 4, (b) 90, (c) 180, and (d) 360 minutes.
Figure 18B:
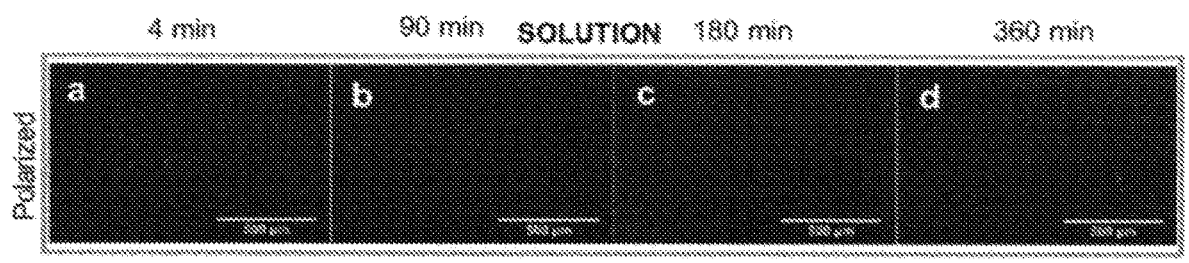

Polarized light microscopy images for the solution of BB-57-36-COOH during dissolution at 37° C. with 10 wt % PTN loading at (a) 4, (b) 90, (c) 180, and (d) 360 minutes is shown in FIGS. 18A-18B. No particles are visible in the solution and only a very small amount of crystallization is observable at 360 minutes.

Figure 19A:
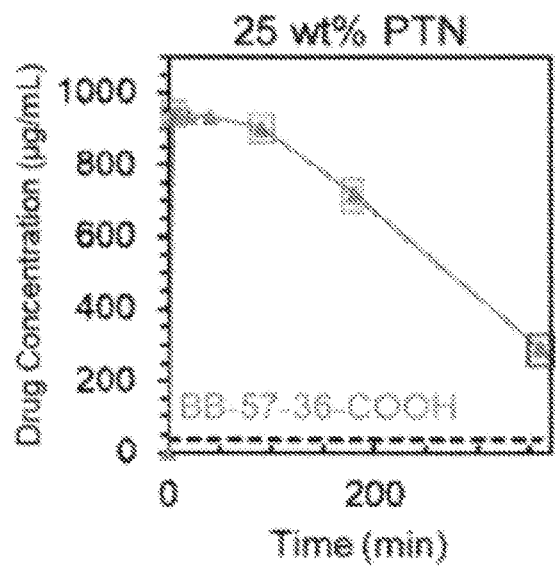
FIGS. 19A-B show polarized and bright field light microscopy images during the dissolution of BB-57-36-COOH at 37° C. with 25 wt % PTN at (a) 4, (b) 90, (c) 180, and (d) 360 minutes.
Figure 19B:
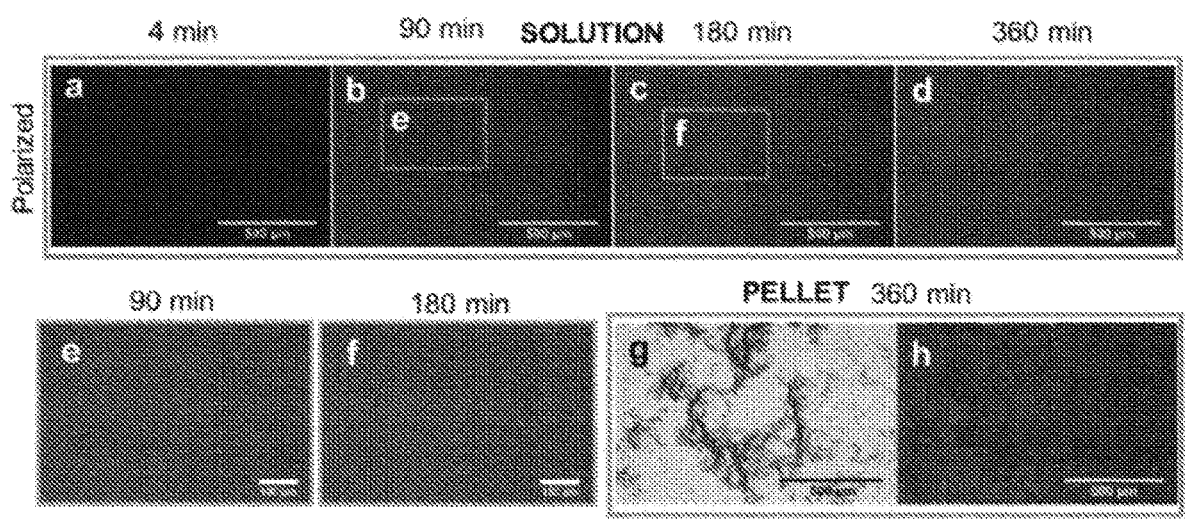

Polarized and bright field light microscopy images during the dissolution of BB-57-36-COOH at 37° C. with 25 wt % PTN at 4, 90, 180, and 360 minutes are shown in FIGS. 19A-19B. The polarized images of the solution at (a) 4, (b) 90, (c) 180, and (d) 360 minutes show that the ASD completely dissolves initially, but by 90 min, 10 μm spherulite-like crystalline particles form that transition into rod-like crystals (shown in inset (e) and (f)) over the course of 6 hours. (g) Bright field and (h) polarized light images of the pellet after centrifugation at 360 minutes showing that the precipitate that formed during the dissolution is crystalline.

Figure 20A:
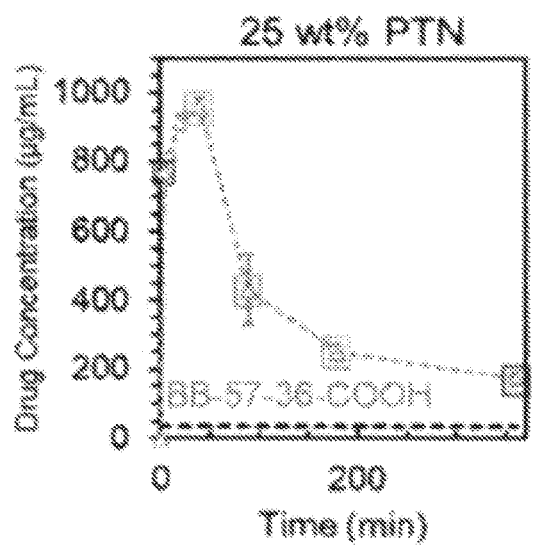
FIGS. 20A-B show polarized and bright field light microscopy images during the dissolution of BB-57-36-COOH at 25° C. with 25 wt % PTN at (a) 4, (b) 40, (c) 90, (d) 180, and (e) 360 minutes.
Figure 20B:
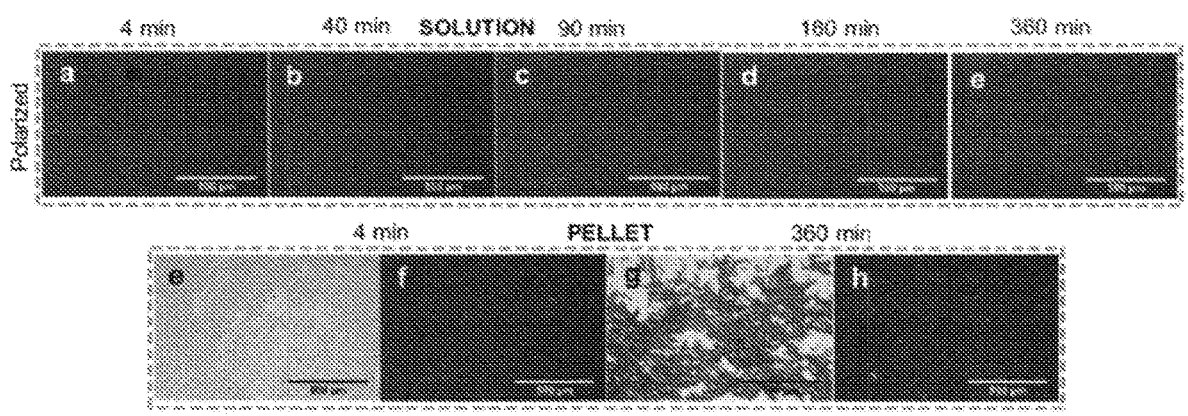

Polarized and bright field light microscopy images during the dissolution of BB-57-36-COOH at 25° C. with 25 wt % PIN at 4, 40, 90, 180, and 360 minutes are shown in FIGS. 20A-20B. The polarized images of the solution at (a) 4, (b) 40, (c) 90, (d) 180, and (e) 360 minutes show that it takes 40 minutes for the ASD to completely dissolve before rapid crystallization occurs by 90 minutes leading to very few suspended particles present in solution after 6 hours. (f) Bright field and (g) polarized light images of the pellet after centrifugation at 4 minutes showing that the precipitate that formed during initially is amorphous. (h) Bright field and (i) polarized light images showing the complete precipitation of the drug into rod-like crystals after 6 hours.

EMBODIMENTS

Embodiment A. A composition, comprising:
a macromolecular polyacrylamide copolymer excipient with an α-end comprising a ROMP-active norbornene end-group and a ω-end comprising a terminal monomer with and end group chosen from:
a hydrogen atom (H); or
a functionalized acrylate with functionality chosen from alkyl, hydroxyl (OH), methyl-polyethylene glycol ((PEG)-$CH_3$), hydroxy-PEG (PEG-OH), carboxylic acid (COOH), and combinations thereof and
a biological compound non-covalently bound with the macromolecular excipient,
wherein the biological compound is chosen from active pharmaceutical ingredients, proteins, polynucleotides, and mixtures and combinations thereof.

Embodiment B. The composition of Embodiment A, wherein the acrylate alkyl functionality is tert-butyl.

Embodiment C. The composition of Embodiments A or B, wherein the polyacrylamide copolymer comprises poly(N-isopropylacramide (NIPAm)/N,N-dimethylacrylamide (DMA)).

Embodiment D. The composition of Embodiment C, wherein the ratio of NIPAm DMA in the copolymer is about 70:30.

Embodiment E. The composition of Embodiment C, wherein the ratio of NIPAm to DMA in the copolymer is about 60:40.

Embodiment F. The composition of Embodiment C, wherein the ratio of NIPAm to DMA in the copolymer is about 65:35.

Embodiment G. The composition of any of Embodiments A to F, wherein the molecular weight of the polyacrylamide is about 4 kDa to about 32 kDa.

Embodiment H. The composition of any of Embodiments A to G, wherein the excipient has a cloud point temperature ($T_{cp}$) of about 30° C. to about 45° C.

Embodiment I. The composition of any of Embodiments A to H, wherein the composition is in the form of single chains and a major population exists with a hydrodynamic radius ($R_h$) at 25° C. of about 2 nm to about 5 nm, and wherein the excipient has a polydispersity index of less than about 0.35.

Embodiment J. A composition, comprising:
an excipient with a bottle-brush morphology, wherein the excipient comprises a backbone polymer derived from norbornene and a plurality of filamentous arms attached to the backbone polymer, wherein the arms comprise a polyacrylamide copolymer, the polyacrylamide copolymer comprising a terminal monomer with and end group chosen from:
a hydrogen atom (H); or
a functionalized acrylate with functionality chosen from alkyl, hydroxyl (OH), methyl-polyethylene glycol ((PEG)-$CH_3$), hydroxy-PEG (PEG-OH), carboxyl (COOH), and combinations thereof; and
a biological compound non-covalently bound with the excipient, wherein the biological compound is chosen from active pharmaceutical ingredients, proteins, polynucleotides, and mixtures and combinations thereof.

Embodiment K. The composition of Embodiment J, wherein the acrylate alkyl functionality is tert-butyl.

Embodiment L. The composition of Embodiments J or K, wherein the polyacrylamide copolymer comprises poly(W-isopropylacrylamide (NIPAm)/N,N-dimethylacrylamide (DMA)).

Embodiment M. The composition of any of Embodiments J to L, wherein the ratio of NIPAm to DMA in the copolymer is about 70:30.

Embodiment N. The composition of any of Embodiments J to M, wherein the ratio of NIPAm to DMA in the copolymer is about 65:35.

Embodiment O. The composition of any of Embodiments J to N, wherein the excipient has a cloud point temperature ($T_{cp}$) of about 20° C. to about 45° C.

Embodiment P. The composition of any of Embodiments J to O, wherein the composition is in the form of monodisperse unimers with a hydrodynamic radius ($R_h$) at 25° C. of about 8 nm to about 12 nm, and wherein the excipient has a polydispersity index of less than about 0.15.

Embodiment Q. A method for making a delivery system for a biological compound, the method comprising:
grafting norbornene functionalized polyacrylamide copolymers together to form a supramolecular macromolecule with the terminal functional group on each arm radiating from the grafted polynorbornene derived backbone comprising an alkyl trithiocarbonate compound; and
reacting the alkyl trithiocarbonate on the macromolectile to form an excipient for the biological compound having a modified functional group, wherein the modified functional group is chosen from:
a completely removed trithiocarbonate group resulting in a hydrogen atom (H), and
a functionalized acrylate with functionality chosen from alkyl, hydroxyl (OH), methyl-polyethylene glycol ((PEG)-$CH_3$), hydroxy-PEG (PEG-OH), carboxyl (COOH), and combinations thereof.

Embodiment R. The method of Embodiment Q, wherein the polyacrylamide copolymer is polymerized via the RAFT process using a trithiocarbonate chain transfer agent.

Embodiment S. The method of Embodiments Q or R, wherein the trithiocarbonate group is removed with photoinduced chain transfer in the presence of a proton donor.

Embodiment T. The method of any of Embodiments Q to S, wherein the trithiocarbonate undergoes aminolysis and subsequent thia-Michael addition with an acrylate to install the desired functional group.

Embodiment U. The method of any of Embodiments Q to T, wherein the alkyl functionality on the trithiocarbonate compound is propyl.

Embodiment V. The method of any of Embodiments Q to U, wherein the acrylate alkyl functionality is tert-butyl.

Embodiment W. The method of any of Embodiments Q to V, wherein the polyacrylamide copolymer comprises poly (N-isopropylacrylamide (NIPAm)/N,N-dimethylacrylamide (DMA)).

Embodiment X. The method of Embodiment W, wherein the ratio of NIPAm to DMA in the copolymer is about 65:35.

Embodiment Y. The method of any of Embodiments Q to X, wherein the excipient comprises a backbone degree of polymerization of about 2 to about 100.

Embodiment Z. The method of any of Embodiments Q to Y, wherein the excipient comprises a backbone degree of polymerization of about 25 to about 50.

Embodiment AA. The method of any of Embodiments Q to Z, wherein the excipient has a dispersity of less than about 1.30.

Embodiment BB. The method of any of Embodiments Q to AA, wherein the excipient has a cloud point temperature ($T_{cp}$) of about 35° C. to about 45° C.

Embodiment CC. The method of any of Embodiments Q to BB, further comprising polymerizing the norbornene functionality on the macromolecule prior to end-group modification using a ROMP process to form a polymer with a bottlebrush morphology, wherein polymer with bottlebrush morphology comprises a backbone polymer derived from the norbornene functionality and a plurality of arms are attached to the backbone polymer, wherein the arms are derived from the macromolecule.

Embodiment DD. The method of any of Embodiments Q to CC, further comprising associating the macromolecule with the modified functional group non-covalently with a biological compound to form a drug delivery composition, wherein the biological compound is chosen from active pharmaceutical ingredients, proteins, polynucleotides, and mixtures and combinations thereof.

Embodiment EE. The method of Embodiment DD, wherein the drug delivery composition is in the form of a monodisperse unimer with a hydrodynamic radius ($R_h$) at 25° C. of about 10 nm to about 50 nm.

Embodiment FE. The method of any of Embodiments Q to EE, further comprising associating the bottlebrush polymer with the modified functional group non-covalently with a biological compound to form a drug delivery composition, wherein the biological compound chosen from active pharmaceutical ingredients, proteins, polynucleotides, and mixtures and combinations thereof.

Embodiment GG. The method of Embodiment FF, wherein the drug delivery composition is in the form of a monodisperse unimer with a hydrodynamic radius ($R_h$) at 25° C. of about 8 nm to about 15 nm.

Embodiment HH. A method for delivering a biological agent into a cell, the method comprising:
providing an excipient with a bottlebrush morphology, wherein the excipient comprises a backbone polymer derived from norbornene and a plurality of filamentous arms attached to the backbone polymer, wherein the anus comprise a polyacrylamide copolymer with terminal functionality chosen from a hydrogen atom (H) and a functional acrylate, wherein the functional acrylate comprises functionality chosen from alkyl, hydroxyl (OH), methyl-polyethylene glycol (PEG-$CH_3$), hydroxy-PEG (PEG-OH), carboxyl (COOH), and combinations thereof;
non-covalently associating a biological agent with the excipient, wherein the biological agent is chosen from active pharmaceutical ingredients, proteins, polynucleotides, and mixtures and combinations thereof;
introducing the excipient and associated biological agent into a pharmaceutically effective liquid carrier to form a drug composition; and
administering the drug composition to a patient such that the biological agent is delivered into a cell of the patient.

Embodiment II. A monodisperse structure in a liquid carrier, the structure comprising:
an excipient with a bottlebrush morphology, wherein the excipient comprises a backbone polymer derived from norbornene and a plurality of filamentous arms attached to the backbone polymer, wherein the arms comprise a polyacrylamide copolymer with a terminal functional group chosen from a hydrogen atom (H) and a functionalized acrylate with functionality chosen from alkyl, hydroxyl (OH), methyl-polyethylene glycol ((PEG)-CH$_3$), hydroxy-PEG (PEG-OH), carboxyl (COOH), and combinations thereof; and a biological agent non-covalently associated with the excipient to form a drug loaded nanoparticle, wherein the biological agent is chosen from active pharmaceutical ingredients, proteins, polynucleotides, and mixtures and combinations thereof, wherein the micelle has a hydrodynamic radius ($R_h$) at 25° C. of about 8 nm to about 25 nm.

Embodiment JJ. A method of making a drug composition, the method comprising spray drying a biological agent chosen from active pharmaceutical ingredients, proteins, polynucleotides, and mixtures and combinations thereof with an excipient comprising a backbone polymer derived from norbornene and a plurality of filamentous arms attached to the backbone polymer, wherein the arms comprise a polyacrylamide copolymer with terminal functionality chosen from a hydrogen atom (H) and a functionalized acrylate with functionality chosen from alkyl, hydroxyl (OH), methyl-polyethylene glycol ((PEG)-$CH_3$), hydroxy-PEG (PEG-OH), carboxyl (COOH), and combinations thereof.

Embodiment KK. The method of Embodiment JJ, wherein the acrylate functionality is COOH.

Embodiment LL. The method of Embodiments JJ or KK, wherein the biological agent was present in an amount of about 10 wt % to about 50 wt %, based on the total weight of the drug composition.

Embodiment MM. The method of any of Embodiments JJ to LL, wherein the biological agent was present in an amount of about 10 wt % to about 25 wt %, based on the total weight of the drug composition.

Embodiment NN. The method of Embodiment MM, wherein the drug composition comprises particles with a hydrodynamic radius ($R_h$) at 37° C. of about 8 nm to about 25 nm, and wherein the particles are stable in solution of fasted-state simulated intestinal fluid for about 6 hours.

Embodiment OO. The method of any of Embodiments JJ to NN, wherein the drug composition solubilized 1000 μg/μL of the biological agent at 25 wt % loading for up to 90 minutes.

Various embodiments of the invention have been described. These and other embodiments are within the scope of the following claims.

The invention claimed is:

1. A composition, comprising:

a macromolecular polyacrylamide copolymer excipient with an α-end comprising a ROMP-active norbornene end-group and a ω-end comprising a terminal monomer with an end group chosen from:

a hydrogen atom (H); or a functionalized acrylate with functionality chosen from alkyl, hydroxyl (OH), methyl-polyethylene glycol ((PEG)-$CH_3$), hydroxy-PEG (PEG-OH), carboxylic acid (COOH), and combinations thereof; and a biological compound non-covalently bound with the macromolecular excipient, wherein the biological compound is chosen from active pharmaceutical ingredients, proteins, polynucleotides, and mixtures and combinations thereof.

2. The composition of claim 1, wherein the acrylate alkyl functionality is tert-butyl.

3. The composition of claim 1, wherein the polyacrylamide copolymer comprises poly(N-isopropylacrylamide (NIPAm)/N,N-dimethylacrylamide (DMA)).

4. The composition of claim 3, wherein the ratio of NIP, n to DMA in the copolymer is about 70:30.

5. A composition, comprising:

excipient with a bottle-brush morphology, wherein the excipient comprises a backbone polymer derived from norbornene and a plurality of filamentous arms attached to the backbone polymer, wherein the arms comprise a polyacrylamide copolymer, the polyacrylamide copolymer comprising a terminal monomer with an end group chosen from:

a hydrogen atom (H); or a functionalized acrylate with functionality chosen from alkyl, hydroxyl (OH), methyl-polyethylene glycol ((PEG)-$CH_3$), hydroxy-PEG (PEG-OH), carboxyl (COOH), and combinations thereof; and a biological compound non-covalently hound with the excipient, wherein the biological compound is chosen from active pharmaceutical ingredients, proteins, polynucleotides, and mixtures and combinations thereof.

6. The composition of claim 5, wherein the acrylate alkyl functionality is tert-butyl.

7. The composition of claim 5, wherein the polyacrylamide copolymer comprises poly(N-isopropylacrylamide (NIPAm)/NN-dimethylacrylamide (DMA)).

8. The composition of claim 7, wherein the ratio of NIPAm to DMA in the copolymer is about 70:30.

9. A method for making a delivery system for a biological compound, the method comprising:

grafting norbornene functionalized polyacrylamide copolymers together to form a supramolecular macromolecule with the terminal functional group on each arm radiating from the grafted polynorbornene derived backbone comprising an alkyl trithiocarbonate compound; and reacting the alkyl trithiocarbonate on the macromolecule to form an excipient for the biological compound having a modified functional group, wherein the modified functional group is chosen from:

a completely removed trithiocarbonate group resulting in a hydrogen atom (H), and a functionalized acrylate with functionality chosen from alkyl, hydroxyl (OH), methyl-polyethylene glycol ((PEG)-$CH_3$), hydroxy-PEG (PEG-OH), carboxyl (COOH), and combinations thereof.

10. The method of claim 9, wherein the polyacrylamide copolymer is polymerized via the RAFT process using a trithiocarbonate chain transfer agent.

11. The method of claim 9, wherein the trithiocarbonate group is removed with photoinduced chain transfer in the presence of a proton donor.

12. The method of claim 9, wherein the trithiocarbonate undergoes aminolysis and subsequent thia-Michael addition with an acrylate to install the desired functional group.

13. The method of claim 9, wherein the alkyl functionality on the trithiocarbonate compound is propyl.

14. The method of claim 9, wherein the acrylate alkyl functionality is tert-butyl.

15. The method of claim 9, wherein the polyacrylamide copolymer comprises poly(N-isopropylacrylamide (NIPAm)/N,N-dimethylacrylamide (DMA)).

16. The method of claim 15, wherein the ratio of NIPAm to DMA in the copolymer is about 65:35.

17. The method of claim 9, wherein the excipient comprises a backbone degree of polymerization of about 2 to about 100.

18. The method of claim 9, further comprising polymerizing the norbornene functionality on the macromolecule prior to end-group modification using a ROMP process to form a polymer with a bottlebrush morphology, wherein polymer with bottlebrush morphology comprises a backbone polymer derived from the norbornene functionality and a plurality of arms are attached to the backbone polymer, wherein the arms are derived from the macromolecule.

19. The method of claim 18, further comprising associating the macromolecule with the modified functional group non-covalently with a biological compound to foi nE a drug delivery composition, wherein the biological compound is chosen from active pharmaceutical ingredients, proteins, polynucleotides, and mixtures and combinations thereof.

20. The method of claim 18, further comprising associating the bottlebrush polymer with the modified functional group non-covalently with a biological compound to form a drug delivery composition, wherein the biological compound chosen from active pharmaceutical ingredients, proteins, polynucleotides, and mixtures and combinations thereof.

* * * * *